US010955291B2

(12) United States Patent
Hart et al.

(10) Patent No.: US 10,955,291 B2
(45) Date of Patent: Mar. 23, 2021

(54) METHODS OF DETERMINING EXPOSURE TO UV LIGHT

(71) Applicant: Amgen Inc., Thousand Oaks, CA (US)

(72) Inventors: Roger Hart, Loveland, CO (US); Amanda Lewis, Boulder, CO (US); Brent Welborn, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 320 days.

(21) Appl. No.: 14/385,249

(22) PCT Filed: Mar. 7, 2013

(86) PCT No.: PCT/US2013/029648
§ 371 (c)(1),
(2) Date: Sep. 15, 2014

(87) PCT Pub. No.: WO2013/138159
PCT Pub. Date: Sep. 19, 2013

(65) Prior Publication Data
US 2015/0053546 A1    Feb. 26, 2015

Related U.S. Application Data

(60) Provisional application No. 61/611,362, filed on Mar. 15, 2012.

(51) Int. Cl.
*G01J 1/42* (2006.01)
*G01N 33/52* (2006.01)
(Continued)

(52) U.S. Cl.
CPC .............. *G01J 1/429* (2013.01); *A23L 3/28* (2013.01); *A61L 2/0035* (2013.01); *A61L 2/0047* (2013.01); *A61L 2/10* (2013.01); *G01N 21/6486* (2013.01); *G01N 33/52* (2013.01); *A61L 2202/21* (2013.01); *G01N 2201/06113* (2013.01)

(58) Field of Classification Search
CPC .......... G01J 1/429; A61L 2/10; A61L 2/0047; A61L 2/0035; A61L 2202/21; G01N 21/6486; G01N 33/52; G01N 2201/06113; A23L 3/28
USPC .......................... 204/158.2; 422/24; 250/372
See application file for complete search history.

(56) References Cited

U.S. PATENT DOCUMENTS 6,395,555 B1 *  5/2002  Wilson ............... G01N 33/5008
                                                              436/2
7,372,039 B2 *  5/2008  Tokhtuev ............... G01N 21/33
                                                              250/356.1

(Continued)

OTHER PUBLICATIONS

Derwent Abstract of CN 101323884 A (Year: 2008).*
(Continued)

*Primary Examiner* — Nicholas A Smith
*Assistant Examiner* — Colleen M Raphael
(74) *Attorney, Agent, or Firm* — Susan E. Lingenfelter

(57) ABSTRACT

Methods of determining the dose of UVC light delivered to a sample comprising a low optical transmission complex fluid are provided. Also provided are methods of inactivation of an organism, such as a spore, a bacteria or a virus, in a sample comprising dose of UVC light delivered to a sample comprising a low optical transmission complex fluid.

14 Claims, 43 Drawing Sheets

(51) Int. Cl.
*A61L 2/00* (2006.01)
*A23L 3/28* (2006.01)
*A61L 2/10* (2006.01)
*G01N 21/64* (2006.01)

(56) References Cited

U.S. PATENT DOCUMENTS

| | | | | |
|---|---|---|---|---|
| 2004/0197814 | A1* | 10/2004 | Cowsert | G16C 20/60 435/6.11 |
| 2010/0118301 | A1* | 5/2010 | Vondras | G01N 33/0042 356/318 |
| 2013/0078702 | A1* | 3/2013 | Dhanasekharan | A61L 2/0047 435/173.3 |

OTHER PUBLICATIONS

Derwent Abstract of CN 101831507 A (Year: 2010).*
Bohrerova, et al., "Experimental Measurements of Fluence Distribution in a UV Reactor Using Fluorescent Microspheres". Environ. Sci. Technol., 39, 8925-8930 (Nov. 1, 2005).
De Souza, Poliana Mendes, "Study of short-wave ultraviolet treatments (UV-C) as a non-thermal preservation process for liquid egg products", Retrieved from the Internet: http://riunet.upv.es/bitstream/handle/10251/16696/tesisUPV3865.pdf?sequence=1 ,pp. 75-77 (2007).
Shen, C., et al., "Validation of medium-pressure UV disinfection reactors by Lagrangian actinometry using dyed microspheres". Water Research; v:43 1:5, p. 1370-1380; (2009).
Zhao, "Analysis of a Low Pressure UV reactor under Multiple Upstream Elbow Configurations using UV Sensitive Fluorescent Microspheres". Retrieved from the Internet : URL: http: //repository.lib.nesu.edu/ir/ bitstream/1840.16/2008/1/etd.pdf. [retrieved on Jun. 20, 2013) Jan. 1, 2007.

* cited by examiner

METHODS OF DETERMINING EXPOSURE TO UV LIGHT

CROSS-REFERENCE TO RELATED APPLICATIONS

This application is a national stage application under 35 U.S.C. § 371 of International Application No. PCT/US2013/029648, having an international filing date of Mar. 7, 2013; which claims priority to U.S. Provisional Patent Application No. 61/611,362, filed Mar. 15, 2012, which are incorporated herein by reference.

FIELD OF THE INVENTION

The present invention relates generally to compounds and processes for determining the dose of UV light delivered to a sample, which finds application in a variety of fields, including the inactivation of organisms such as bacteria, viruses and spores using light in the UVC wavelengths and the activation and/or inhibition of chemical reactions.

BACKGROUND OF THE INVENTION

Viral contamination of cell culture media and supernatants poses a challenge to biopharmaceutical manufacturers worldwide. Several methods have been employed to inactivate and/or remove large or small, enveloped or non-enveloped (or "naked") DNA or RNA viral particles from cellular supernatants. Examples of these approaches include 20 nm filtration technology, anion-exchange membrane chromatography, low pH incubation and depth filter technology.

In addition to the above techniques, ultraviolet (UV) light, notably light in the UVC band, has also been used to treat low transmission solutions, including cell culture media, in order to inactivate viruses. In order to achieve efficient viral inactivation, however, the solution must be exposed to a sufficient and well-defined dose of UV light, in the UVC band, in order to ensure a desired level of viral inactivation. Continuing assurance of efficient viral inactivation relies on accurate quantification of the dose of UVC radiation received by the low optical transmission solution.

Currently, there are two common methods used to quantify the germicidal dose delivered to fluids by a UVC reactor. The first method uses biodosimetry, whereby a challenge micro-organism (e.g., a virus such as a parvovirus) is spiked into the fluid being treated by a reactor and the inactivation kinetics are determined. Biodosimetry results define an average fluency delivered by a UVC reactor. For high optical transmission solutions, such as water, reactor validation is often performed at scale using the biodosimetry method. However, this method does not measure the range of dose and the dose distribution within the reactor, which are critical parameters for understanding reactor design, operation, and scale-up. Moreover, conducting such studies at scale may require introducing biological contaminants into the very same environment the inactivation technology is intended to protect. This quandary is particularly unacceptable for treatment of low optical transmission solutions in the biopharmaceutical, pharmaceutical and food beverage text owing to regulatory requirements for sanitary processing. Lastly, inactivation measurements using biodosimetry methods tend to pruduce "threshold" results when applied to high stringency inactivation treatments; thus, the true dose received is not known with certainty, only that the dose exceeds a known threshold.

The second method, which is often used in conjunction with biodosimetry, is mathematical modeling. Mathematical modeling employs the Beer-Lambert law along with fluid properties, system geometry, and computational fluid dynamics to estimate the germicidal dose delivered. There are commercially available computer programs to assist in creating such models, e.g., UVCalc® (Bolton Photosciences Inc.) and FLUENT (ANSYS, Inc.). The mathematical models apply mainly to fluids with high transmissions (e.g., water). This method, however, also has a drawback: for applications involving the treatment of highly absorbing (i.e., low transmission) fluids such as cell culture media, the mathematical models have a greater level of inaccuracy owing to non-linear optical absorbance phenomena not embodied in the Beer-Lambert law or other optical absorbance mathematical descriptions. While the mathematical modeling method has the advantage of appropriately describing the UVC received dose as a distribution, absent verification with experimental measurement, the results are deemed theoretical and possibly differ from measured reality.

What is needed, therefore, is a method of accurately measuring the UVC dose delivered to a low transmission fluid, such as cell culture media, and consequently ensuring that a germicidal dose of UVC light is delivered to the fluid.

SUMMARY OF THE INVENTION

A method of determining the dose of UVC light delivered to a sample comprising a low optical transmission complex fluid is provided. In one embodiment the method comprises (a) measuring the fluence rate delivered by a UVC source; (b) generating a standard curve by: (i) contacting a bleachable fluorescence emitter with a low optical transmission complex fluid to form a control mixture; (ii) exposing the control mixture to UVC light for an initial residence time; (iii) obtaining an aliquot from the control mixture; (iv) measuring the fluorescence emitted by the aliquot of (iii); (v) repeating (ii)-(iv) one or more times, wherein the control mixture is exposed to UVC light for a residence time that is longer than the initial residence time; (vi) correlating the fluorescence emitted with the residence time; (c) contacting a bleachable fluorescence emitter with a test fluid comprising a low optical transmission complex fluid to form a test mixture; (d) exposing the text mixture to UVC light for a selected residence time; (e) measuring the fluorescence emitted by the test mixture; and (f) determining the dose delivered to the test mixture using the standard curve of (b). In a further embodiment the UVC light has a wavelength in the range of about 200 nm to about 280 nm. In another embodiment the UVC light has a wavelength of 254 nm. In still a further embodiment the low optical transmission complex fluid comprises cell culture media, serum, a mixture comprising a vitamin, a sugar and a pigment and a colution containing amino acids, peptides or proteins. In another embodiment the bleachable fluorescence emitter comprises a UV-sensitive fluorescent microsphere. In yet another embodiment the UVC source is a NIST traceable VC source. In still a further embodiment, the dose is provided as one of a dose distribution, a mean dose, a P10 dose, a P50 dose and a P90 dose. In another embodiment the fluence rate delivered by the UVC source is measured using a NIST traceable UVC detector.

Also provided is a method of inactivating an organism in a sample comprising a low optical transmission complex fluid known or suspected to comprise an organism. In one embodiment the method comprises (a) identifying a dose of UVC known or suspected to inactivate the virus; and (b) exposing the sample to the inactivating dose of UVC light provided by a UVC source; wherein the inactivating dose comprises a selected wavelength, a selected UVC reactor power and a selected residence time; and wherein the power and irradiation time are determined using a standard curve generated by: (i) measuring the fluence rate delivered by the UVC source; (ii) contacting a bleachable fluorescence emitter with a low optical transmission complex fluid to form a control mixture; (iii) exposing the control mixture to UVC light for an initial residence time; (iv) obtaining an aliquot from the control mixture; (v) measuring the fluorescence emitted by the aliquot of (iii); (vi) repeating (iii)-(v) one or more times, wherein the control mixture is exposed to UVC light for a residence time that is different than the initial residence time; and (vii) correlating the fluorescence emitted with the exposure time. In another embodiment the UVC light has a wavelength in the range of about 200 nm to about 280 nm. In yet another embodiment the UVC light has a wavelength of 254 nm. In still another embodiment the low transmission fluid comprises cell culture media. In still a further embodiment the fluorescence emitter comprises a UV-sensitive fluorescent microsphere. In another embodiment the organism is a spore. In yet another embodiment the organism is a virus. In still another embodiment the organism is a bacteria. In a further embodiment the virus comprises one or more of a dsDNA virus, a ssDNA virus, a dsRNA virus and a ssRNA virus. In still further embodiments the virus comprises one or more of a dsDNA virus, a ssDNA virus, a dsRNA virus and a ssRNA virus; in specific embodiments the virus can comprise a virus of one or more of the virus families adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, Flaviviridae, HEV-like viruses, nodaviridae, picornaviridae, togaviridae, and tertroviridae. In particular embodiments the virus is the parvovirus MVM, the retrovirus MuLV or the bunya virus CVV. In some embodiments the method provides a viral log reduction value (LRV) of greater than or equal to about 0.5., about 1.0, about 1.5, about 2.0, about 2.5, about 3.0, about 3.5, about 4.0, about 4.5, about 5.0, about 5.5, about 6.0, about 6.5 or greater than about 6.5. In another embodiment the method further comprises the step of modifying one or both of (a) the initial power and (b) the initial period such that the mean dose delivered by the UVC reactor is equal to the inactivating dose. In yet other embodiments the UVC source is a NIST traceable UVC source. In another embodiment the dose is one of a dose distribution, a mean dose, a P10 dose, a P50 dose and a P90 dose. In still another embodiment the fluence rate delivered by the UVC source is measured using a NIST traceable UVC detector.

BRIEF DESCRIPTION OF THE DRAWINGS

FIG. 4 is a plot showing the result of a simulation and optimization; FIG. 4A shows results for long exposure times resulting in high UVC dose conditions, while

FIG. 5 is a plot showing the relationship between the standard deviation and the mean for experimental distributions for simulation distribution; FIG. 5A shows the percent error versus fluorescence distribution by dose group, while

FIG. 8 is a plot showing the results of a simulation and optimization; FIG. 8A depicts the cumulative probability distributions for experimental and simulated fluorescence distributions of microspheres treated with process reaction conditions, while

FIG. 18 is a plot showing a comparison of measured fluorescence distributions (dark shade lines) with simulated distributions (light shade lines) produced using optimal bleaching constants; FIG. 18A shows the results for short exposure times producing a low UVC dose experiment versus a simulated distribution, while

FIG. 19 is a plot showing the results of a comparison of measured fluorescence and dose distributions; FIG. 19A shows a comparison of the measured and simulated fluorescence distributions while

FIG. 27 is a plot showing a comparison of measured fluorescence distributions (dark shade lines) with simulated distributions (light shade lines) produced using optimal bleaching constants for exposure of microspheres in SDS solution; FIG. 27A shows the results of a low UVC dose experiment versus simulated distribution, while

FIG. 29 is a plot showing a comparison of measured fluorescence distributions (dark shade lines) with simulated distributions (light shade lines) produced using optimal bleaching constants for exposure of microspheres in Mab FVIP solution; FIG. 29A shows the results of a low UVC dose experiment versus simulated distribution, while

FIG. 31 is a plot showing a comparison of measured fluorescence distributions (dark shade lines) with simulated distributions (light shade lines) produced using optimal bleaching constants for exposure of microspheres in Mab FVIP solution containing tyrosine; FIG. 31A shows the results of a low UVC dose experiment versus simulated distribution, while

DETAILED DESCRIPTION OF THE INVENTION

Figure 1:
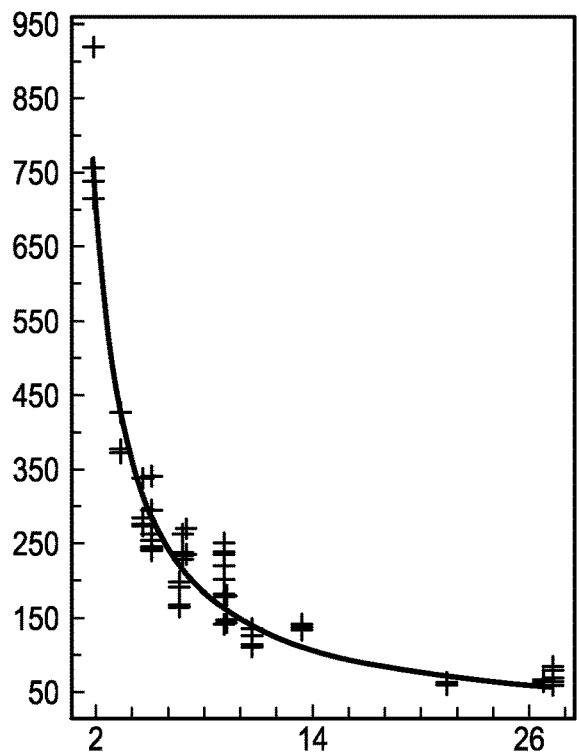
FIG. 1 is a plot showing a global model for mean doses of UVC delivered to media; in the figure fluency is shown as a function of asborbance. X=Absorbance (254 nm). Y=Fluency (mJ/cm2÷minutes). A: 6.329E-05. B: 0.0006764. Equation Y+1/(A+BX). F-test 0.949474.

The instant disclosure provides methods of determining a dose of radiation in the C band of the ultraviolet light range ("UVC," approximately 254 nm) delivered to a low transmission fluid, such as cell culture media, including diluted cell culture media and purified protein solutions. Also provided are methods of treating low transmission fluids with UVC light in order to more effectively inactivate viruses in the fluid. In various embodiments the low transmission fluid is cell culture media, and in other embodiments the virus is a parvovirus.

I. Definitions

As used herein, the terms "a" and "an" mean one or more unless specifically indicated otherwise.

As used herein, the term "dose of UV light" means an amount of energy delivered to a target in the form of UV light. The dose of UV light delivered to a target is a function of intensity and exposure time. A non-limiting list of examples of a "dose of UV light" includes about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 450 mJ, about 500 mJ, about 600 mJ, about 700 mJ, about 800 mJ, about 900 mJ, about 1000 mJ and greater than about 1000 mJ.

As used herein, the term "UV light" means the region of the light spectrum having a wavelength between at least 10 nm and at most 400 nm. By way of example, the term "UV light" encompasses light having a wavelength in the range of about 200 nm to about 280 nm, including a wavelength of about 254 nm. In the methods provided herein, UV light can be delivered in a uniform columnated and filtered fashion; accordingly, both uniform columnated and non-columnated UV are encompassed by the term "UV light," as well as filtered UV light and unfiltered UV light.

As used herein, the term "low optical transmission complex fluid" means a free flowing liquid comprising a solvent and one or more molecular solutes with the property that light intensity is attenuated upon passage through a thickness of the fluid owing to physical absorption of the optical energy. By way of example, the term "low optical transmission complex fluid" encompasses solutions containing water as solvent and carbohydrate and/or amino acids (including peptides and/or proteins) as solutes which attenuates light intensity, when passed through about 1 cm fluid thickness, by a factor of about ten.

As used herein, the term "Water Factor" is a value calculated by the following equation: Water $$\text{Factor} = \frac{1 - 10^{-al}}{al\ln(10)},$$

where a=absorbance of the solution and l is the pathlength in meters.

As used herein, the term "residence time" means the time required for a target to flow from onset of exposure to UVC light to cessation of exposure to UVC light. As individual targets within an ensemble may require different times to traverse the exposure zone of a reactor, owing to their different trajectories, they correspondingly experience different residence times; thus, the ensemble experiences a distribution of individual residence times the mean of which is called the average residence time. In cases of non-flowing targets, the term residence time is synonymous with exposure time and all targets are exposed for the same amount of time.

As used herein, the term "bleachable fluorescence emitter" means a chemical entity which can (1) acquire energy by virtue of absorption of photons of light, transiently retain at least part of that energy in an excited state, and later emit remaining energy as photons of light at a lower energy wavelength of light, and (2) absorb photons of UVC wavelength light and be consequently covalently modified so as to thereafter lose the ability to absorb photons of light. By way of a specific example, a polystyrene particle conjugated with fluorescent molecules, which can absorb light at 340 nm and subsequently emit light at 380, and which can irreversibly lose part of its fluorescence yield upon exposure to higher energy 254 nm UVC light is a bleachable fluorescence emitter.

As used herein, the term "UVC source" refers to any device able to deliver a dose of light in the UVC band of the light spectrum. A UVC source can, but need not, be NIST traceable. A UVC source can be of the helical type or of the laminar flow or thin-film type.

II. Method of Determining the Dose of UVC Light Delivered to a Sample Comprising a Low Optical Transmission Complex Fluid As described herein, various applications rely on UVC as a component of an overall process. Often these processes rely on precise doses of UVC. For example, when inactivating an organism, such as a virus, bacteria or spore, it is important to deliver enough UVC to inactivate the virus, while at the same time minimizing disruption of the milieu in which the organism is located. In another example, when employing UVC to initiate or stop a chemical reaction such as polymerization, it is important to ensure that a UVC dose adequate to initiate or stop polymerization is provided but, again, that the dose does not disrupt other compounds in the sample. In still another example, when inactivating a spore is it important to deliver enough UVC to inactivate the spore, while at the same time minimizing disruption of the milieu in which the spore is located. Accordingly, while the disclosed methods can be employed to determine the dose of UVC light delivered to a sample comprising a high optical transmission fluid, which may or may not be a complex fluid, the methods provided herein will be of particular value in determining the dose of UVC light delivered to a sample comprising a low optical transmission complex fluid.

It is noted that in the context of all of the methods provided herein, the determined dose is a distribution of doses. In other aspects of the instant disclosure, however, the dose can be described in other ways, including a mean dose, a P10 dose, a P50 dose or a P90 dose.

Initially, the fluence rate delivered by a UVC source is measured using a UVC detector. The control dose is then determined as the mathematical product of the residence time and the fluence rate (see Examples 1-4). In one embodiment the UVC detector is a NIST traceable UVC detector. The standard curve, which is generated as described herein, relates the fluorescence yield of the bleachable fluorescence emitter to the control dose it receives.

In one embodiment the method comprises generating a standard curve. The standard curve can account for subtle variations in the UVC source and the calibration of the source. In order to generate a standard curve the following steps can be used. Initially, a bleachable fluorescence emitter is contacted with a low optical transmission complex fluid to form a control mixture. The bleachable fluorescent emitter can be any structure or compound that emits a measureable fluorescent signal and can be bleached by UVC wavelength light. In one embodiment a bleachable fluorescent emitter can comprise a fluorescent fluid, while in another embodiment a bleachable fluorescent emitter comprises a matrix in which a fluorescent compound is embedded or associated therewith. As described in the Examples, a preferred bleachable fluorescent emitter comprises polystyrene beads coated with a fluorescent compound. This particular bleachable fluorescent emitter has the advantage of being readily monitored using readily-available technology, such as a FACS instrument.

Any amount of bleachable fluorescence emitter can be employed in the method, although it is desirable to take into account the volume of the low optical transmission complex fluid when selecting the amount of emitter. Additionally, the detection limits of the instrument used to measure the fluorescence (and consequently the bleaching imparted by exposure to UVC) can form a criterion for selecting an amount of emitter.

An advantage of the disclosed method is its ability to be applied to a sample comprising a low optical transmission complex fluid. While fluids comprising high optical transmission (e.g., water) can be readily studied (see, e.g., Bohrerova et al. (2007)), methods for analyzing samples comprising low optical transmission are not existent. Examples of low optical transmission fluids include cell culture media, serum and mixtures comprising a vitamin, a sugar and a pigment (e.g., a flavinoid), such as juices and vitamin drinks and solutions containing amino acids, peptides or proteins.

A further advantage of the method is that it can be performed on complex fluids, which is not possible using the methods of Bohrerova et al. Examples of complex fluids include cell culture media, serum, a mixture comprising a vitamin, a sugar and a pigment (e.g., a flavinoid), such as juices and vitamin drinks and solutions containing amino acids, peptides or proteins. By way of comparison, in one embodiment a standard fluid (i.e. a non-complex fluid) comprises a solution comprising water and a detergent, such as dosium dodecyl sulfate (SDS).

Having formed a control mixture, the control mixture is exposed to UVC light for an initial period of residence time to deliver a control dose. The conditions of the exposure, including power level, wavelength, etc, can be selected on any basis and can comprise any values. A control UVC source is preferably adapted to be attuned to a range of power levels but consistently delivers a known fluency of UVC radiation of known wavelength so as to deliver a known consistent dose to the entire volume of the control mixture. Preferred UVC source power levels range from about 1 mJ to about 1000 mJ. In specific examples, the UV-C source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 500 mJ, about 600 mJ, about 700 mJ, about 800 mJ, about 900 mJ or about 1000 mJ. Another feature that is desirable for a UV-C source is the ability to switch from a first power level to a second power level either automatically in response to feedback from a monitor or manually by an operator.

A control UVC source is also preferably adapted to consistently deliver UVC light over a range of wavelengths. Preferred wavelengths range from about 200 nm to about 280 nm, which corresponds to the full C band of the UV spectrum. In particularly preferred embodiments the wavelength is about 254 nm. Examples of sources that can be employed in the disclosed method include the Newport Oriel® Flood UVC sources, for example Model 97536 or UVP® sources, for example EL series UV lamps.

After the control mixture has been exposed to the control UVC source for the initial residence time so as to receive a control dose, an aliquot of the control mixture is taken for subsequent analysis of its remaining fluorescence yield. The aliquot can be of any volume, however the aliquot should be large enough to allow for the measurement of the aliquot's fluorescence using whatever apparatus is desired. An aliquot of the control mixture can be taken prior to exposure to UVC to serve as a control sample.

It is noted that the residence time corresponds to the time during which the control mixture is receiving a UVC dose from a control UVC source. As any sort of UVC reactor or source can be employed in the provided methods, the architecture of these sources can vary. Accordingly, it is noted that the residence time in the disclosed methods does not correspond merely to the time the aliquot spends in the reactor itself, but to the time in which is exposed to UVC light, which is referred to herein as the residence time.

Following exposure of the aliquot to UVC light for the initial period of residence time the fluorescence emitted by the aliquot is measured. As described throughout the instant disclosure, the fluorescence can be measured using any convenient apparatus, such as a FACS instrument.

It is noted that the effect of UVC on the bleachable fluorescence emitter will be to bleach the emitter to some degree. Thus, when measuring the fluorescence it is expected that the fluorescence emitted will be decreased to a degree that is inversely related to the exposure time. Stated another way, it is expected that as exposure time increases the fluorescence emitted is decreased.

Continuing with the method, the steps of exposing the control mixture to a control UVC light source for a selected residence time to ensure a control dose, obtaining an aliquot from the control mixture and measuring the fluorescence emitted by the aliquot can be repeated any number of times. It will be appreciated that in generating a standard curve it can be desirable to have as many datapoints as reasonably feasible. Accordingly, 1, 2, 3, 4, 5, 6, 7, 8, 9, 10, 12, 15 or more aliquots can be obtained and measured for fluorescence emission; these datapoints will form the standard curve.

It will be appreciated that each exposure of the control mixture will be of a different residence time than the initial residence time. In many cases the residence times will become progressively longer. It will also be appreciated that it is possible to generate a second control mixture, if shorter residence times are desired, although if this approach is taken it may be desirable to process the data so as to account for the fact that two different control mixtures were employed in the generation of the data.

In the final step of generating a standard curve the fluorescence emitted from the bleachable fluorescence emitters is correlated with the respective UVC dose. In one embodiment this correlation can be done in a pairwise fashion and plotted on a graph with dose on the X axis and the amount of fluorescence read on the Y axis. See Examples 1-4.

After generating a standard curve, a bleachable fluorescence emitter is contacted with a test fluid comprising a low optical transmission complex fluid to form a test mixture. The bleachable fluorescence emitter will be the same emitter as that used to generate the standard curve. The test fluid can be of any composition, with the proviso that the test fluid is a complex fluid. As noted herein, examples of a complex fluid include cell culture media, serum, juices fluids comprising a vitamin, a sugar and a pigment (e.g., a flavinoid), solutions containing amino acids, peptides or proteins, and these fluids cannot be studied using traditional UVC methods that work well for high optical transmission fluids which comprise complex mixtures.

Continuing, the test mixture is exposed to UVC light for a selected residence time. The residence time is preferably, but need not be, a time that is shorter than the longest residence time of the standard curve, but longer than the shortest residence time of the standard curve.

Following exposure of the test mixture to UVC light for the selected residence time the fluorescence emitted by the test mixture is measured. As in the case of the generation of the standard curve, any convenient means of measuring the fluorescence exposure can be employed, such as FACS.

Finally, the dose delivered to the test mixture is determined using the fluorescence yield measured for the control mixture aliquots and the test mixture. In one embodiment, only the mean of the dose distribution is determined by utilizing only the mean of the fluorescence yield data. In a second embodiment, the dose distribution is determined by utilizing the fluorescence yield distribution data; the generalized distribution can be further abstracted using measures of the distribution such as the mean, and select percentiles. The second embodiment utilizes the discrete target UVC dosimetry information obtainable from the preferred bleachable fluorescence emitter, a microsphere conjugated with a bleachable fluorescent molecule. Both embodiments utilize the fact that the dose delivered by the control reactor to the control mixture aliquots are known; thus allowing the unknown dose delivered by the test reactor to the test mixture to be uniquely determined.

In the first embodiment, the unknown dose is determined by a two part method involving the following: (1) creating a standard curve or equation relating the control mixture aliquot mean fluorescence with the received dose, and (2) applying the resulting standard curve or equation to determine the test mixture unknown dose from its know mean fluorescence. Specifically, the mean fluorescent yield measured for the control mixture aliquots is plotted pair-wise against the corresponding control UVc doses delivered. The resulting graphical representation then represents a standard curve which can be utilized in commonly understood ways. Further, the relationship between the control dose and control mean fluorescence represented by the pair-wise data may be generalized by fitting the data using an appropriate continuous mathematical function and statistical optimization methods. The resulting algebraic equation then represents the standard equation which can be used in commonly understood ways including for use in further mathematical manipulations. The mean dose delivered to a text mixture is then determined using the following simple steps: (a) equate the mean fluorescence yield measured for the test mixture to the mean fluorescence yield measured for the control mixture, (b) determine the corresponding control mixture dose by reading the value from the standard curve or solving the standard equation for the desired dose, and (c) equate the test mixture mean dose to the control mixture mean dose determined.

In the second embodiment, the unknown dose distribution is determined by a two-part method involving the following: (1) determining the fluorescence bleaching kinetic parameters which are constituents of a equation relating the control mixture aliquot fluorescence distribution with the received dose, and (2) applying the resulting photo-bleaching equation in a statistical optimization to determine the unknown dose-distribution which optimally predicts the known test mixture fluorescence distribution. Specifically, the fluorescent yield distributions measured for the control mixture aliquots are employed as objective functions in a statistical optimization to determine the fluorescence bleaching kinetic parameters which suitably describe the photo-bleaching phenomena. As all aliquots necessarily follow the same photo-bleaching mechanisms, they correspondingly obey the same mathematical equation and parameters. Thus, the optimization to determine the fluorescence bleaching kinetic parameters simultaneously uses all the fluorescence distribution data obtained from all the control mixture aliquots to determine numerical values for unknown parameters which optimally represent the fluorescence bleaching phenomena. Once known, the fluorescence bleaching kinetic parameters complete the fluorescence bleaching equation. To determine the unknown dose distribution received by the test mixture upon passage through the test reactor, the fluorescence bleaching equation is applied in a statistical optimization routine to optimally predict the fluorescence distribution of the test mixture aliquot. The unknowns in this later optimization are the parameters which complete the dose distribution equation. While any distribution function can in principle be applied in this optimization routine, the preferred distribution function is the three parameter generalized gamma distribution function due to its reliability in converging optimization calculations.

It is noted that any or all steps of the disclosed methods can be carried out manually or by any convenient automated means, such as by employing automated or computer-controlled systems. In some embodiments the entire method can be automated. In other embodiments one or more steps can be automated. For example, the assessment of delivered dose and modulation in response to variations from target dose levels can form a single automated step. In one embodiment the stabilized sample is exposed to a UV light source and is simultaneously monitored for variations from the target dose. If variations from target are detected a control module can modulate the exposure time, exposure wavelength or power of the UV source so that the target dose is achieved. This can be done in real time in a feedback loop-type arrangement.

The disclosed method can be performed at any scale and either as a discrete unit operation or as a continuous connected process. In one embodiment of a discrete unit operation a sample of any volume is formed in a vessel. The vessel is then exposed to UV light (e.g., UVC light) and subsequently an assessment of virus or spore inactivation is performed. The operation can be repeated until any spore or virus present in the sample is inactivated. Alternatively the assessment can be made continuously with the exposure to UV light. Following inactivation of the virus the sample can be transferred to a separate vessel for further processing or packaging.

In another aspect, the disclosed method can be performed on any scale, from bench scale to commercial scale. When performing the method on a commercial scale it may be convenient to split a sample into aliquots and treat each aliquot in parallel. For example, multiple UVC sources can be run in parallel to accommodate large volumes of stabilized sample.

In yet another aspect, the disclosed method can be used to verify the accuracy of predictive methods for dose determination by comparing them with experimentally determined doses. Such a verification procedure has benefit as it increases the assurance of the accuracy of conveniently applied mathematical predictions to UVC treatments in environments which are inconveniently assessed with experimental methods. Such conditions exist for UVC treatments in pharmaceutical manufacturing plants where it is difficult or possibly forbidden to introduce foreign test materials which may contaminate the equipment or environment.

In another aspect, the instantly disclosed method can be used to quantitatively compare the dose delivered by one UVC treatment with a second UVC treatment even which the treatments may differ in many respects including: time, location, reactor design, fluid optical transmission, fluid complexity, and mixture constituents. Such a comparison procedure has value as it allows the performance of UVC treatment in one circumstance to be faithfully replicated in another potentially very different circumstance. Such conditions routinely exist for comparing UVC treatments in pharmaceutical manufacturing plants with treatments in biological laboratories involving infectious agents such as virus, bacteria and mycoplasma.

III. Method of Inactivating an Organism in a Sample

Inactivation of organisms such as spores and viruses is a critical step in the preparation of protein solutions for therapeutic use. Indeed, various regulatory agencies have established standards for virus inactivation and numerous vendors have addressed this problem. Virus and spore inactivation technologies have developed in a number of directions, including filter technology, HTST and UVC technology. While each of these technologies has its strength, each also has its drawbacks as well. In the case of UVC, it has been observed that while it is an effective and efficient approach to inactivating spores and viruses, extended exposure of proteins to UVC light can lead to protein degradation and/or oxidation. Thus, while UVC technology is an effective approach to inactivating spores and viruses, the exposure of a sample comprising a protein to high doses of UVC light can have adverse effects on the protein itself. Accordingly, in one aspect of the instant disclosure a method is provided in which the high doses of UVC required to inactivate a spore or virus in a sample comprising a protein component can be employed, while at the same time reducing or eliminating the potential for damage to the protein itself by tailoring the dose of UVC delivered to the sample to no more than is required to inactivate the spore or virus. Accordingly a method of inactivating an organism such as a spore or a virus in a sample comprising a protein component is provided.

In one aspect, the disclosed methods are directed to the inactivation of spores and viruses that can be unintentionally introduced into samples comprising a protein component. Possible sources of unintentional virus introduction in a protein production process include contaminated raw materials or exposure by manufacturing personnel.

One advantage of the disclosed methods is that they can be employed on any type of virus, and is independent of whether the virus is enveloped or unenveloped. Thus, the method can be applied to double stranded DNA viruses, single stranded DNA viruses, double stranded RNA viruses and single stranded RNA viruses. Examples of virus families, which implicitly include all members of the family, that can be inactivated using the disclosed methods include adenoviridae, asfarviridae, herpesviridae, iridoviridae, papillomaviridae, polyomaviridae, poxviridae, circoviridae, hepadnaviridae, parvoviridae, birnaviridae, reoviridae, arenaviridae, vornaviridae, bunyaviridae, deltaviridae, filoviridae, orthomyxoviridae, paramyxoviridae, rhabdoviridae, arterioviridae, astroviridae, caliciviridae, cornonavirdae, Flaviviridae, HEV-like viruses, nodaviridae, picornaviridae, togaviridae, and tertroviridae. In particular embodiments, which can be particularly relevant to therapeutic protein production processes, viruses that can be inactivated using the disclosed methods include the parvovirus MVM, the retrovirus MuLV or the bunya virus CVV.

Initially a dose of UVC light known or suspected to inactivate an organism is identified. In order to most effectively and efficiently inactivate an organism such as a spore or virus using UVC it is desirable to identify a target dose of UVC that will achieve the desired result. Although the disclosed methods can be performed without optimizing UVC exposure conditions (which collectively comprise a "UVC dose") to the type of spore or virus to be inactivated and the method performed at any convenient UVC dose, the efficiency of the method can be enhanced by identifying a target dose specific to the spore or virus to be inactivated. It is noted that some organisms can share conditions under which they will be inactivated by UVC light, and by selecting appropriate exposure conditions two or more types of organisms (e.g., two or more viruses or two or more spores) can be inactivated in a single operation of the disclosed method. Various studies have been performed to identify the UV sensitivities of various DNA- and RNA-containing viruses. See, e.g., Lytle & Sagripanti, (2005) *J. Virol.* 79:14244-252, and Knipe et al., (2007) *Field's Virology*, Lippincott Williams & Wilkins, which are incorporated herein by reference.

Continuing, the sample comprising a low optical transmission complex fluid known or suspected to comprise an organism is then exposed to UV light provided by a source operating at a selected power level and selected wavelength for a selected residence time. Examples of sources that can be employed in the disclosed method include the Newport Oriel® Flood UVC sources, for example Model 97536 or UVP® sources, for example EL series UV lamps.

A UVC source is preferably adapted to be attuned to a range of power levels. Preferred power levels range from about 1 mJ to about 1000 mJ. In specific examples, the UV-C source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 500 mJ, about 600 mJ, about 700 mJ, about 800 mJ, about 900 mJ or about 1000 mJ. Another feature that is desirable for a UVC source is the ability to switch from a first power level to a second power level either automatically in response to feedback from a monitor or manually by an operator.

A UVC source is also preferably adapted to deliver UVC light over a range of wavelengths. Preferred wavelengths range from about 200 nm to about 280 nm, which corresponds to the full C band of the UV spectrum. In particularly preferred embodiments the wavelength is about 254 nm.

As described herein, the combination of UVC source power and residence time of the sample in the UVC source (i.e., the time for which the sample is exposed to UVC light, as defined herein) needs to be sufficient to inactivate the organism; if the cumulative dose of UVC delivered to the sample is not adequate to fully inactivate the organism it may lead to subsequent complications with the sample. These problems can be compounded when the sample comprises a therapeutic product, such as an antibody or therapeutic protein. Moreover, the calibration of the UVC source provided by the manufacturer can be inaccurate.

Thus, in order to ensure that a sufficient dose of UVC is delivered to the sample the disclosed method provides steps to identify the conditions required for the UVC source to provide such a dose. It is noted that in the context of all of the methods provided herein, the determined dose is a distribution of doses. In other aspects of the instant disclosure, however, the dose can be described in other ways, including a mean dose, a P10 dose, a P50 dose or a P90 dose. It will be recognized that a P10 dose, a P50 dose or a P90 dose is a reflection of the percent of UVC received that falls within the described probability of a desired dose, e.g., a P90 dose includes all doses that fall within 90% of a target dose.

In order to use the standard curve (which is generated as described herein) to relate the fluorescence yield of the bleachable fluorescence emitter to the control dose it receives, the fluence rate delivered by a UVC source is measured using a UVC detector. In one embodiment the UVC detector is a NIST traceable UVC detector. The control dose is then determined as the mathematical product of the residence time and the fluence rate (see Examples 1-4).

Continuing, the follow steps are employed: A standard curve is generated. The standard curve is can account for subtle variations in the UVC source and the calibration of the source. In order to generate a standard curve the following steps can be used. Initially, a bleachable fluorescence emitter is contacted with a low optical transmission complex fluid to form a control mixture. The fluorescent emitter can be any structure or compound that emits a measureable fluorescent signal. In one embodiment a fluorescent emitter can comprise a fluorescent fluid, while in another embodiment a fluorescent emitter comprises a matrix in which a fluorescent compound is embedded or associated therewith. As described in the Examples, a preferred fluorescent emitter comprises polystyrene beads coated with a fluorescent compound. This particular fluorescent emitter has the advantage of being readily monitored using readily-available technology, such as a FACS instrument.

Any amount of bleachable fluorescence emitter can be employed in the method, although it is desirable to take into account the volume of the low optical transmission complex fluid when selecting the amount of emitter. Additionally, the detection limits of the instrument used to measure the fluorescence (and consequently the bleaching imparted by exposure to UVC) can form a criterion for selecting an amount of emitter.

An advantage of the disclosed method is its ability to be applied to a sample comprising a low optical transmission complex fluid. While fluids comprising high optical transmission (e.g., water) can be readily studied (see, e.g., Bohrerova et al. (2007)), samples comprising low optical transmission cannot be studied using the same methodology with any meaningful degree of confidence in the results. Examples of low optical transmission fluids include cell culture media, serum and mixtures comprising a vitamin, a sugar and a flavinoid, such as juices and vitamin drinks, and solutions containing amino acids, peptides, and proteins.

A further advantage of the method is that it can be performed on complex fluids, which is not possible using the methods of Bohrerova et al. Examples of complex fluids include cell culture media, serum, a mixture comprising a vitamin, a sugar and a pigment (e.g., a flavinoid), such as juices and vitamin drinks, and solutions containing amino acids, peptides, and proteins. By way of comparison, in one embodiment a standard fluid (i.e., a non-complex fluid) comprises a solution comprising water and a detergent, such as dosium dodecyl sulfate (SDS).

Having formed a control mixture, the control mixture is exposed to UVC light for an initial period of residence time. The conditions of the exposure, including power level, wavelength, etc, can be selected on any basis and can comprise any values. A UVC source is preferably adapted to be attuned to a range of power levels. Preferred power levels range from about 1 mJ to about 1000 mJ. In specific examples, the UVC source is able to deliver about 1 mJ, about 10 mJ, about 25 mJ, about 50 mJ, about 75 mJ, about 100 mJ, about 125 mJ, about 200 mJ, about 250 mJ, about 300 mJ, about 350 mJ, about 400 mJ, about 500 mJ, about 600 mJ, about 700 mJ, about 800 mJ, about 900 mJ or about 1000 mJ. Another feature that is desirable for a UVC source is the ability to switch from a first power level to a second power level either automatically in response to feedback from a monitor or manually by an operator.

A UVC source is also preferably adapted to deliver UVC light over a range of wavelengths. Preferred wavelengths range from about 200 nm to about 280 nm, which corresponds to the full C band of the UV spectrum. In particularly preferred embodiments the wavelength is about 254 nm. Examples of sources that can be employed in the disclosed method include the Newport Oriel® Flood UVC sources, for example Model 97536.

After the control mixture has been exposure to UVC for the initial residence time an aliquot of the control mixture is taken. The aliquot can be of any volume, however the aliquot should be large enough to allow for the measurement of aliquot's fluorescence using whatever apparatus is desired. An aliquot of the control mixture can be taken prior to exposure to UVC to serve as a control sample.

It is noted that the residence time corresponds to the time the control mixture is receiving a UVC dose. As any sort of UVC reactor or source can be employed in the provided methods, the architecture of these sources can vary. Accordingly, it is noted that the residence time in the disclosed methods does not correspond merely to the time the aliquot spends in the reactor itself, but to the time in which is exposed to UVC light, which is referred to herein as the residence time.

Following exposure of the aliquot to UVC light for the initial period of residence time the fluorescence emitted by the aliquot is measured. As described throughout the instant disclosure, the fluorescence can be measured using any convenient apparatus, such as a FACS instrument.

It is noted that the effect of UVC on the bleachable fluorescence emitter will be to bleach the emitter to some degree. Thus, when measuring the fluorescence it is expected that the fluorescence emitted will be decreased to a degree that is directly related to the exposure time. Stated another way, it is expected that as exposure time increases fluorescence emitted is decreased.

Continuing with the method, the steps of exposing the control mixture to UVC light for a selected residence time, obtaining an aliquot from the control mixture and measuring the fluorescence emitted by the aliquot can be repeated any number of times. It will be appreciated that in generating a standard curve it can be desirable to have as many datapoints as reasonably feasible. Accordingly, 1, 2, 3, 4, 5, 6, 7, 8, 9, 10, 12, 15 or more aliquots can be obtained and measured for fluorescence emission; these datapoints will form the standard curve.

It will be appreciated that each exposure of the control mixture will be of a different residence time that the initial residence time. In many cases the residence times will become progressively longer, although in other cases it may be desirable to obtain a fluorescence measurement from an aliquot having a shorter residence time than the aliquots previously obtained. Alternatively, it is possible to generate a second control mixture, although if this approach is taken it may be desirable to process the data so as to account for the fact that two different control mixtures were employed in the generation of the data.

In the final step of generating a standard curve the fluorescence emitted from the emitters is correlated with the respective UVC exposure times. In one embodiment this correlation can be done in a pairwise fashion and plotted on a graph with dose on the X axis and the amount of fluorescence read on the Y axis. See Examples 1-4.

It is noted that any or all steps of the disclosed methods can be carried out manually or by any convenient automated means, such as by employing automated or computer-controlled systems. In some embodiments the entire method can be automated. In other embodiments one or more steps can be automated. For example, the assessment of delivered dose and modulation in response to variations from target dose levels can form a single automated step. In one embodiment the stabilized sample is exposed to UV light and is simultaneously monitored for variations from the target dose. If variations from target are detected a control module can modulate the exposure time, exposure wavelength or power of the UV source so that the target dose is achieved. This can be done in real time in a feedback loop-type arrangement.

The disclosed method can be performed at any scale and either as a discrete unit operation or as a continuous connected process. In one embodiment of a discrete unit operation a sample of any volume is formed in a vessel. The vessel is then exposed to UV light (e.g., UVC light) and subsequently an assessment of virus or spore inactivation is performed. The operation can be repeated until any spore or virus present in the sample is inactivated. Alternatively the assessment can be made continuously with the exposure to UV light. Following inactivation of the virus the sample can be transferred to a separate vessel for further processing or packaging.

In another aspect, the disclosed method can be performed on any scale, from bench scale to commercial scale. When performing the method on a commercial scale it may be convenient to split a sample into aliquots and treat each aliquot in parallel. For example, multiple UVC sources can be run in parallel to accommodate large volumes of stabilized sample.

IV. Additional Applications of the Disclosed Methods

The methods provided herein will find application in a variety of fields. For example, UVC light can be used to initiate chemical reactions, such as polymerization reactions. In this application it is desirable to provide a dose of UVC that initiates the desired chemical reaction, but does not degrade or harm the other components of the reaction mixture. In order to achieve this goal it is necessary to determine the precise dose of UVC delivered by a given UVC source. This can be accomplished using the methods described in the instant disclosure.

In another application, UVC can be used to inhibit or stop a chemical reaction. Again, it is desirable to provide a dose of UVC that inhibits or stops the chemical reaction, but does not degrade or harm the other components of the reaction mixture. In order to achieve this goal it is necessary to determine the precise dose of UVC delivered by a given UVC source. This can also be accomplished using the methods described in the instant disclosure.

Various references have been provided in the instant disclosure. All references cited herein, including the Examples, are incorporated in their entireties for any purpose.

EXAMPLES

The following examples demonstrate embodiments and aspects of the disclosed methods and are not intended to be limiting.

Example 1

Determination of Mean UVC Dose Delivered by Flow-Through UVC Reactor Treatment

The instant Example describes a method for determining the mean dose delived upon passage of a low transmission complex fluid through a flow-through process reactor. The determination thereof involves creating a standard curve or graph comprised of pair-wise control dose and mean fluorescence data points wherein the control data was created using a control reactor and a control mixture. To assure accuracy, the dose from that exposure was determined by measurement with a NIST traceable UVC sensor in combination with accepted standard calculations.

Materials and Method for Example 1

Fluorescent Microspheres

Two lots of fluorescent F114 polystyrene microspheres from Polymicrospheres (Indianapolis, Ind.) were employed (Lot #1: Catalog number: PS1805-FL14; Excitation/emission: 340/380 nm; 0.2% solids, $8.9 \times 10^8$ microspheres/ml, 1.6 µm mean diameter; Lot #2: Catalog number: D4162R; Excitation/emission: 340/380 nm, 1.0% solids, $4.44 \times 10^9$ microspheres/ml, 1.6 µm mean diameter). The microsphere concentration was determined from percent solids through a calculation obtained from public information provided by Duke Scientific Corporation. The measured effect from UVC irradiation of the fluorescent microspheres was quenching or photobleaching of the dye resulting in a diminished fluorescent intensity (FI) emission.

Analysis of the fluorescent microspheres was conducted using Fluorescent Activated Cell Sorting (FACS), a specialized type of flow cytometry which allows for quantitative recording of fluorescent signals from individual microspheres. The FACS system used was a Dako MoFlo XDP. To block out doublets, irregular particles, and instrument noise from the histogram plots, gates were set to include the most homogeneous population of fluorescent microspheres. Once the gates were established they remained constant for all subsequent samples. For consistency, the number of fluorescent microspheres counted was set to 10,000 for each sample. The data from the dot plots was then plotted on a linear scale where the x-axis reflects the relative fluorescent intensity (0-256) and the y-axis is the number of events (microspheres). From these linear plots the software provided with the FACS instrument was used to calculate fluorescent intensity means for each sample.

Collimated Beam

A collimated beam was used to create the standard curve for analyzing the fluorescent microspheres processed through the Bayer UVivatec UVC reactor. The design of this system is modeled after the Environmental Protection Agency's Water Treatment Guidance document. The system comprises a low pressure mercury lamp (6 watt) from UVP, 2 UVP radiometers, a stir plate and a beaker with a stir bar.

Fluorescent microspheres were spiked into 0.1% SDS and exposed to the UV lamp for set time points. The results from the collimated beam defined the relationship between the dose delivered by the reactor and the change in fluorescent intensity of the microspheres.

Generation of a Standard Curve

Fluorescent microspheres were spiked into cell culture media at a concentration of $1 \times 10^6$ particles/ml. Cell culture media was processed through the UVC reactor and aliquotted samples were taken at residence time intervals. To achieve a longer residence time material was processed multiple times through the system.

These samples were analyzed and a standard curve plotting dose versus exposure time was generated. This standard curve was used to calculate required residence times for desired doses for the given media. The residence times were translated into flow rates based on the reactor volume. The reactor volume, also referred to as the exposure volume, is defined as the space in which fluids are exposed to UVC. For the UVivatec UVC device the exposure volume is 24 mLs.

Calculation of Flow Rate

The flow rate for fluids treated with a UVC device was made. The calculation was based on the absorbance at 254 nm of the fluid being treated as well as the lamp intensity output. The lamp output was measured by the UVC device and reflects the operational integrity of the lamp. For all experiments described in this Example, the UVC lamp had an output of 100%.

FACS Analysis

Fluorescent activated cell sorting (FACS) is a specialized type of flow cytometry which allows for quantitative recording of fluorescent signals from individual microspheres. All samples studied in the instant Example were analyzed at the University of Colorado Cancer Center Flow Cytometry Core, in Aurora, Colo. Two systems were used: the first system was a Dako MoFlo high speed FACS sorter with a coherent 190-C 488 krypton laser. For this system the laser is directed to excite at 350 nm and has a 409/20 nm band pass filter for data collection. The second system was the Dako MoFlo, referred to as the MoFlo XDP. The XDP has a solid state ultraviolet laser for excitation in the UVC range with an emission at 450 nm. The data presented in this Example was generated using the XDP system.

FACS Data Interpretation

At the beginning of each FACS run an untreated control with the fluorescent microspheres in 0.1% SOS was run on the system. To block out doublets, irregular particles, and instrument noise from the histogram plots, were set to include the most homogeneous population of fluorescent microspheres. Once the gates were established they remained constant for all subsequent samples. For consistency, the number of fluorescent microspheres counted was set to 10,000 for each sample. The Fluorescent Intensity mean was calculated from the linear histogram by the FACS software. Each fluorescent intensity mean is recorded from the resultant histogram.

Results and Discussion for Example 1

In order to establish the relationship between the change in fluorescent intensity and the dose delivered to the microspheres a collimated beam device was constructed. The design of this system was based on the Environmental Protection Agency's (EPA) Guidance Manuals, with the exception that the microorganism referenced in the document was replaced with fluorescent microspheres.

The system can work using water as the test fluid, and for these experiments the fluorescent microspheres were spiked into 0.1% SDS.

The equation to calculate the dose delivered in $mJ/cm^2$ based on exposure time (Bolton and Linden, (2003), ASCE, 129(3): 209-215) is as follows:

$$DCB = E_s P_f (1-R) \frac{L}{(d+L)} \frac{(1-10^{-A_{254}d})}{A_{254} d \ln(10)} t$$

where
DCB=UV dose ($mJ/cm^2$)
$E_s$=Average UV intensity (measured before and after irradiating the sample) ($mW/cm^2$)
$P_f$=Petri factor (unitless)
R=Reflectance at the air-water interface at 254 nm (unitless)
L=Distance from lamp centerline to suspension surface (cm)
D=Depth of the suspension (cm)
$A_{254}$=UV absorbance at 254 nm (unitless)
t=exposure time (s)

Prior to each experiment with the collimated beam the lamp was warmed for a minimum of 2 hours. For each experiment the Average UV intensity and Petri Factor were measured. This was accomplished using NIST traceable radiometers. The procedure for these measurements is detailed in the EPA's guidance manual.

For generation of the standard curve 30 mLs of sample containing $1 \times 10^6$ particles/ml of fluorescent microspheres spiked into 0.1% SDS was prepared and the A(254) is measured and recorded. The solution was placed into a beaker and a 1 ml aliquot is removed for each time point on the standard curve. Table A details the calculations performed for each standard curve:

TABLE A

| | | Beads in 0.1% SDS 052407 (start with 30 mL, remove 1 mL at each time point) | | | | | | | | |
|---|---|---|---|---|---|---|---|---|---|---|
| Minutes | Exposure Time (s) | Avg. UV Intensity ($mW/cm^2$) | A254 | $P_f$ | (1-R) | L | d | L/(d+L) | Water Factor* | $D_{CB}$ ($mJ/cm^2$) |
| 6 | 360 | 0.0685 | 0.013216 | 1.00 | 0.975 | 50 | 1.276 | 0.9751 | 0.98083 | 23.0 |
| 12 | 720 | 0.0685 | 0.013216 | 1.00 | 0.975 | 50 | 1.231 | 0.9760 | 0.98150 | 46.1 |
| 18 | 1080 | 0.0685 | 0.013216 | 1.00 | 0.975 | 50 | 1.186 | 0.9768 | 0.98217 | 69.2 |
| 24 | 1440 | 0.0685 | 0.013216 | 1.00 | 0.975 | 50 | 1.141 | 0.9777 | 0.98284 | 92.4 |
| 30 | 1800 | 0.0685 | 0.013216 | 1.00 | 0.975 | 50 | 1.096 | 0.9786 | 0.98351 | 115.7 |
| 36 | 2160 | 0.0685 | 0.013216 | 1.00 | 0.975 | 50 | 1.051 | 0.9794 | 0.98418 | 139.1 |
| 42 | 2520 | 0.0685 | 0.013216 | 1.00 | 0.975 | 50 | 1.006 | 0.9803 | 0.98485 | 162.5 |
| 48 | 2880 | 0.0685 | 0.013216 | 1.00 | 0.975 | 50 | 0.961 | 0.9811 | 0.98552 | 186.0 |
| 90 | 5400 | 0.0685 | 0.013216 | 1.00 | 0.975 | 50 | 0.916 | 0.9820 | 0.98619 | 349.3 |
| 120 | 7200 | 0.0685 | 0.013216 | 1.00 | 0.975 | 50 | 0.871 | 0.9829 | 0.98686 | 466.4 |

The samples were analyzed using the FACS instrument and the resultant fluorescent intensity means were recorded. The shift in fluorescent intensity means from an untreated control to a treated control were calculated, and this shift was referred to as delta FI. The delta FI was then plotted against the calculated doses (Table A). The non-linear response between the dose delivered and the delta FI required the use of fitting software. An exponential growth model was determined to be the best fit.

The reproducibility of the standard curve was tracked over a series of experiments to see the variability of the assay. The standard curve samples were exposed to the UVC lamp with and without a visible light filter. This filter blocked UV light in the visible range and was supplied with the system. Because there is no filter on the Bayer UVivatec® system, this filter was removed to maintain consistency between the devices. The data plotted reflected the reproducibility of the assay as well as the lack of an effect from the light filter. Upon examination of the data, it was concluded that while the standard curves show good correlation from run to run, the standard curve may be repeated for every set of experiments.

Determination of the Dose Delivered to Cell Culture Media

Fluorescent microspheres were spiked into the media to be treated. Untreated controls along with samples from the treatment conditions were analyzed with the FACS instrument and the resultant fluorescent intensity means were recorded. The change in fluorescent intensity (delta FI) from the control was calculated for each treatment and, using the standard curve from the collimated beam, doses were determined. The cell culture media was shown to have an effect on the fluorescent intensity (FI) of the microspheres, whereby the FI signal was increased. Experiments were performed to insure the accuracy of using the delta FI values.

Treated fluorescent microspheres in cell culture media were spun down with a centrifuge and resuspended in 0.1% SDS. It was contemplated that in a protocol for processing samples it may be desirable to include a step comprising removing the fluorescent microspheres from the cell-culture media; this may lead to consistency and better ease of analysis. The FACS instrument can, however, easily plug from samples containing a high level of debris and from samples containing concentrated protein.

The following experiment was performed to test the effect of the media on the delta FI. Fluorescent microspheres were spiked into water and into feed media at a concentration of $1 \times 10^6$ beads/ml. The feed media solution containing fluorescent microspheres was then processed through the UVivatec® reactor. After treatment, a sample of the treated media was centrifuged. Most of the media was removed (a residual amount remained) and the fluorescent microspheres were re-suspended in water. The following samples were assayed: untreated beads in media, untreated beads in water, treated beads in media, centrifuged sample of the treated media in water. The results from the flow cytometer are shown in Table B.

TABLE B

| Sample | Mean Fluorescence Intensity (FI) | Delta FI |
|---|---|---|
| Untreated beads in water | 120.23 | |
| Untreated bead in feed media | 136.20 | |
| UVC treated beads in media | 91.20 | 45.00 |
| UVC treated beads in water (spun sample) | 78.70 | 41.53 |

The results presented in Table B show similar values for FI. Due to the differences in mean FI, the delta values were used for calculating dose.

Determination of Mean Dose Delivered

After determining the inaccuracy of the calculation method, new models were created for a range of absorbance's to encapsulate different types of cell culture media being treated. Fluorescent microspheres were spiked into cell culture media of various compositions for the determination of the dose delivered under various run conditions. Standard curves were created relating the dose delivered with exposure time. The dose delivered was calculated using the standard curve generated by the collimated beam described in the instant Example.

Global Model for Dose Determinations

It was observed that there is noted variability between the various mean doses delivered to the cell culture media studied. Using all of the data collected for each media type, a global model was created to more closely examine the correlations. This global model graphed the absorbance at 254 nm versus the fluency (dose/time) to compare similar absorbance values for comparability. The data (80 data points) was graphed; FIG. 1 shows the results from this compilation.

Based on the equation provided above, a model was created for the UVivatec® UVC reactor. The model is based on a preselected wavelength (e.g., 254 nm) and the desired UVC dose (e.g., ~125 mJ/cm$^2$, a dose adequate to inactivate any virus present in the samples). The number of passes is adjusted to keep the flow rate within the operating parameters of the system (5-20 LPH). For the UVivatech® system set to deliver the desired dose of 125 mJ/cm$^2$ to a cell culture media, the parameters for this instrument were determined to be the following:

TABLE C

| A (254) | Fluency (mJ/cm$^2$/minute) | Desired Dose (mJ/cm$^2$) | Exposure Time (minutes) | # of passes | Flow Rate (LPH) |
|---|---|---|---|---|---|
| 1.82 | 772.5897 | 200 | 0.25887 | 1 | 5.562646 |

This global model was tested with the fluorescent microsphere assay using feed media at full concentration, diluted 2× with water, or with expansion media. The absorbance of each media was entered into the model above, the desired doses were entered, and flow rates calculated. A number of treatment conditions were examined, as shown in Tables D, E and F.

TABLE D

| Fluency | | Total passes required to achieve each fluency | Passes at each rate | Volume | | Flow Rate | Exposure Time | |
|---|---|---|---|---|---|---|---|---|
| J/m$^2$ | mJ/cm$^2$ | | | ml | L | L/hr | min | sec |
| 625 | 62.5 | 5 | 5 | 250 | 0.25 | 6.30 | 1.142857 | 68.57143 |
| 1250 | 125 | 10 | 5 | 240 | 0.24 | 6.30 | 2.285714 | 137.1429 |
| 1875 | 187.5 | 15 | 5 | 230 | 0.23 | 6.30 | 3.428571 | 205.7143 |
| 2500 | 250 | 20 | 5 | 220 | 0.22 | 6.30 | 4.571429 | 274.2857 |

TABLE E

2X Diluted Feed Media:

| Fluency | | Total passes required to achieve each fluency | Passes at each rate | Volume | | Flow Rate | Exposure Time | |
|---|---|---|---|---|---|---|---|---|
| J/m$^2$ | mJ/cm$^2$ | | | ml | L | L/hr | min | sec |
| 624.9 | 62.49 | 3 | 3 | 250 | 0.25 | 7.50 | 0.576831 | 34.60985 |
| 1249.8 | 124.98 | 6 | 3 | 240 | 0.24 | 7.50 | 1.153662 | 69.21969 |
| 1874.7 | 187.47 | 9 | 3 | 230 | 0.23 | 7.50 | 1.730492 | 103.8295 |
| 2499.6 | 249.96 | 12 | 3 | 220 | 0.22 | 7.50 | 2.307323 | 138.4394 |

TABLE F

| | | Total passes required to achieve each fluency | Passes at each rate | Volume | | Flow Rate | Exposure Time | |
|---|---|---|---|---|---|---|---|---|
| Fluency | | | | | | | | |
| J/m² | mJ/cm² | | | ml | L | L/hr | min | sec |
| 625 | 62.5 | 2 | 2 | 250 | 0.25 | 9.80 | 0.293878 | 17.63265 |
| 1250 | 125 | 4 | 2 | 240 | 0.24 | 9.80 | 0.587755 | 35.26531 |
| 1875 | 187.5 | 6 | 2 | 230 | 0.23 | 9.80 | 0.881633 | 52.89796 |
| 2500 | 250 | 8 | 2 | 220 | 0.22 | 9.80 | 1.17551 | 70.53061 |

Dose Determination for Inactivating Virus in Cell Culture Media

A study was performed to determine a treatment regime for UVC-mediated virus inactivation. To determine the treatment regime for media several experiments were executed using the disclosed fluorescent microsphere assay. The target dose was 125 mJ/cm². Table G was used to determine the required exposure time to achieve this dose. The first column denotes the calculated dose for the instrument.

TABLE G

| Dose (mJ/cm²) | FI Mean | Delta FI | Measured Dose (mJ/cm²) | Exposure Time (minutes) |
|---|---|---|---|---|
| 0 | 142.22 | 0 | −5.12 | 0.00 |
| 50 | 107.02 | 33.78 | 53.53 | 0.16 |
| 62.5 | 108.44 | 35.2 | 57.95 | 0.20 |
| 100 | 102.15 | 40.07 | 75.01 | 0.32 |
| 125 | 97.07 | 45.15 | 96.37 | 0.39 |
| 150 | 93.07 | 49.15 | 116.25 | 0.47 |
| 182.5 | 87.01 | 55.21 | 152.53 | 0.59 |
| 200 | 85.4 | 56.82 | 163.61 | 0.63 |

Figure 2:
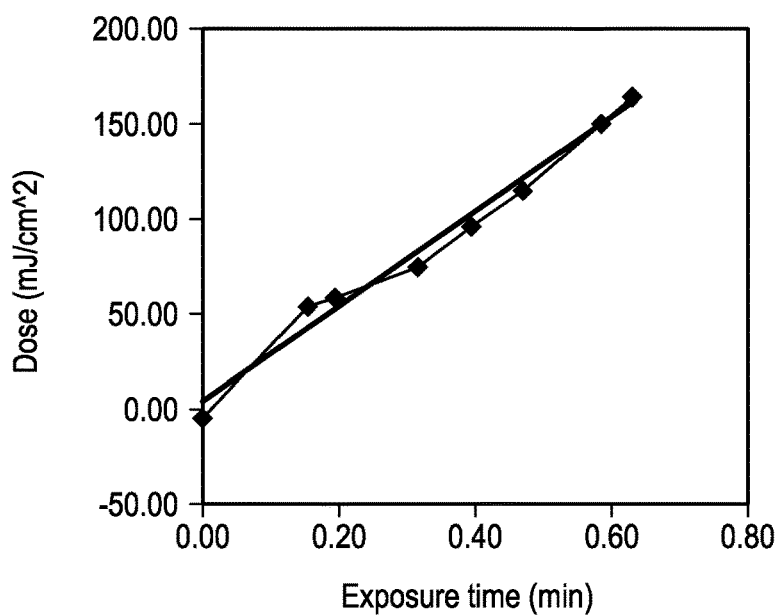
FIG. 2 is a plot showing the relationship of UVC dose to exposure time and the curve used to identify residence time. Solid diamond represents media. Solid line represents linear. y=250.68x+2.0927 $R^2$=0.9848

Entering in a dose of 125 mJ/cm² for y and solving for x the residence time is found to be 0.4916 minutes. See FIG. 2. To achieve this residence time the flow rate is found to be 5.9 LPH, with two passes through the system.

Conclusions from Example 1

The fluorescent microsphere assay developed and described can be implemented to determine the mean dose delivered to cell culture media with varying absorbances, including low transmission fluids such as cell culture media. The disclosed assay provides a method of evaluating UVC reactors regardless of scale or design. Fluorescent microspheres can be spiked into all types of cell culture media and the UVC dose delivered by a given reactor can be accurately determined. This can provide much-needed certainty in the area of virus inactivation and forms a component of various viral inactivation methods.

Example 2

Quantifying UVC Dose Distribution

Having provided methods for determining the mean dose UVC dose and methods of employing UVC light to inactivate viruses and other organisms, it was desired to provide a method of quantifying the dose of UVC provided to a sample, for example a sample comprising a low optical transmission fluid. Accordingly, a deterministic convolution model is provided, which simulates the dose distribution produced with passage through a continuous-flow UVC reactor. The model contains a function to describe the bleaching of fluorescent microspheres and a generalized asymmetric distribution function to describe the dose distribution the microspheres encounter during passage through the reactor. Kinetic parameters contained in the bleaching function were determined by fitting data derived from treating microspheres with an UVC collimated beam device. The dose from that exposure was determined by measurement with UVC sensor (e.g., a NIST traceable sensor) in combination with accepted standard calculations. Parameters within the dose distribution function were determined by fitting the fluorescence distribution produced by passage through a flow-through UVC reactor. Monte-Carlo methods were used to conduct the distribution convolution. An optimization routine was used to automatically identify parameter values which produce the best fit of calculated to measured distributions. Distribution abstracts derived from cumulative distribution curves were used to describe the distribution features in terms which can be used to support reactor design/IQ/OQ/PQ and treatment qualification and validation.

Procedures to quantify dose distributions using fluorescent microspheres have evolved since the approach was first suggested (Anderson (2003)). Some advances stem from research at Duke University (Bohrerova (2005)) and Purdue University (Blatchley (2006)) which utilize different fluorescent bead chemistries and different mathematical deconvolution approaches. Both procedures have been used successfully to support validation of industrial scale UVc systems for secondary water treatment (Linden (2009), Shen (2009)), but have never been used to describe systems comprising a low optical transmission fluid such as cell culture media or solutions containing amino acids, peptides, or proteins.

The instant Example describes a new mathematical approach for quantifying the UVC dose distribution from fluorescent microsphere distribution data based on a deterministic description of the photo bleaching chemistry. While a stochastic approach is used to conduct convolution calculations (the Monte-Carlo method) the equations describing the phenomena are entirely deterministic. In contrast, the primary alternative (Bohrerova (2005)) utilizes a stochastic hierarchal process involving Bayesian statistics, and the Markov chain Monte Carlo integration technique to correlate the microsphere fluorescence intensity distribution to the UV fluence distribution. Deterministic mathematics is generally favored when analyzing data to produce values for inclusion in qualification and/or validation reports in regulated industries.

Materials and Methods for Example 2

Measurement of fluorescent bleaching was performed as described in Example 1. The fluorescence intensity of microspheres treated with the UVC collimated beam and reactors are measured with a digital flow cytometer (FACS). The UVC dose delivered by the collimated beam is calculated based on fluence (intensity), time of exposure/residence time and absorbance at 254 nm, as described in Example 1.
Model Development
Fundamental Physics Photo degradation phenomena are governed by a common physical law, the Reciprocity law, which can be expressed as:

$$\text{Damage} = \int_\lambda \text{function}(\text{Dose}(\lambda))d\lambda$$

$$\text{Dose}(\lambda) = \int_t I(\lambda,t)dt$$

Critical review of the reciprocity law has shown it is uniformly obeyed for biological materials and almost always true for synthetic materials used to produce fluorescent microspheres (Martin (2003)). Low pressure mercury lamps produce essentially monochromatic light at a wavelength of 254 nm so the integration over wavelength is not necessary (EPA (2006)). The practical significance of this law is the degree of damage depends on the dose of radiation and different combinations of intensity and time can yield the same dose. Thus, different microspheres may traverse different paths through the UVC reactor and experience different radiation intensities and residence times but accumulate the same dose and, hence, the same amount of damage. In mathematical terms, the forward calculation (intensity, time to damage) is unique while the reverse calculation (damage to intensity, time) is not unique.
Model of Photobleaching Kinetics Photo bleaching is a photo degradation phenomena wherein there is a loss (or reduction) of fluorescence following exposure to light. The optical and chemical processes involved are complex and involve transitions between a variety of physical and chemical states. Further, these transitions are affected by fluorescent micro environment conditions and can be influenced by microsphere immobilization chemistry and suspending liquid properties (Song (1995), Song (1996), and Song (1997)). Despite this, the rate of photo bleaching generally depends on competition between two interaction mechanisms, Dye/Dye (DD) and Dye/Oxygen (DO), in the absence of quenchers (Song (1996)). With high dye loading on microspheres the DD mechanism predominates (Song (1997)) and the kinetics can be described by a single exponential function reflecting the first-order nature of the reaction. A single exponential function is commonly incorporated to account for photo bleaching in laser induced fluorescence methods used for high accuracy measurement of liquid flow velocity (Crimaldi (1997), Larson (2006)). More generally, a double exponential function is used to describe photo bleaching kinetics, particularly when DD and DO interactions compete (Talhavini (1999)). Photobleaching of microspheres is described herein by the generalized double-exponential function given as:

$$F(\text{Dose}) = F0 * [w_1 * e^{-\text{Dose}*Kb1} + (1-w_1) * e^{-\text{Dose}*Kb2}]$$

F(Dose)=Fluorescence intensity following UVC treatment
F0=Fluorescence intensity prior to UVC treatment
$w_1$=Weighting function for mechanism 1
$Kb_1$=Kinetic constant for mechanism 1
$Kb_2$=Kinetic constant for mechanism 2
Dose=Integrated UVc intensity*time (Reciprocity Law)
Model of Microsphere UVC Exposure with Collimated Beam The fluorescent microspheres utilized for these and other studies are not entirely uniform; that is, each bead is slightly different than the next in terms of particle size and density, fluorophore number and microenvironment, etc. Indeed, different synthesis approaches and even different preparations using the same synthesis can produce suspensions with markedly different spectral and photo-bleaching characteristics (Imhof (1999)). Nonetheless, the microsphere suspension is an ensemble of beads and the attributes and behavior of the ensemble can be reliably described by treating it as a distribution.

In the case of Collimated Beam UVC treatment the dose is uniform (by careful design) and the equation for bleaching (of the ensemble) only contains distribution functions to account for microsphere heterogeneity as follows:

$$\hat{F}(\text{Dose}) = \widehat{F_0} * [w_1 * e^{-\text{Dose}*Kb} + (1-w_1) * e^{-\text{Dose}*Kb}]$$

$\hat{F}(\text{Dose})$=Fluorescence intensity distribution following UVc treatment
$\widehat{F_0}$=Flurosecence intensity distribution prior to UVc treatment The kinetic constants ($w_1$, $Kb_1$, and $Kb_2$) in this case represent overall values and describe the bleaching behavior of the ensemble of microspheres. For a fixed value of Dose and kinetic constants the fluorescence distribution following treatment is a linear transformation of the fluorescence distribution prior to treatment.

$$\hat{F}(\text{Dose}) = \widehat{F_0} * \delta(\text{Dose}) = \widehat{F_0} * \text{constant}$$

$$\text{constant} \leq 1$$

Note that the functional form of the bleaching kinetic equation has a significant effect on the higher moments of the fluorescence distribution. As illustration, let $\hat{F}0$ be a member of the "natural exponential family" (NEF) of distributions (which includes the normal, Poisson, gamma, binomial and negative binomial distributions). Then, $\hat{F}0$ has a quadratic variance function (the variance at the mean is at most a quadratic function of the mean) and linear transformation satisfies the following (Morris (1982)):

$$X(x) \approx X\{\mu, V(\mu)\}$$

$$X'(x) = (X(x)-b)/c$$

$$X'(x) = X'\{\mu', V'(\mu')\}$$

$$\mu' = (\mu-b)/c$$

$$V'(\mu') = V(\mu)/c^2$$

X(x)=Original NEF distribution with mean $\mu$ and variance $V(\mu)$
X'(x)=Linearly transformed distribution with mean $\mu$ and variance $V'(\mu')$
Model of Microsphere UVC Exposure with Flow-Thru Process Reactors During passage through a process reactor individual microspheres are exposed to a spatially varying fluence rate for varying amounts of time. As the damage from UVC radiation follows the law of reciprocity, however, these individual "paths" of exposure need not be considered to determine the dose an individual bead accumulated. Rather, it is sufficient to treat the individual doses as part of an ensemble wherein the properties of the ensemble can be described by a distribution function. Thus, for the process reactor the bleaching equation is represented as follows:

$$\hat{F}(\text{Dose}) = \widehat{F_0} * [w_1 * e^{-\widehat{Dose}*K_1} + (1-w_1) * e^{-\widehat{Dose}*K_2}]$$

$\widehat{Dose}$ = Dose distribution accumulated by microspheres

To utilize the bleaching equation for process reactors it is necessary to convolve the initial fluorescence distribution ($\hat{F}0$) with the dose distribution ($\widehat{Dose}$) to obtain the treated fluorescence distribution ($\hat{F}$(Dose)). Note that the large number of microspheres passed through the reactor sample nearly all trajectories and physically convolve the intensity and time in accordance with the reciprocity law. The mathematical convolution embodied in the bleaching equation must sample a similarly comprehensive space to adequately represent the treated fluorescence distribution.

The bleaching equation for process reactors is deterministic in form (unique F0 and dose values produce a unique F value). Thus, if the initial microsphere fluorescence distribution and dose distribution were known and described by well-behaved analytic functions the treated fluorescence distribution could be analytically determined. In practice, only the fluorescence distributions are known and they are determined by empirical measurement using FACS. To preserve integrity in the analysis it is best to conduct calculations using the empirical fluorescence distributions (represented as "intensity" bins containing fluorescent bead counts). These calculations are conducted using Monte-Carlo numerical methods which simulate the empirical distributions with random sampling and thereby convolve the dose and the initial fluorescence distribution over a comprehensive combination space.

The dose distribution (which is unknown) must be abstracted by a probability density function of some form to conduct the convolution. Several different asymmetric "flexible" distributions were investigated to identify the one which provided the best fit of the simulated and empirically determined final fluorescence distribution. A single functional form for the dose distribution was sought to allow ease of comparison between the different dose distributions produced by different process reactors. The analytic nature of the dose distribution determined is advantageous as it allows statistical inference using rigorous statistical mathematics.

Results and Discussion of Example 2

Simulation of Microsphere Fluorescence Distribution Following UVC Collimated Beam Treatment Fluorescence distribution data was obtained by treating microspheres and analyzing samples as described in materials and methods and summarized in Table H. All data was collected from a single FACS analysis. Simulations were conducted within change-controlled excel spreadsheets and extensively annotated. In Table H BIN Names correspond to BIN data collected by FACS (FACS BIN NAME, Experimental Distribution Name) or produced by simulation calculations (Simulation Distribution Name). The contents of the BINS for FACS BIN and Experimental Distribution are identical.

TABLE H

| Exposure Time (min) | UVc Dose (mJ/cm^2) | FACS BIN Name | Experimental Distribution Name | Simulation Distribution Name |
|---|---|---|---|---|
| 0 | 0 | Control G1:SC = 10000> (G1:SC) | ExpF(T0) | SimF(T0) |
| 1 | 21.08 | T = 1 G1:SC = 10000> (G1:SC) | ExpF(T01) | SimF(T01) |
| 2 | 42.22 | T = 2 G1:SC = 10000> (G1:SC) | ExpF(T02) | SimF(T02) |
| 3 | 63.43 | T = 3 G1:SC = 10000> (G1:SC) | ExpF(T03) | SimF(T03) |
| 4 | 84.70 | T = 4 G1:SC = 10000> (G1:SC) | ExpF(T04) | SimF(T04) |
| 5 | 106.04 | T = 5 G1:SC = 10000> (G1:SC) | ExpF(T05) | SimF(T05) |
| 6 | 127.44 | T = 6 G1:SC = 10000> (G1:SC) | ExpF(T06) | SimF(T06) |
| 7 | 148.91 | T = 7 G1:SC = 10000> (G1:SC) | ExpF(T07) | SimF(T07) |
| 15 | 319.59 | T = 15 G1:SC = 10000> (G1:SC) | ExpF(T15) | SimF(T15) |
| 20 | 426.77 | T = 20 G1:SC = 10000> (G1:SC) | ExpF(T20) | SimF(T20) |
| 25 | 534.28 | T = 25 G1:SC = 10000> (G1:SC) | ExpF(T25) | SimF(T25) |

Figure 3:
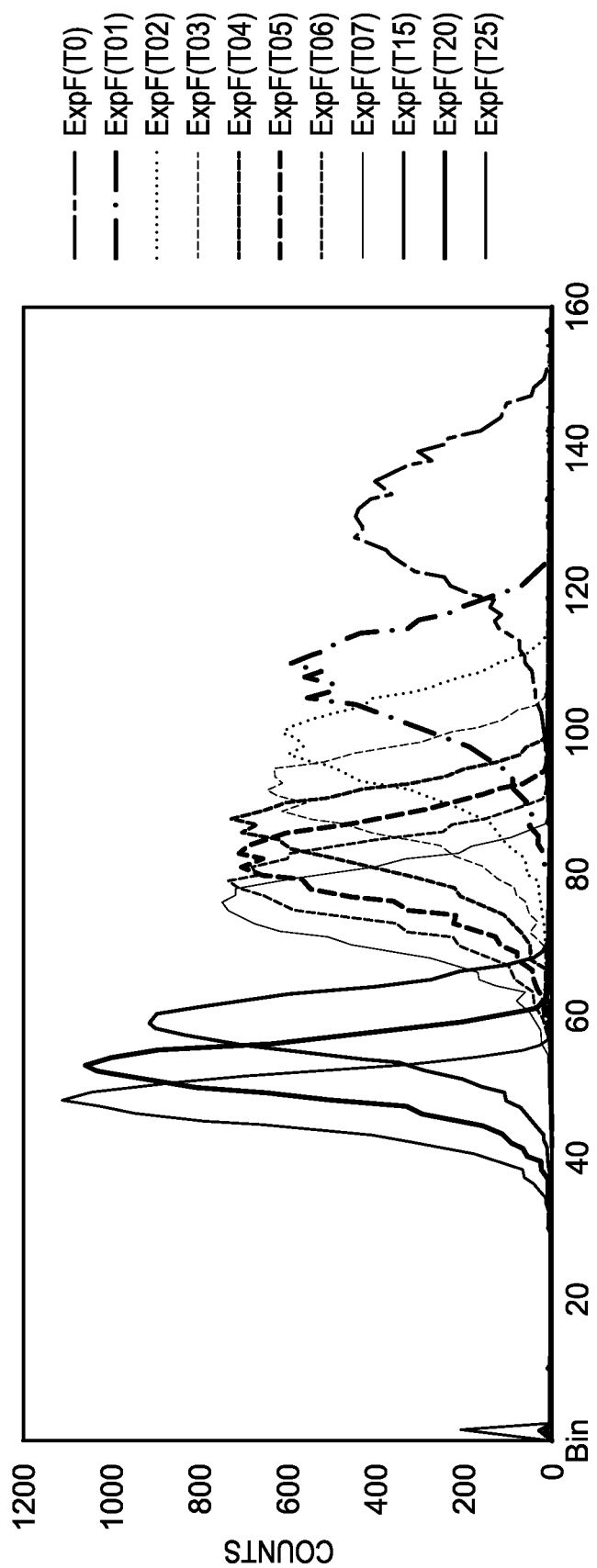
FIG. 3 is a plot showing microsphere fluorescence distribution resulting from several different exposure times as measured by FACS.

UVC treatment of microspheres results in a dose dependent change in the fluorescence distribution as shown in FIG. 3. Qualitatively, it was observed that the mean fluorescence decreases with increasing dose and the distribution becomes increasing sharp with increasing dose. Quantitatively, the change is more complex in that treatment affects the fluorescence distribution mean, variance, and asymmetry.

The fluorescence bleaching results shown in FIG. 3 were used to determine the magnitude of the microsphere photo bleaching kinetic parameters w1, Kb1, and Kb2. This was accomplished by conducting a Monte-Carlo simulation and optimization. The objective of the optimization was to match the experiment and simulation distribution means for a sample treated with approximately 125 mJ/cm$^2$ dose. Additional requirements for acceptable solutions were placed at approximately equally spaced intervals from the midpoint of the fluorescence span (50%+/−6%, and 50%+/−15%)—the experimental and simulation distribution means of these four distributions were specified to be within 2 FU of each other in acceptable solutions. To satisfy the optimization objective and requirements, the values of the bleaching kinetic parameters were assigned as decision variables and automatically varied within limits until the best combination of values was obtained. A typical simulation (inner loop) and optimization (outer loop) entailed the following:

1. Assume initial values for $w_1$, $Kb_1$, and $Kb_2$;

2. Calculate 1e4 values for SimF(x) from 1e4 values of ExpF(0), constant w1, Kb1, Kb2 a. Determine the means of SimF(x) distributions b. Compare the means of SimF(x) and ExpF(x) for objective and requirements c. Determine if difference of means is within allowed tolerance; if yes, solution is allowed 3. Assume new values for w1, Kb1, and Kb2 using proprietary goal seeking algorithms a. Return to step 2; repeat sequence until 1e3 combinations of w1, Kb1, Kb2 are tested 4. At end of sequence calculate statistics of allowed solutions and identify best solution.

An illustration of output shown in Table I:

TABLE I

| Statistics | Mean = 77.6 SimF(T06) | Mean = 83.0-87.0 SimF(T04) | Mean = 72.0-76.0 SimF(T07) | Mean = 56.0-60.0 SimF(T15) | Mean = 44.0-48.0 SimF(T25) | Kb1 | Kb2 | w1 |
|---|---|---|---|---|---|---|---|---|
| Minimum | 77.8 | 83.0 | 75.4 | 59.4 | 44.0 | 4.45E−02 | 1.37E−03 | 2.84E−01 |
| Mean | 77.8 | 83.1 | 75.5 | 59.5 | 44.1 | 4.89E−02 | 1.39E−03 | 2.85E−01 |
| Maximum | 77.8 | 83.2 | 75.5 | 59.7 | 44.4 | 5.14E−02 | 1.40E−03 | 2.87E−01 |
| Std. Dev. | 6.26E−03 | 7.58E−02 | 6.83E−03 | 8.11E02 | 1.44E−01 | 2.43E−03 | 8.79E−06 | 1.04E−03 |
| | Objective | | Requirements | | | Decision Variables | | |

Figure 4A:
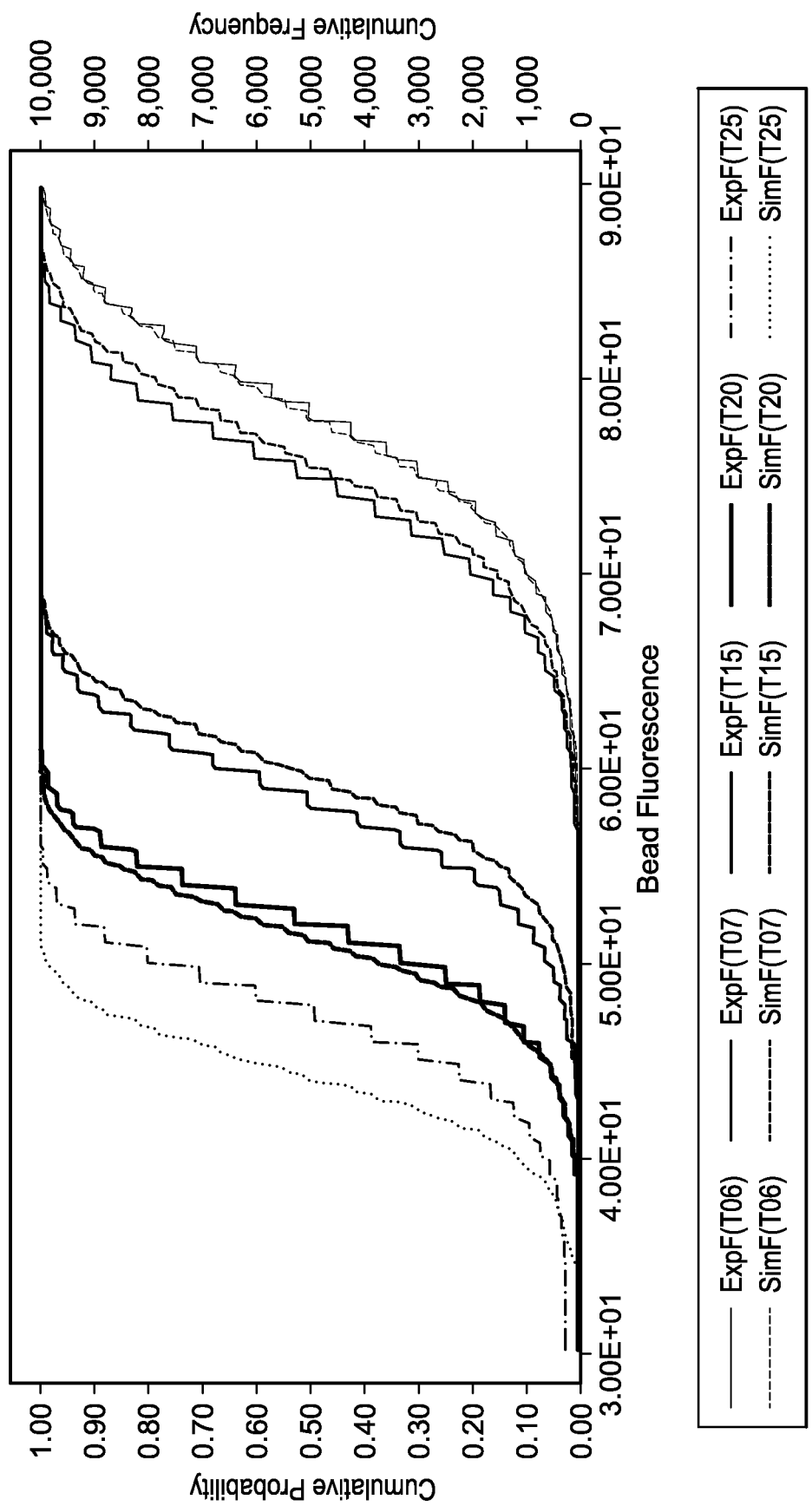
Figure 4B:
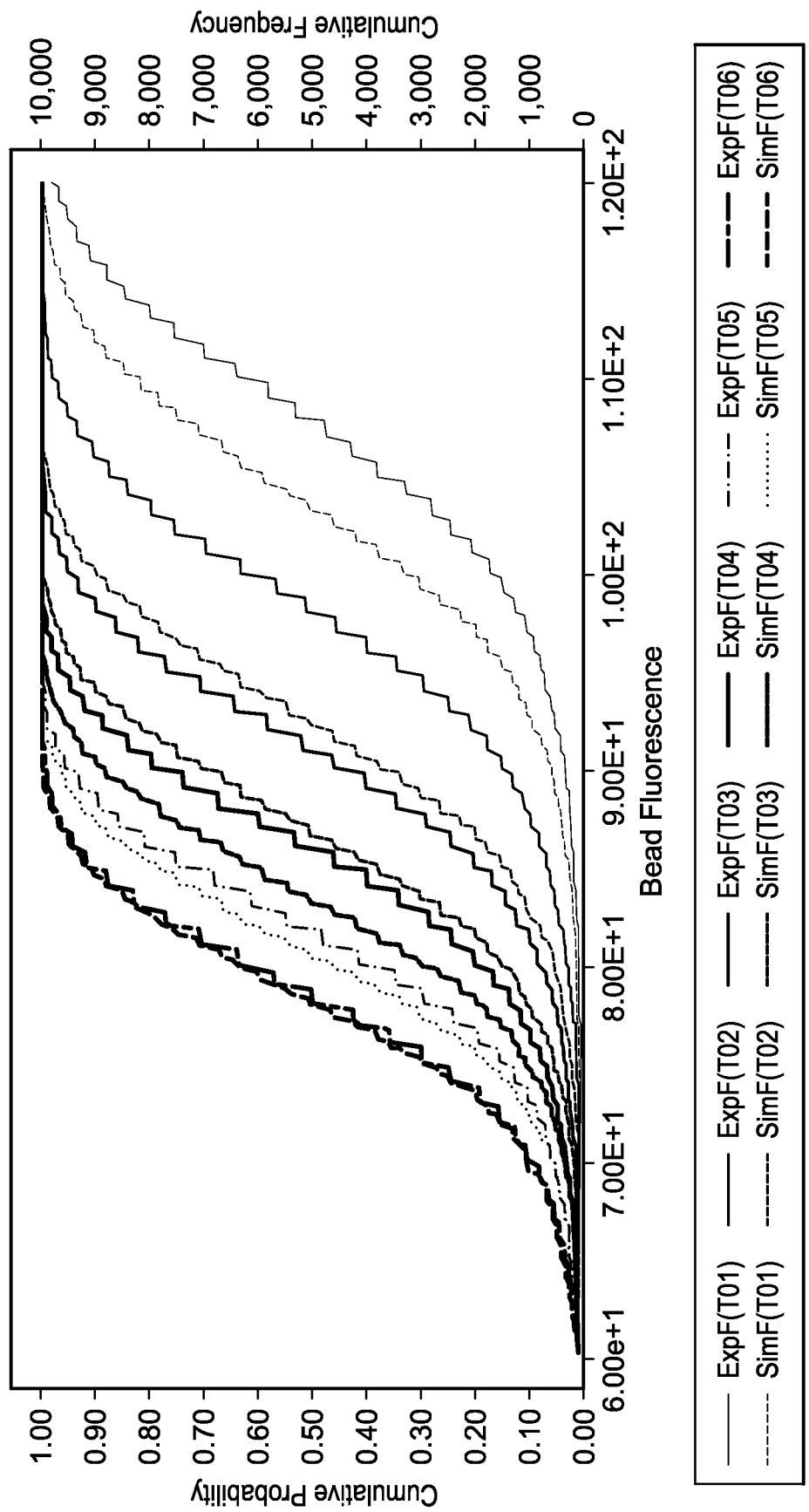
FIG. 4B shows results for short exposure times resulting in low UVC dose conditions.

The result of a simulation and optimization using the above approach is shown in FIGS. 4A and B. FIG. 4A shows results for long exposure times resulting in high UVC dose conditions, while FIG. 4B shows results for short exposure times resulting in low UVC dose conditions. The graphs depict the cumulative probability distribution for all simulation and corresponding experimental distributions. Experimental distributions appear more "step-wise" due to the more limited resolution of experimental bins. Similar colors are used to illustrate corresponding SimF(x) and ExpF(x) cumulative distributions to facilitate visual comparison. From FIGS. 4A and B it was apparent that distributions used to define objectives and requirements have the best fits as expected.

Figure 5A:
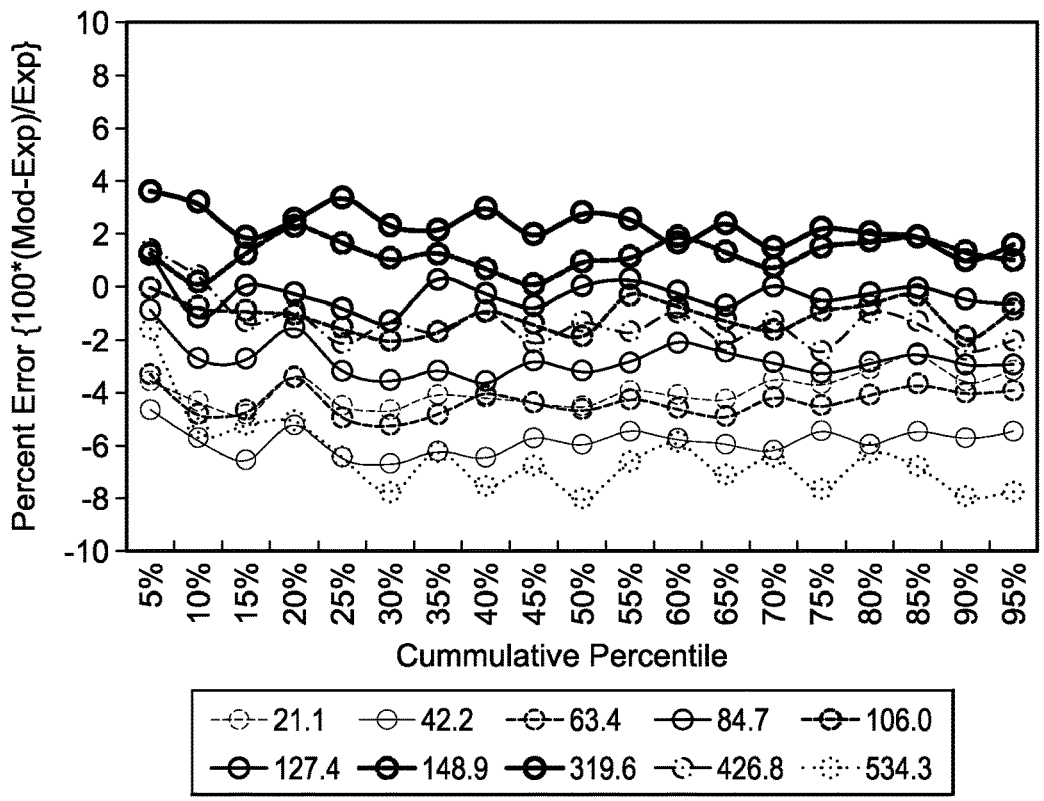
Figure 5B:
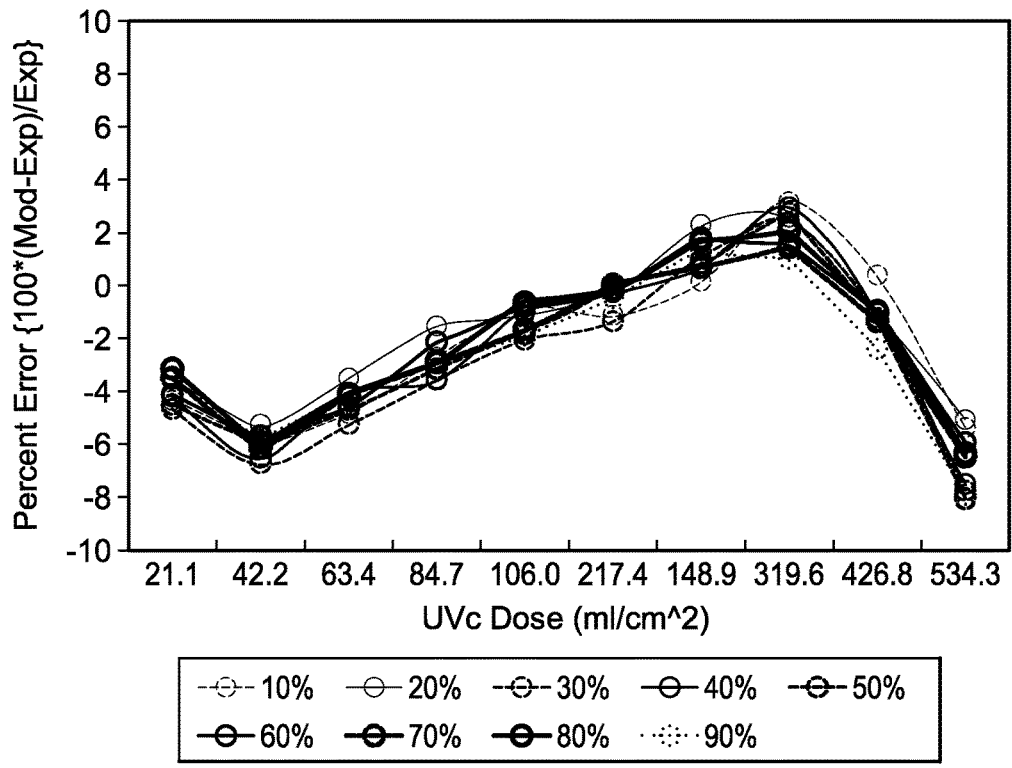
FIG. 5B shows the percent error versus UVC dose by fluorescence distribution cumulative percentile group.
Figure 6:
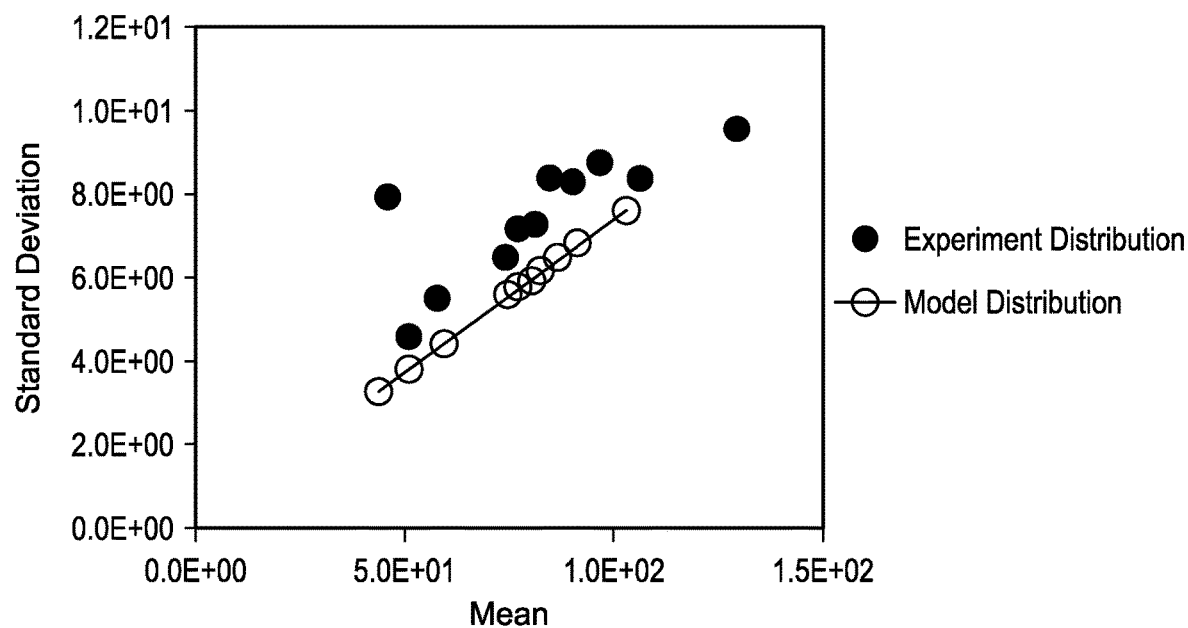
FIG. 6 is a plot showing the correlation between experiment and model fluorescence distribution mean and standard deviation. Solid circle represents experimental distribution. Open circle represents model distribution.

The quantitative accuracy of the simulations is best seen in FIGS. 5A and 5B which depicts the percent error of the simulation by relative position on distribution (cumulative percentile) or by treatment dose. Interestingly, the error does not systematically depend on the position on the distribution. That is, the simulation accurately transforms the shape of the distribution (i.e., variance and asymmetry) which occurs with dose dependent bleaching. The percent error of the simulation does depend systematically on the treatment dose—not surprisingly, the greatest accuracy occurs in the vicinity of the target dose (which was the objective of optimization). Nonetheless, fluorescence simulation accuracy of within approximately 4% is obtained for doses ranging from ~85 to ~320 mJ/cm$^2$. This range brackets well beyond the expected dose distribution range associated with the intended process reactor treatment. The finding that the simulation accurately transforms the shape of the fluorescence distribution has important implications. Note that the optimization involved with the simulation does not include distribution shape in any way—rather, the fit only involves use of the distribution mean. Thus, the transformation of distribution shape is a natural property of the form of the bleaching equation, not the values of the equation parameters. More specifically, the bleaching equation is a linear transformation of the untreated fluorescence distribution. Since the simulation transformation matches the experimental transformation, this implies that the bleaching chemistry is itself a linear transformation. Further evidence to support this general interpretation is shown in FIG. 6 where it is seen that the relationship between the standard deviation and the mean for experimental distributions parallels that for simulation distributions. Such a relationship is expected and described in the model development section of the instant Example.

FIG. 5A shows the percent error of fluorescence distribution simulation versus cumulative percentile of distribution, while FIG. 5B shows the percent error of fluorescence distribution simulation versus UVC does delivered by collimated beam treatment. FIG. 6 shows the correlation between experiment and model fluorescence distribution mean and standard deviation.

Simulation of Microsphere Fluorescence Distribution Following UVC Process Reactor Treatment Experiments were conducted with several different reactor types and media properties as shown in Table J.

Differences in the reactor design are expected to influence the dose distribution predominantly by affecting the "exposure" time experienced by the individual microspheres. Differences in the absorbance of the media are expected to influence the dose distribution by attenuating the intensity of the fluence field along the path-length of the radiation. Multiple passes through a reactor are expected to influence the dose distribution through both mixing (between the separate passages) and the exposure time.

A reactor possessing perfect mixing would ensure all microspheres experienced the same time in all the fluence rate environments present in the reactor—practically, it would deliver a dose similar to the collimated beam. Such a reactor does not exist but is approximated by a helical reactor which uses a spiral flow path around a circular cylinder to induce Dean vortices which continually mix along the radial dimension (labeled R2 in Table J). A reactor possessing no mixing would ensure that all microspheres experienced laminar flow along streamlines within the reactor—each streamline would correspond to a specific dose (integral of fluence rate and time) but those doses would not be unique (due to the reciprocity law). Such a reactor is approximated by the thin-film design (labeled "R1" in Table J) which provides flow through the annular space between two similarly sized circular cylinders.

TABLE J

| | [DATA LABEL] | | |
|---|---|---|---|
| | | Media Absorbance | |
| Reactor | 0.3 | 0.7 | 2.1 |
| R1 1 pass | R1 3AU | R1 7AU | R1 1AU |
| R2 1 pass | R2 0.3AU | R2 0.7AU | R2 2.1AU |
| R2 2 pass | R2 Pas.0.3AU | R2 2pas.0.7AU | R2 2pas2.1AU |

Figure 7:
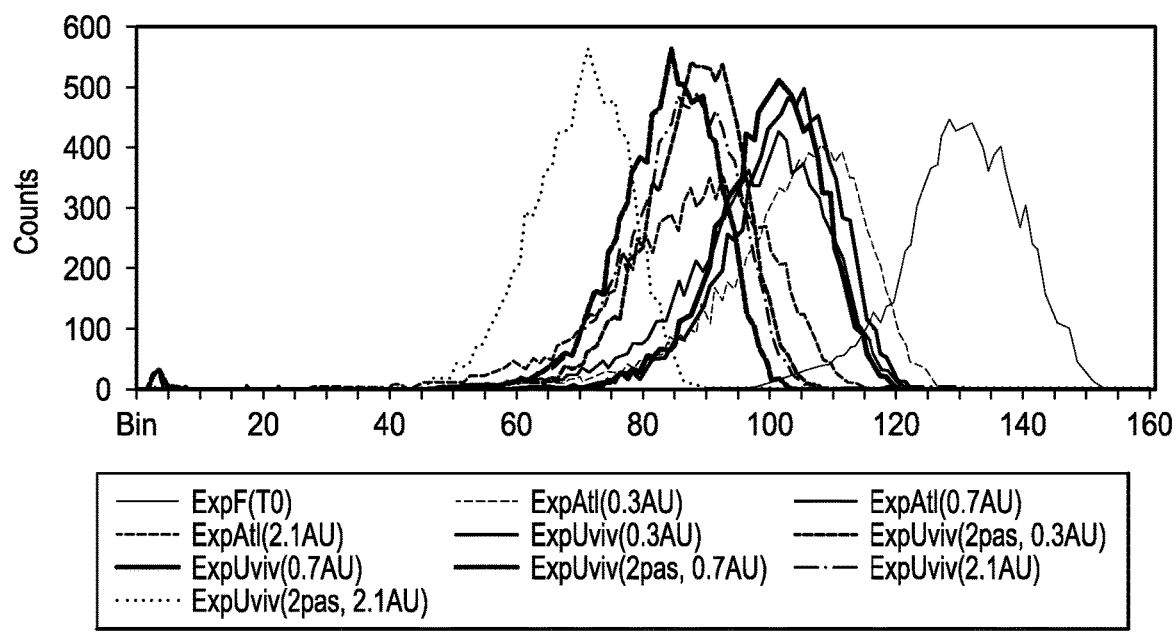
FIG. 7 is a plot showing microsphere fluorescence distribution by FACS versus process reactor treatment; R1=Reactor 1; R2=Reactor 2.

Treatment with the process reactors produces qualitatively different distributions than seen with the collimated beam as shown in FIG. 7. In FIG. 7, and in Table J, R1 refers to thin-film UVC reactor 1 and R2 refers to a helical UVC reactor. More specifically, the distributions do not "sharpen" with decreasing fluorescence to the degree seen with the collimated beam. Such behavior is expected since the dose delivered is a distribution so the bleaching phenomenon is no longer a linear transformation of the fluorescence distribution. Of practical significance, the dose delivered by a process reactor is essentially unknown since it is a distribution describable by numerous distribution abstracts. Similarly, it is not possible to make a single measurement within the reactor to determine the dose distribution. One must make many measurements at many locations to infer the dose distribution—this is precisely what the fluorescent microspheres do during passage through the process reactor.

To accomplish simulation of fluorescence distribution transformation with passage through a process reactor it is necessary to convolve the untreated microsphere fluorescence distribution with the dose distribution. The physical counterpart occurs because the microspheres randomly sample trajectories through the reactor; trajectories are independent of the untreated microsphere fluorescence. To simplify the computation and provide a systematic means to compare the distributions produced with different reactor and media configurations, the dose distribution was abstracted by use of several well known asymmetric probability distribution functions. These included the Generalized Gamma Distribution, the Lognormal Distribution, and the Weibull Distribution.

The fluorescence bleaching results from process reactors were used with the bleaching parameters determined from collimated beam treatment to determine the values of the dose distribution parameters for the respective asymmetric probability distribution function. This was accomplished by conducting a Monte-Carlo simulation and optimization. The objective of the optimization was to match the experiment and simulation fluorescence distribution mean. Additional requirements for acceptable solutions were placed at opposite extremes of the fluorescence probability distribution function (10-Percentile and 90-Percentile)—the experimental and simulation distribution abstract values for these two parameters were specified to be within 2 FU of each other in acceptable solutions. To satisfy the optimization objective and requirements, the values of the dose distribution parameters were assigned as decision variables and automatically varied within limits until the best combination of values was obtained. A typical simulation (inner loop) and optimization (outer loop) entails the following:

1. Assume initial values for dose distribution location, scale, and shape (or equivalents)
2. Calculate 1e4 values for SimF(z) from 1e4 values of ExpF(0): constant location, scale and shape (meaning constant dose distribution for condition=z)
   a. Determine the mean, 10-Percentile, and 90-Percentile of SimF(z)
   b. Compare the mean, 10-Percentile, and 90-Percentile of SimF(z) and ExpF(z) for objective and requirements.
   c. Determine if differences are within allowed tolerance; if yes, solution is allowed
3. Assume new values for dose distribution location, scale, and shape (or equivalents)
   a. Return to step 2; repeat sequence until 1e3 combinations of location, scale, and shape are tested
4. At end of sequence calculate statistics of allowed solutions and identify best solution.

An illustration of the output of the simulation is shown in Table K:

TABLE K

| Statistics | Mean = 103.0 SimR1 (0.3AU) | 10% Percentile 84.0-90.0 SimR1 (0.3AU) | 90% Percentile 113.0-119.0 SimR1 (0.3AU) | G Location | G Scale | G Shape |
|---|---|---|---|---|---|---|
| Minimum | 103.0 | 88.4 | 114.9 | 9.181E−01 | 3.020E+01 | 1.000E−01 |
| Mean | 103.0 | 88.5 | 118.4 | 1.062E+01 | 3.546E+01 | 4.038E−01 |
| Maximum | 103.0 | 89.5 | 118.8 | 2.605E+00 | 1.00E+02 | 4.300E−01 |
| Std. Dev. | 1.35E−03 | 2.48E−01 | 9.25E−01 | 4.116E−01 | 1.717E+01 | 8.121E−02 |
| | Objective | Requirements | | Decision Variables | | |

Figure 8A:
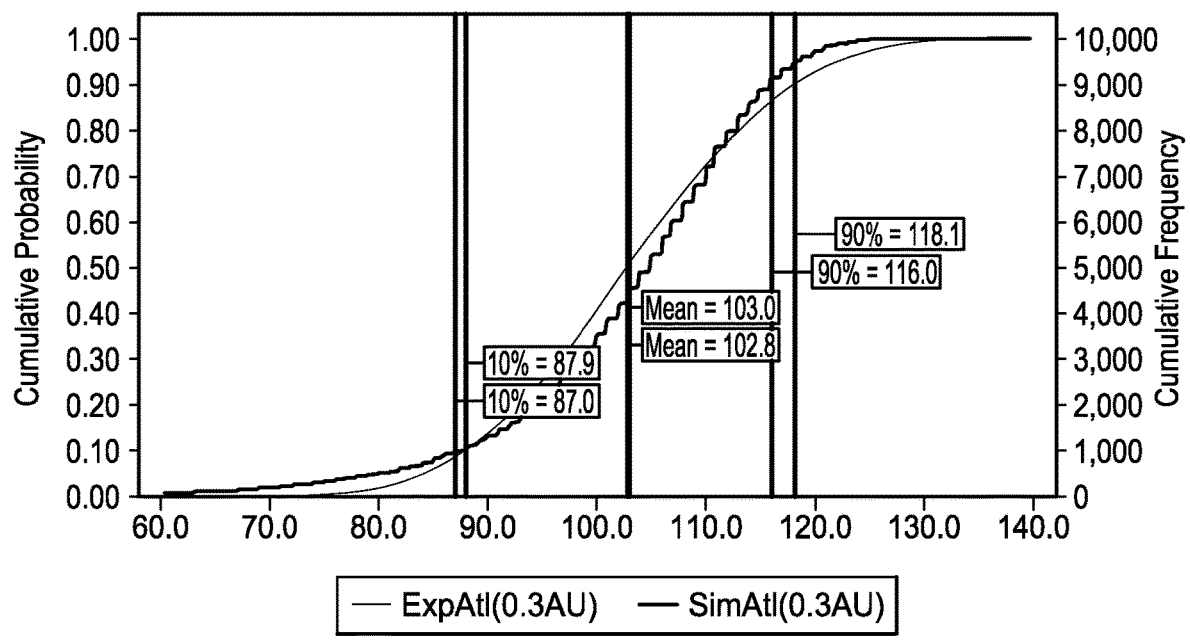
Figure 8B:
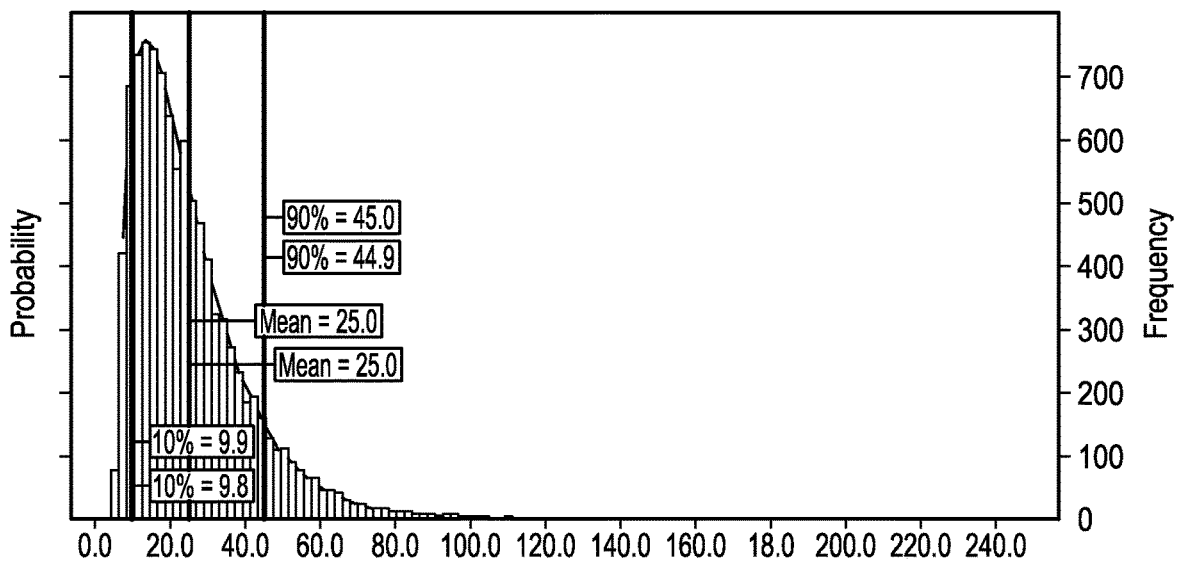
FIG. 8B shows the simulated does distribution
Figure 9A:
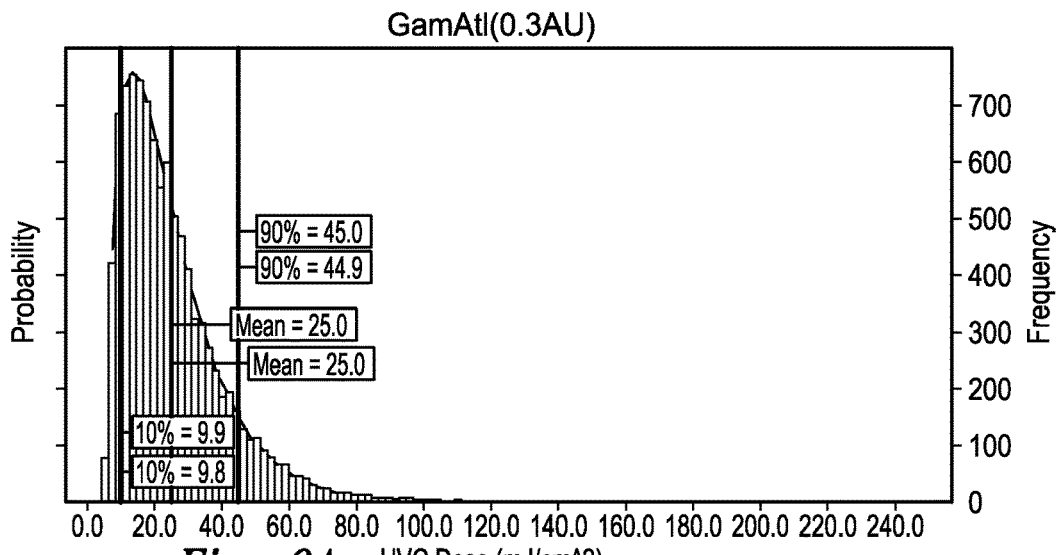
FIG. 9 is a series of plots showing dose distribution predictions for a thin-film reactor.
Figure 9B:
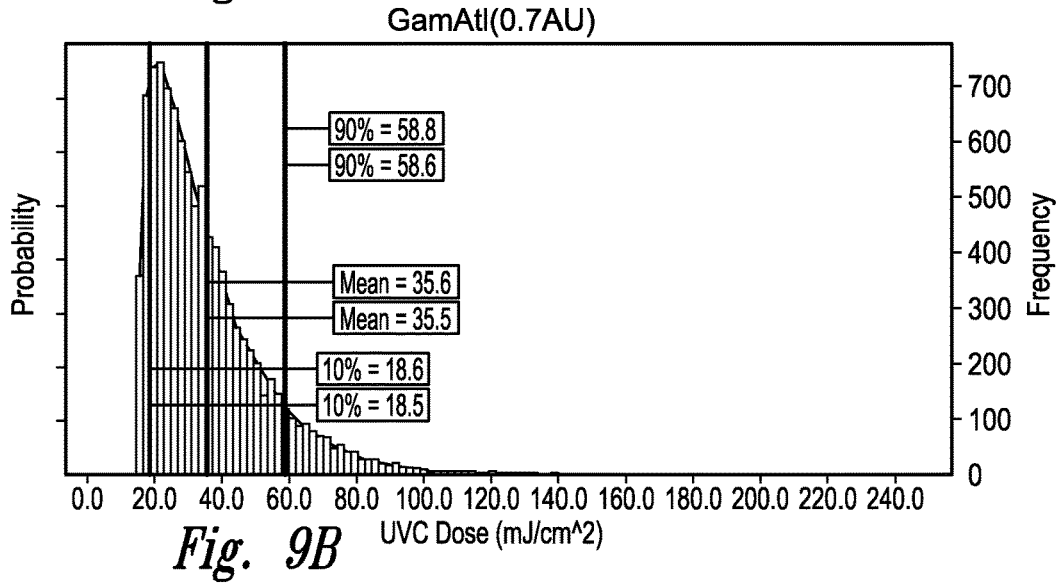
Figure 9C:
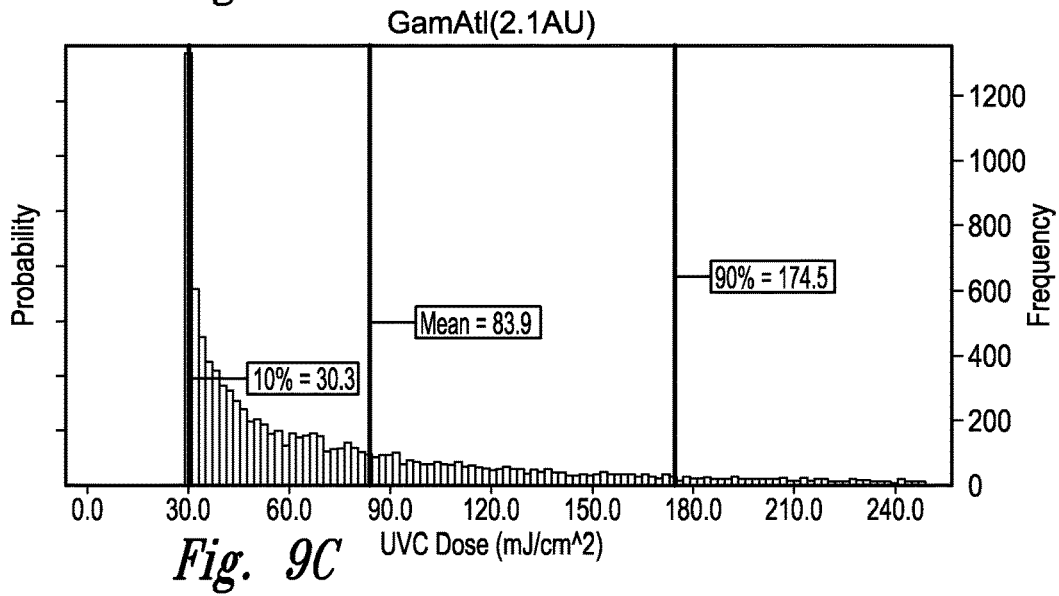
Figure 9D:
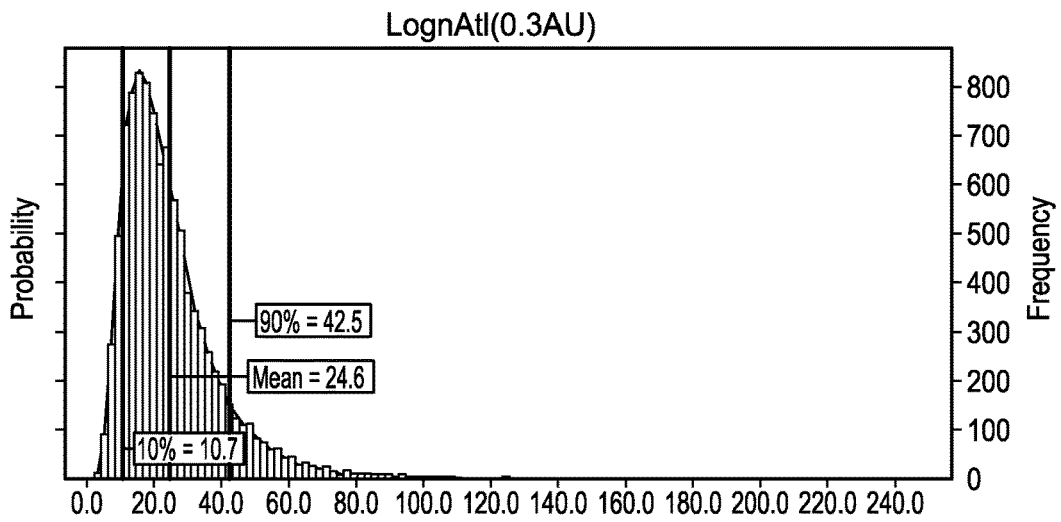
Figure 9E:
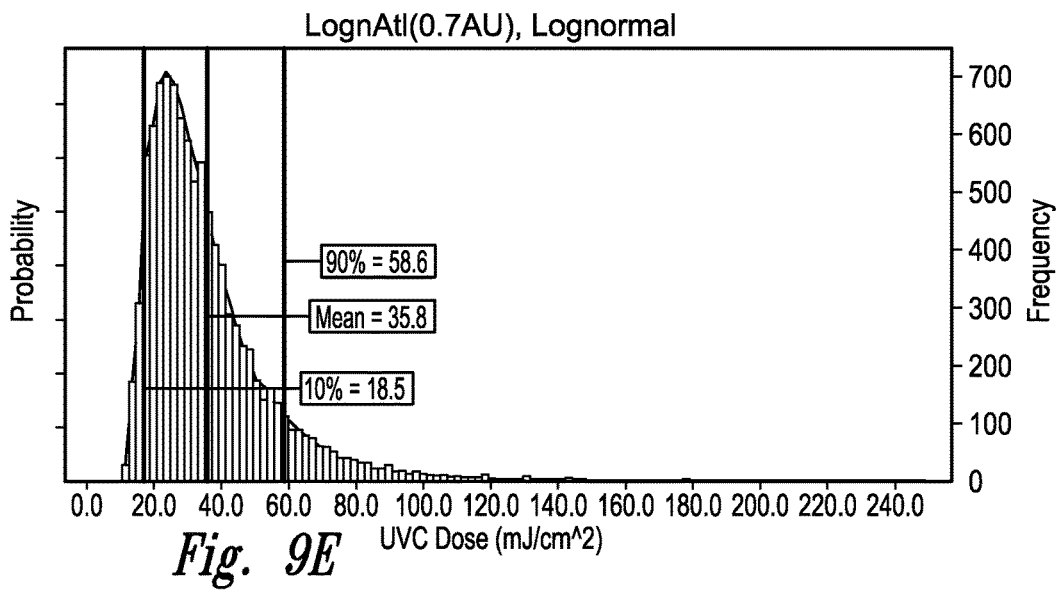
Figure 9F:
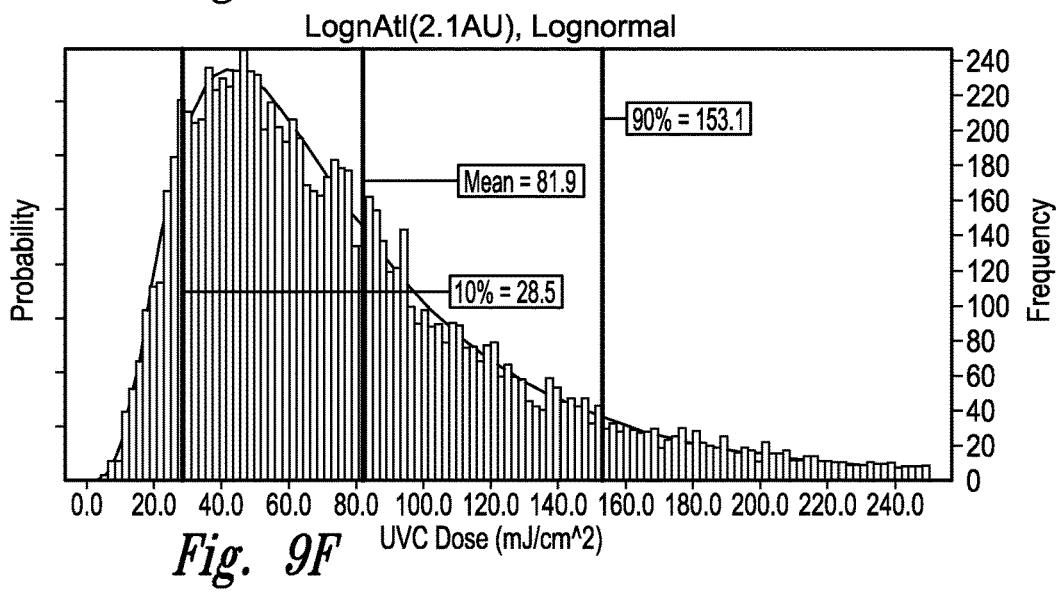
Figure 9G:
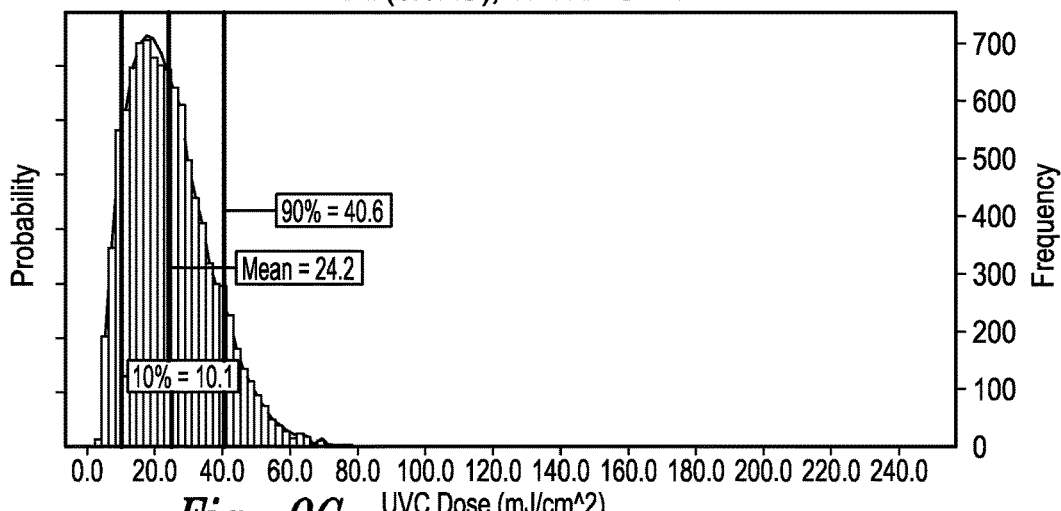
Figure 9H:
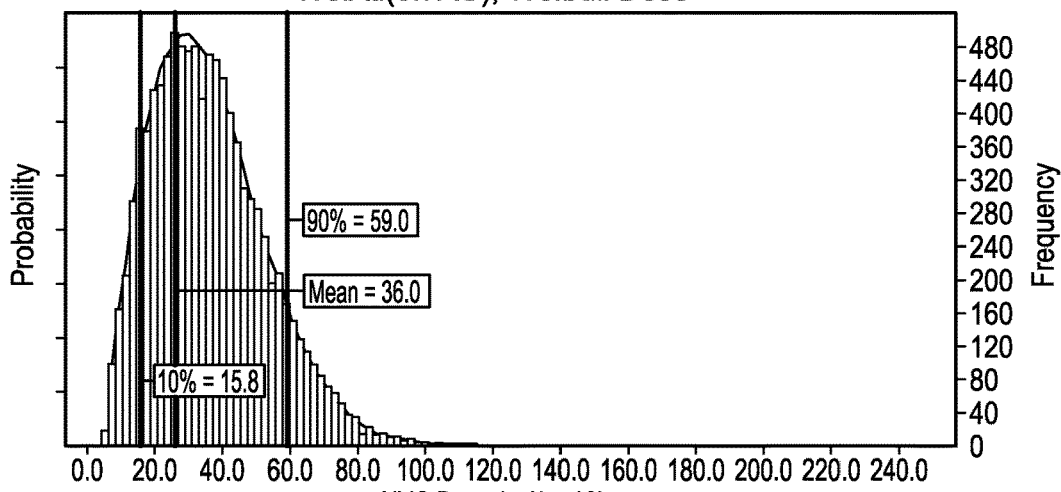
Figure 9I:
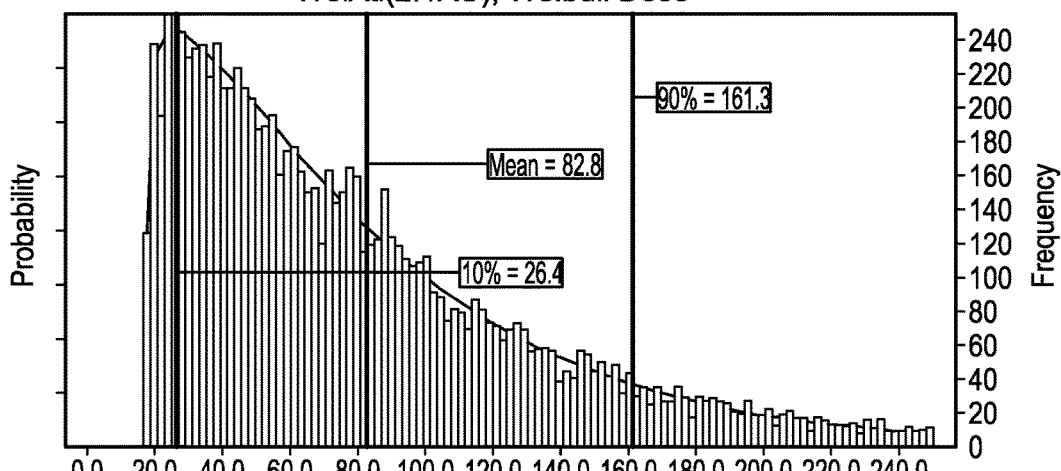
Figure 10A:
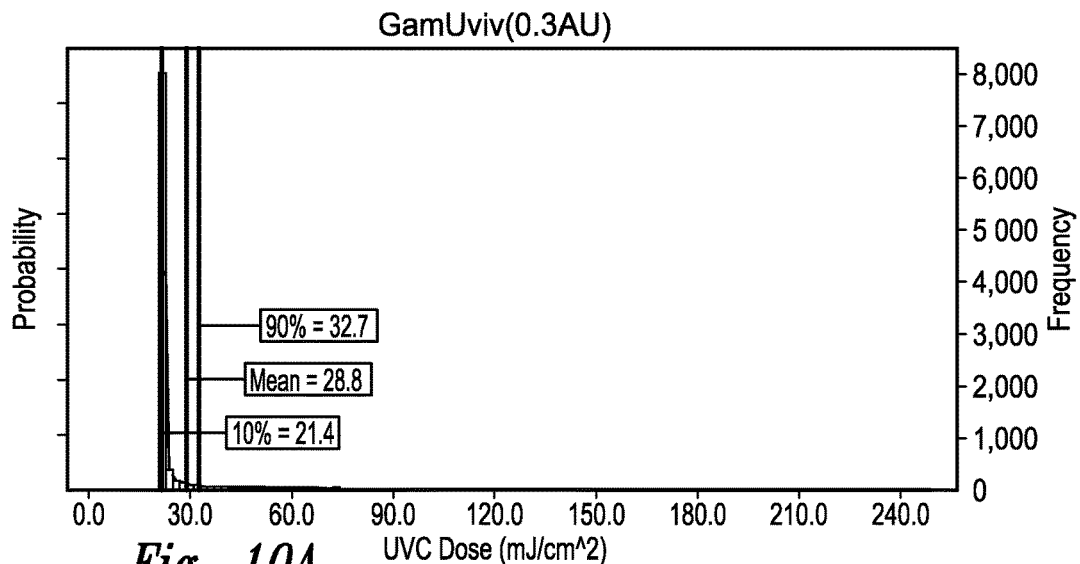
FIG. 10 is a series of plots showing dose distribution predictions for a helical reactor.
Figure 10B:
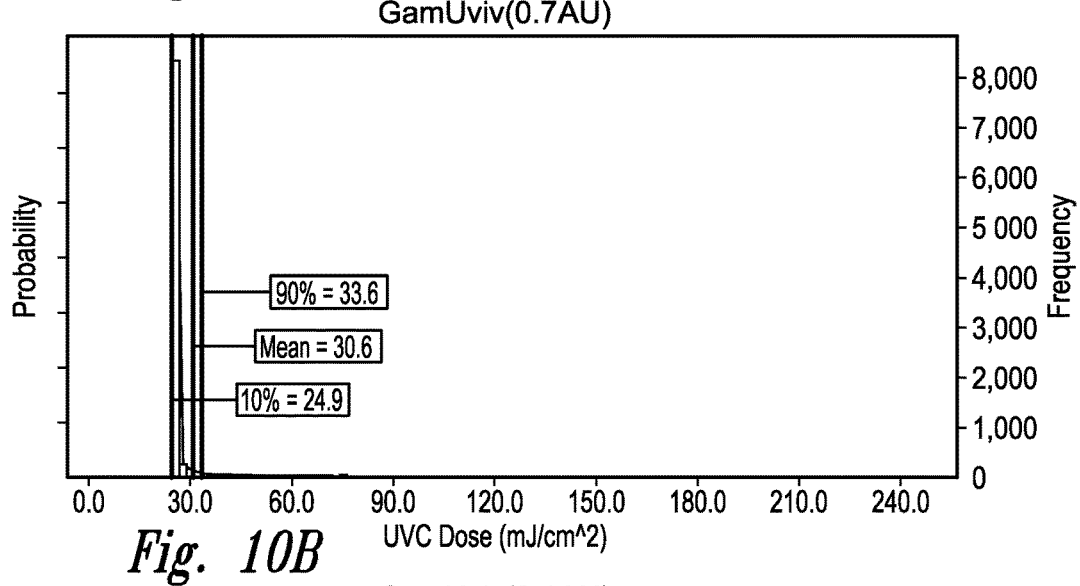
Figure 10C:
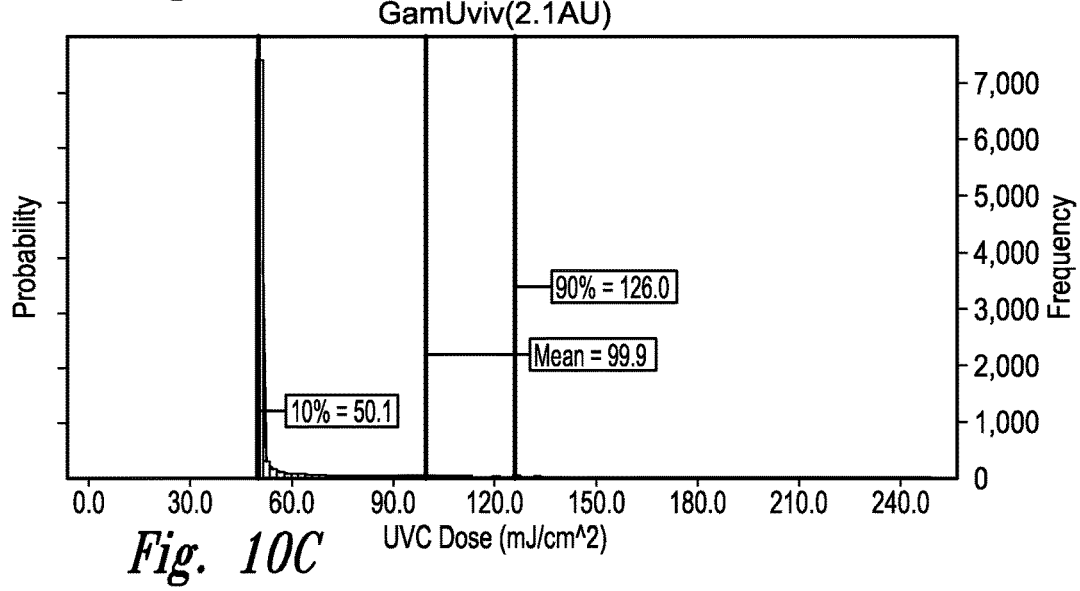
Figure 10D:
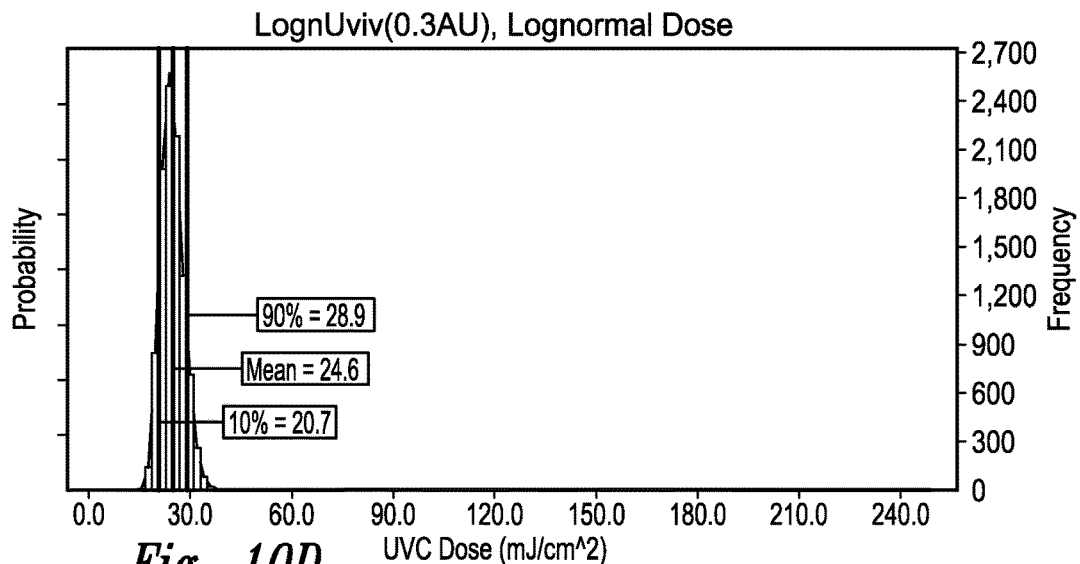
Figure 10E:
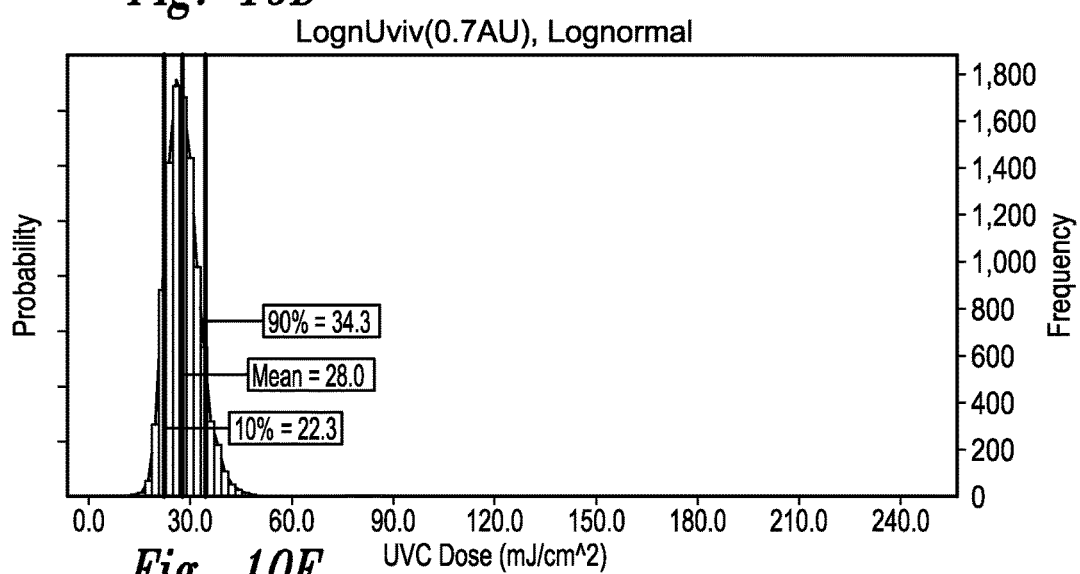
Figure 10F:
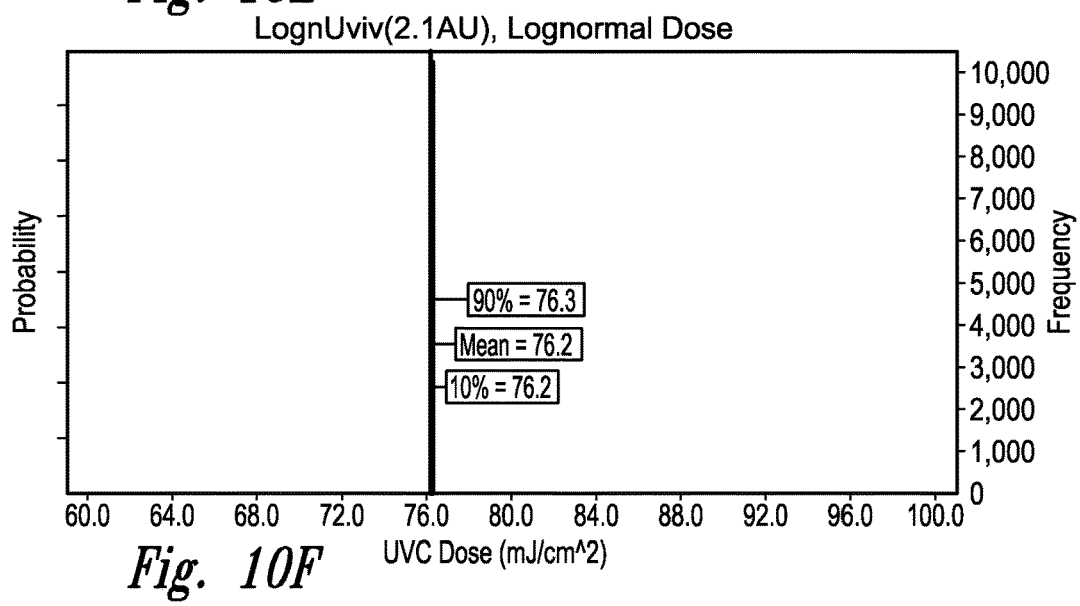
Figure 10G:
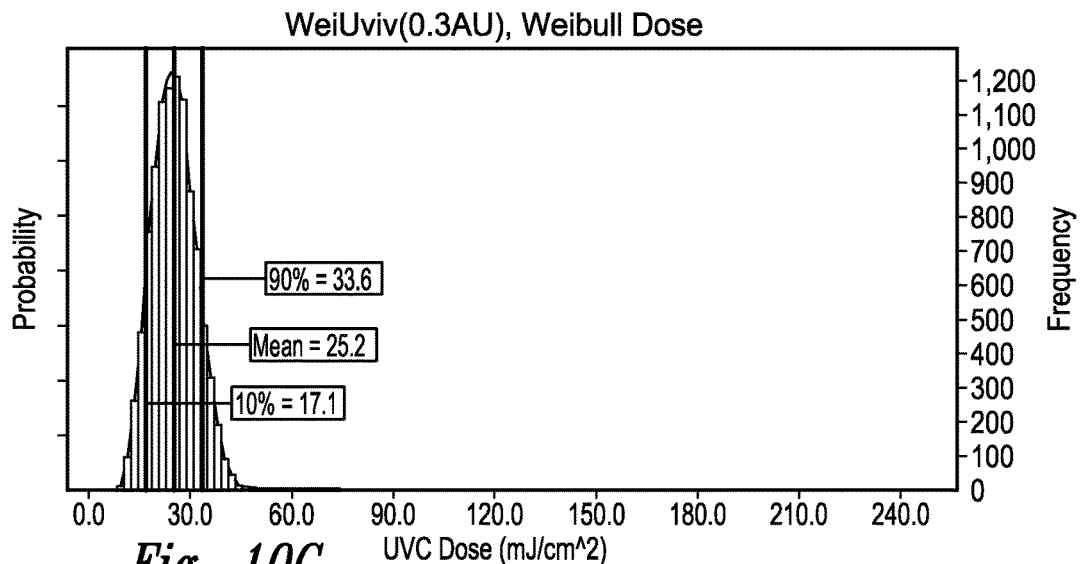
Figure 10H:
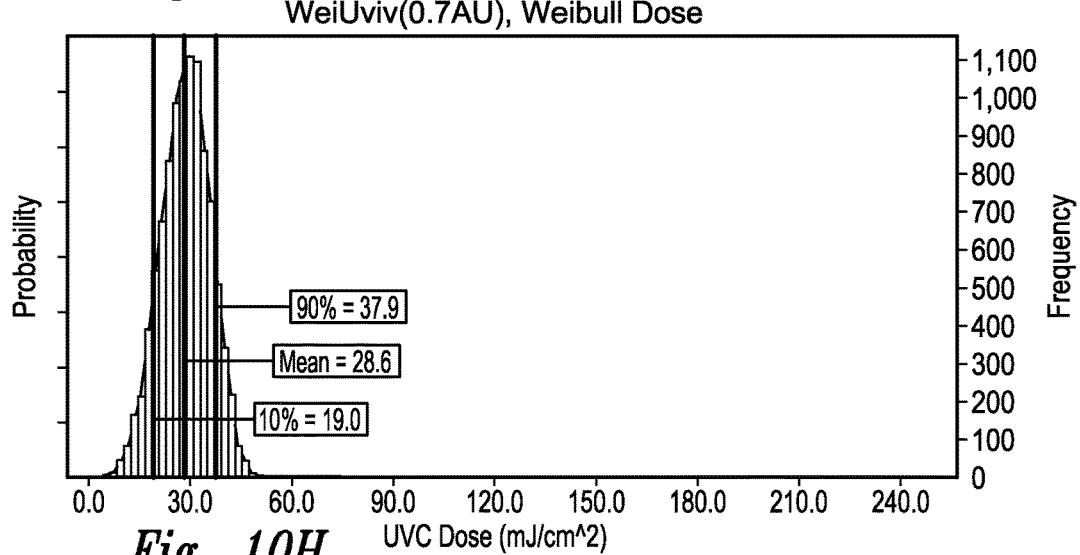
Figure 10I:
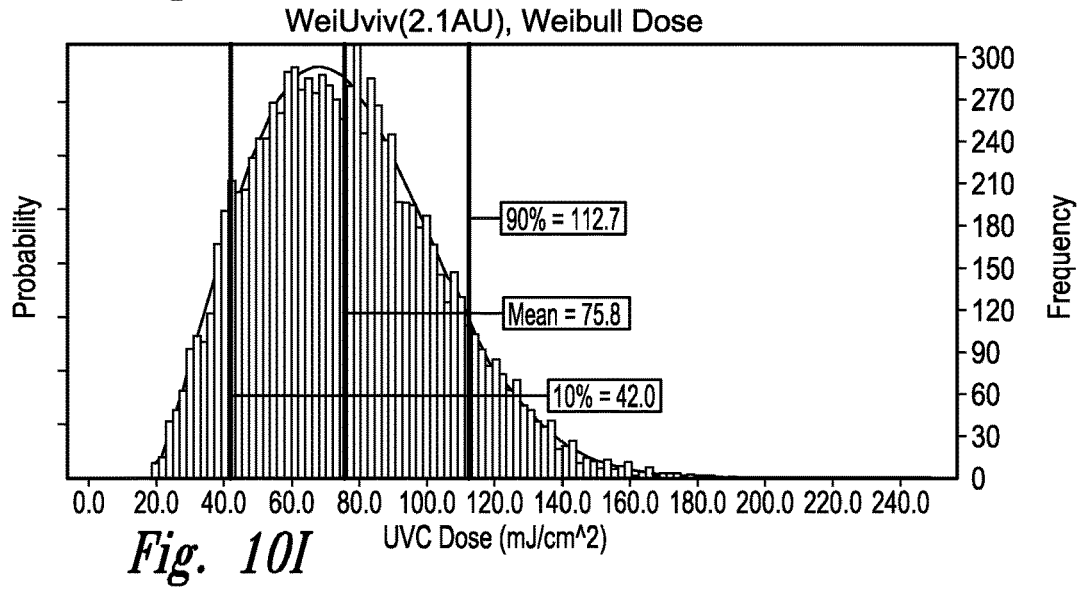

The result of a simulation and optimization using the above approach is shown in FIGS. 8A and 8B. The graphs depict the fluorescence cumulative probability distribution and dose distribution for one simulation and the corresponding experimental distribution. The experimental distribution appears more "step-wise" due to the more limited resolution of the experimental bins. Different process reactor treatments can produce quite different fluorescence distributions; correspondingly, the quality of the fit at points other than those used for objective and requirement specification can vary as can the extent of dose distribution asymmetry.

FIG. 8A depicts the cumulative probability distributions for experimental and simulated fluorescence distributions of microspheres treated with process reaction conditions; FIG. 8B shows the simulated dose distribution.

Effect of Dose Probability Density Function on Fluorescence Distribution Simulation Accuracy To simplify simulations and provide a systematic means for comparison, the dose distribution was abstracted by use of several well known asymmetric probability distribution functions including the Generalized Gamma, Lognormal, and Weibull Distributions. Simulations were conducted for all process reactor treatments with all probability density functions to facilitate comparison and choice of the most appropriate distribution function for future modeling. The highest quality fits were always obtained for the helical (0.3AU) and helical(0.7AU) treatment conditions regardless of the probability density function type used to represent the dose. Qualitatively, there appears to be a slight effect of the distribution type on the error associated with different percentiles of the fluorescence distribution. The error is essentially random for simulations using the Generalized Gamma Distribution whereas it is more linear or quadratic for the Lognormal and Weibull distributions, respectively. Regardless of distribution function type, the error was within 3% for all treatment types and percentiles between 10 and 90%. The error associated with simulations for the complex process reactors is comparable to that obtained for the collimated beam treatment. As the values for the bleaching constants for the process reactor simulation were obtained from collimated beam simulations, it is possible that the largest source of error in all simulations derives from the mathematical treatment of the bleaching kinetics.

Effect of Probability Density Function on the Shape of the Dose Distribution

The different probability density functions used to represent the dose have different properties and characteristics. Thus, they may behave differently during simulations and produce different dose distribution shapes. The dose distribution associated with different probability density functions obtained from simulation of fluorescence distributions derived from different thin-film process reactor treatments are shown in FIG. 9. The distributions obtained from simulation of different spiral reactor treatments are shown in FIG. 10.

The thin-film reactor treatment produces a broader dose distribution than the spiral reactor. For the broader distributions, the different probability density functions behave very similarly. At low absorbance the extent of asymmetry and skew appear indistinguishable. At higher absorbance the different probability density functions produce more differently appearing dose distributions. The generalized gamma produces a dose distribution with marked exponential character. The Weibull displays a similarly sharp rise at low dose but decays much more slowly at higher doses than the generalized gamma. The Lognormal, alternatively, retains the gradual rise and gradual decline observed at lower absorbance—other than broadening with increasing absorbance the appearance of the lognormal derived dose does not change significantly.

Simulations of thin-film reactor derived fluorescence distributions performed comparably for all probability density functions. All optimizations converged to within the specified tolerance with comparable numbers of iterations. The choice of the limits bounding the decision variable values had a significant effect on the performance of all simulations—once appropriate limits were identified the proportion of acceptable solutions obtained with the different distribution functions were similar. Choice of limits for the "location", "scale", and "shape" parameters for the generalized gamma and Weibull was more intuitive; thus, less preliminary searching was required to find appropriate initial values for the decision variable parameters in these cases.

The narrow dose distribution produced by the spiral reactor was more challenging to simulate and distinguished the different probability density functions more significantly. Treatment with the helical reactor produces a very narrow and steeply declining distribution for all absorbances when the generalized gamma is used to represent the dose. The resulting distributions are markedly exponential and seem to approach the Dirac-delta function in character. Use of the Weibull does not permit such extreme narrowing of the distribution. Rather, the behavior is strangely similar to that observed with the thin-film reactor as if the distribution function is approaching a mathematical limit. Use of the Lognormal distribution produced unpredictable and questionable behavior.

Simulations of the fluorescence distributions derived from the spiral reactor performed very differently for the different probability density functions. Simulations using the generalized gamma were well behaved in all cases and displayed smooth convergence to within the specified tolerance in similar numbers of iterations.

Simulations using the Weibull required considerably more searching to find initial decision value limits but ultimately converged as specified. Simulations using the Lognormal were not well-behaved; two of nine failed to converge and the remaining tended to produce singular behavior. Overall, the generalized gamma distribution exhibited the most reliable and flexible performance.

Effect of Probability Density Function on the Values of Dose Distribution Abstracts For practical reasons, dose distributions need to be described using abstracts, or simple numbers with understood meaning. For normal distributions, the commonly used abstracts are the mean and standard deviation. In the case of the generalized gamma, Lognormal, and Weibull distributions the logical extensions would seem to be the location, shape and scale parameters. Unfortunately, these parameters lack intuitive meaning for describing distribution position and expanse. More generally applicable measures include mean, mode, and percentiles—these measures will be used to quantify dose distributions for further calculations and limit estimation.

Since the probability density distribution used to represent the dose qualitatively appeared to influence the shape of the dose distribution, it was necessary to determine if the function can affect the values of abstracts used to quantify the distribution. To test this possibility, values for the mean, 10-Percentile, 50-Percentile, and 90-Percentile were tabulated from all reactor simulations using all probability density functions. The resulting values were analyzed by ANOVA to determine if a significant correlation with distribution type existed. Data and results from this analysis are shown in Table L (Reactor 1 is a thin-film reactor and Reactor 2 is a helical reactor). Statistical analysis shows convincingly that the distribution function used to represent the dose does not have a significant effect on the value of the dose distribution abstracts. The p-value for this effect is >0.5 whereas the p-value for the reactor type and media absorbance are <0.0001.

TABLE L

| | | | Dose Distribution Abstracts | | | | | | |
|---|---|---|---|---|---|---|---|---|---|
| | | Media | | Percentile | | | Asymetry Measures | | Fluorescence |
| PDF | Reactor | Abs | Mean | 10 | 50 | 90 | WD10% | WD90% | RMSE |
| Gamma | Reactor 1 | 0.3 | 25.00 | 9.79 | 21.49 | 45.02 | 54.42 | 109.56 | 1.92 |
| | | 0.7 | 35.50 | 18.52 | 30.94 | 58.79 | 40.15 | 90.00 | 1.77 |
| | | 2.1 | 83.90 | 30.22 | 56.55 | 175.41 | 46.56 | 210.19 | 0.89 |
| | Reactor 2 | 0.3 | 28.80 | 21.39 | 21.39 | 32.97 | 0.00 | 54.14 | 0.79 |
| | | 0.7 | 30.60 | 24.92 | 24.92 | 33.86 | 0.00 | 35.87 | 0.48 |
| | | 2.1 | 99.90 | 50.14 | 50.14 | 128.02 | 0.00 | 155.34 | 3.34 |
| | Reactor 2, 2pass | 0.3 | 63.10 | 58.13 | 58.13 | 65.84 | 0.00 | 13.25 | 0.80 |
| | | 0.7 | 93.70 | 70.74 | 70.74 | 106.75 | 0.00 | 50.90 | 0.81 |
| | | 2.1 | 216.30 | 124.25 | 201.72 | 325.14 | 35.41 | 61.18 | 1.20 |
| Lognormal | Reactor 1 | 0.3 | 24.60 | 10.65 | 21.36 | 42.67 | 50.11 | 99.92 | 1.73 |
| | | 0.7 | 36.80 | 18.40 | 31.10 | 58.75 | 40.83 | 88.91 | 1.70 |
| | | 2.1 | 81.90 | 28.22 | 66.43 | 153.72 | 57.52 | 131.40 | 1.98 |

TABLE L-continued

Dose Distribution Abstracts

| PDF | Reactor | Media Abs | Mean | Percentile 10 | 50 | 90 | Asymetry Measures WD10% | WD90% | Fluorescence RMSE |
|---|---|---|---|---|---|---|---|---|---|
| | Reactor 2 | 0.3 | 24.60 | 20.66 | 24.38 | 28.96 | 15.26 | 18.80 | 1.00 |
| | | 0.7 | 28.00 | 22.29 | 27.56 | 34.35 | 19.13 | 24.64 | 0.65 |
| | | 2.1 | 76.20 | 76.24 | 76.25 | 76.26 | 0.01 | 0.01 | 2.44 |
| | Reactor 2, | 0.3 | 61.60 | 59.25 | 61.65 | 63.91 | 3.74 | 3.82 | 1.15 |
| | 2pass | 0.7 | 84.10 | 83.41 | 84.06 | 84.70 | 0.77 | 0.76 | 1.44 |
| | | 2.1 | 214.90 | 140.83 | 194.19 | 313.47 | 27.48 | 61.43 | 0.59 |
| Weibull | Reactor 1 | 0.3 | 24.20 | 10.02 | 22.48 | 40.68 | 55.43 | 80.97 | 2.06 |
| | | 0.7 | 36.00 | 15.71 | 34.10 | 59.17 | 53.94 | 73.52 | 2.15 |
| | | 2.1 | 82.80 | 26.17 | 66.84 | 161.96 | 60.85 | 142.29 | 1.86 |
| | Reactor 2 | 0.3 | 25.20 | 16.99 | 23.03 | 33.68 | 32.13 | 34.53 | 0.86 |
| | | 0.7 | 28.60 | 18.90 | 28.96 | 37.93 | 34.74 | 30.96 | 0.80 |
| | | 2.1 | 75.80 | 41.78 | 73.68 | 112.89 | 43.30 | 53.21 | 1.07 |
| | Reactor 2, | 0.3 | 62.10 | 52.72 | 62.96 | 70.42 | 16.28 | 11.84 | 1.04 |
| | 2pass | 0.7 | 86.60 | 65.83 | 87.78 | 106.83 | 25.01 | 20.57 | 1.18 |
| | | 2.1 | 212.50 | 148.58 | 213.74 | 274.45 | 30.49 | 28.40 | 1.06 |

Estimation of the Uncertainty of the Values of Dose Distribution Abstracts

Measured and calculated scalar values can only be expressed with a finite degree of certainty. The same is true for higher dimension measures like distributions. In the specific case of UVC dose distribution, one can envision existence of a "confidence envelope" which fully encloses the distribution shape and represents the "space" in which the "line" scribing the distribution envelope must and can lie. A simpler quantitative expression of the uncertainty involves stating both a mean and a variance for all distribution abstracts (mean, 10-Percentile, 50-Percentile, and 90-Percentile).

The computational methods used to determine the dose distribution can increase uncertainty beyond that originating from experimental measurement variance. Accounting for the possible sources of uncertainty is a prudent initial step in estimating an appropriate value. Notable sources of error in the full process of UVC dose determination are given in Table M.

TABLE M

| Error source name | Description | First point variance can be observed |
|---|---|---|
| Collimated Beam Fluence Rate | Obtained via measurement with NIST traceable sensor and adjusted for optical influences | FACS of untreated microspheres. FACS of collimated beam treated microspheres. |
| Collimated Beam Exposure Time | Manually controlled using a stopwatch. Accumulative effect - result of method sequence. | |
| Microsphere Photochemistry | Reactivity may vary by material lot and/or material handling. Possible suspending matrix effect. | |
| FACS Measurement | Relative, not absolute, fluorescence measurement. Analog to digital conversion. Coincident optical events. Use of digital gating to exclude "optical noise" events. | |
| Bleaching Parameter Fit - mean and variance of values | Analytic form of bleaching equation Requirement Tolerance during Bleaching Parameter Fit affects variance | Quality of fit of collimated beam treated microsphere fluorescence distributions. |

TABLE M-continued

| Error source name | Description | First point variance can be observed |
|---|---|---|
| Dose Distribution Parameter Fit - mean and variance of values | Decision Variable Limits during Bleaching Parameter Fit affects variance Analytic form of probability density function equation Requirement Tolerance during Dose Distribution Fit affects variance Decision Variable Limits during Dose Distribution Fit affects variance | Quality of fit of process reactor treated microsphere fluorescence distribution. |

Inspection of the sources for error and the point at which its effect can be observed shows that the variance can be practically lumped into three categories:

1. error derived from the collimated beam, microsphere bleaching, and FACS measurement and measurable by population statistics of collimated beam FACS data;
2. uncertainty derived from the fit of the bleaching equation and measurable by the stochastic statistics of Monte-Carlo trials;
3. uncertainty derived from the fit of the dose probability density function and measurable by the stochastic statistics of Monte-Carlo trials.

Category 2 and 3 variance can additionally suffer from propagation of variance effects. That is, the variance induced by the bleaching parameter fit can be amplified (or attenuated) with passage through the dose distribution fit. Such behavior is possible with non-linear systems (like that present in the bleaching equation). These different categories for variance are addressed separately and then combined to create a method for estimation of the uncertainty of the values of dose distribution abstracts.

The contribution of category 2 and 3 variance sources were estimated by conducting Monte Carlo simulations with systematically altered requirement tolerance ranges; decision variable limits were correspondingly adjusted so that a similar proportion of acceptable solutions were obtained from each simulation. The purpose of these simulations was to determine the approximate magnitude of the uncertainty derived from Monte-Carlo simulations to determine bleaching parameter values and dose distribution measures. The tolerance limits for the fluorescence were chosen as the "lever" to modulate the uncertainty because they must be specified to conduct a simulation and they can, conceivably, be aligned with an independently determined measure of fluorescence variance. As expected, the fluorescence tolerance ranges do not affect the mean values of the fluorescence or dose distribution abstracts but they do affect the variance (standard deviation or coefficient of variance). The magnitude of the variance from these sources, however, is not particularly large as the fluorescence CV only ranges between 0.002 and 0.0083 (Table M, +/−2FU tolerance scenario).

The contribution of category 1 variance sources was estimated by analyzing fluorescence data from numerous collimated beam treatments and FACS analyses using population statistics methods. The analysis shows that category 1 source variance is significantly larger than that from other contributions as the fluorescence CV ranges between 0.02 and 0.04. As the category 1 variance contribution is five to ten times larger than that from categories 2 and 3 combined, only the category 1 variance contribution need be considered in estimating the overall variance of dose distribution abstract values.

In principle, the variance (or uncertainty) associated with a dose distribution abstract can be determined using Monte-Carlo simulations (Brattin 1996, Frey 1998). Unfortunately, the effect of the tolerance ranges on variance is not well controlled as evidenced by the large range in the CV derived from the different reactor types at constant fluorescence tolerance and similar dose. Since estimates of the uncertainty determined by Monte-Carlo methods appear to depend on other uncontrolled factors (such as bounding limits for objective values), other methods were needed to estimate these values.

To develop a means to estimate the degree of variance and/or uncertainty in dose distribution abstracts, it was hypothesized that the coefficient of variance of the dose may be related to the coefficient of variance of the fluorescence. Examination of the simplest relationship, linear proportionality, showed that the parameter was well behaved for different simulation scenarios and varied over a very limited span. Further justification for the use of this parameter to estimate variance was provided by comparing the value of RatioCV obtained using Monte Carlo techniques with that obtained using population statistics modeling techniques. The comparison of these results is provided in FIG. 11 and demonstrates that the value of this parameter depends little on the method used for its computation and that it is equally applicable to different regions of the probability distributions (mean and 10, 50, 90 percentile).

Figure 11:
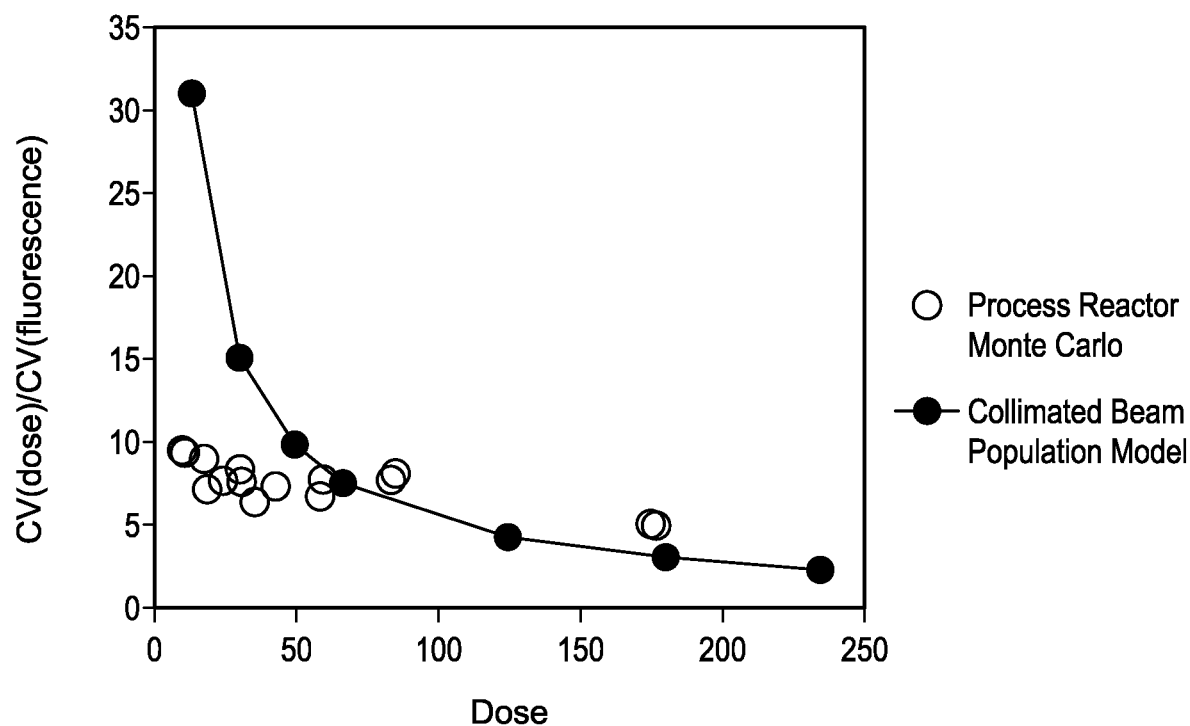
FIG. 11 is a plot showing comparing the value of RatioCV obtained using Monte Carlo techniques with that obtained using population statistics modeling techniques. Solid circle represents process reactor Monte Carlo. Open circle represents collimated beam population model.
Figure 12A:
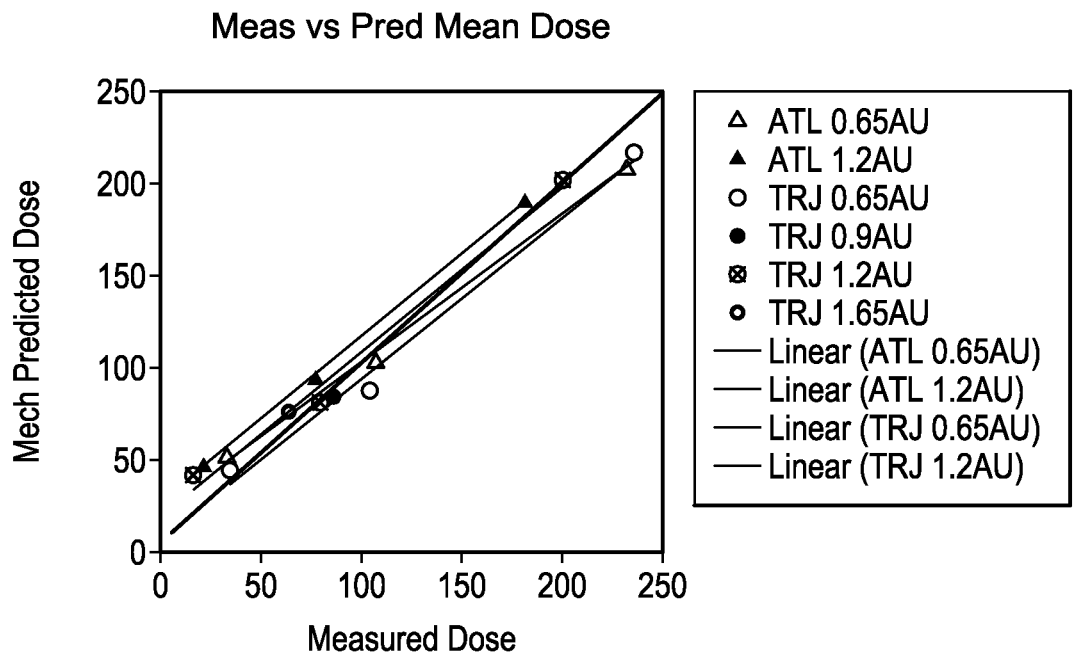
FIG. 12 is a plot showing a graphical representation of a pair-wise analysis of experimental and predicted dose data.
Figure 12B:
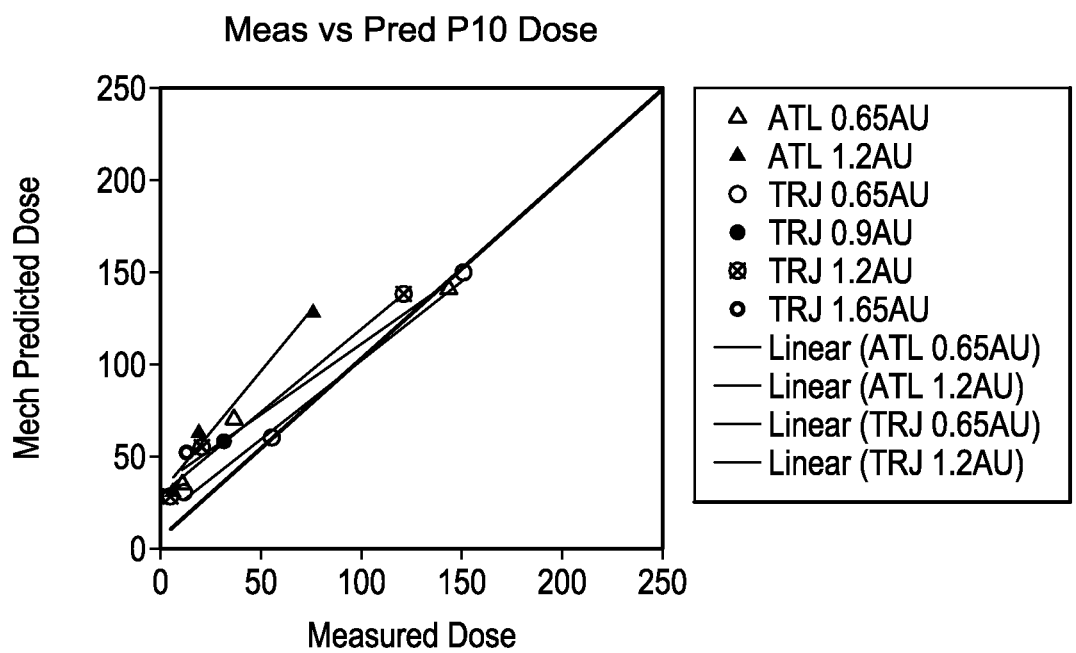
Figure 12C:
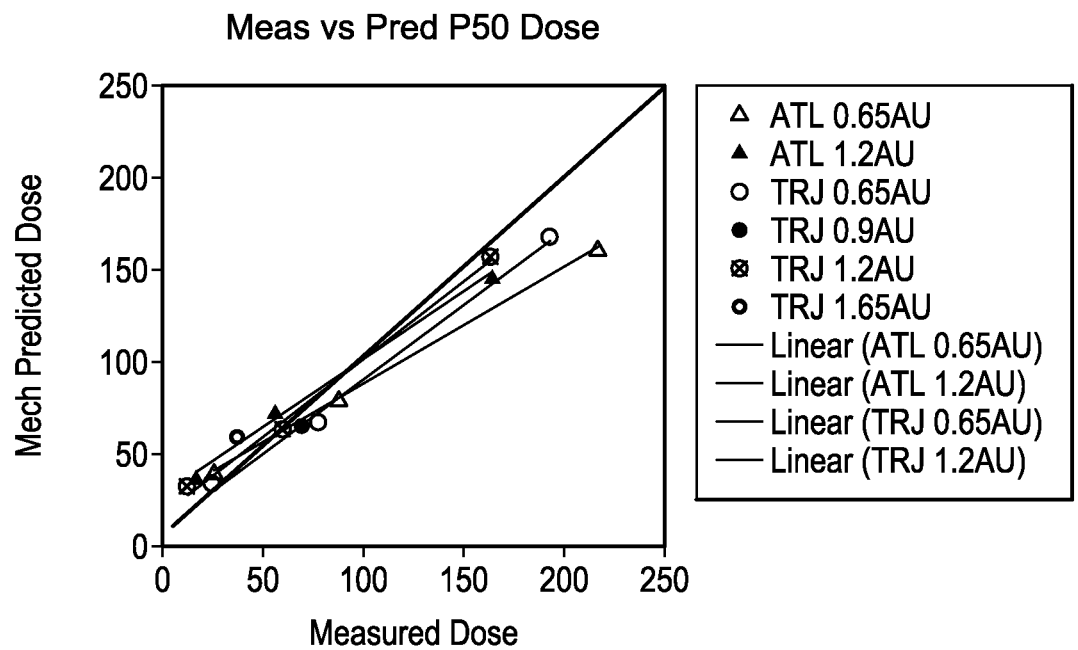
Figure 12D:
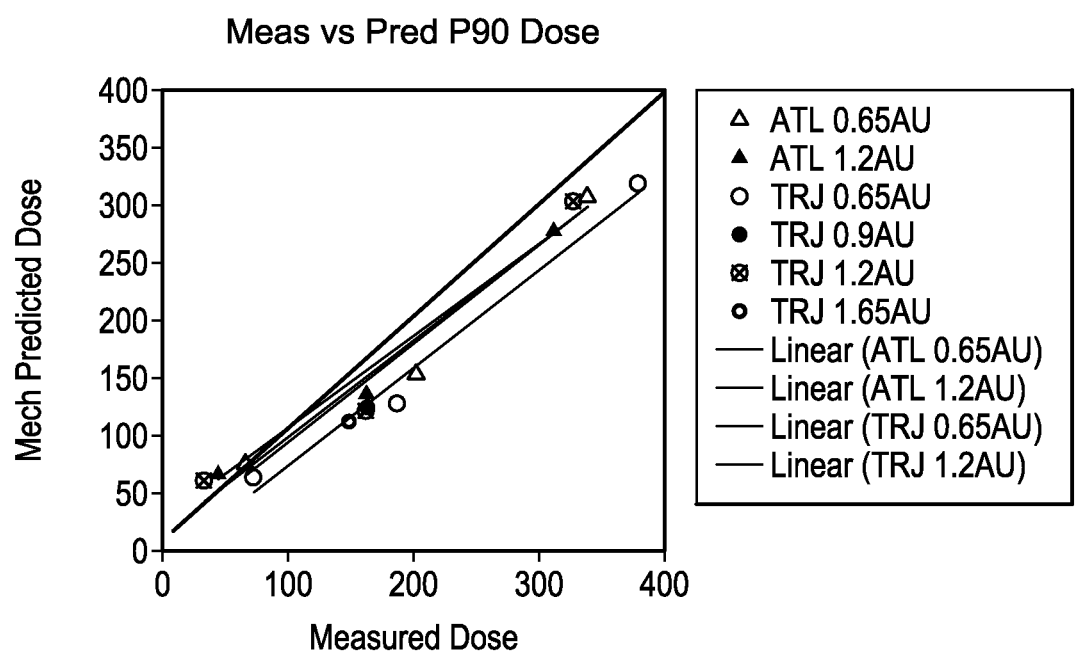

As the variance contribution from the experimental treatments (category 1) was clearly largest, the variance for the dose distribution was calculated from the collimated beam population variance using an expression for the CVRatio parameter derived using the population model (shown by solid symbols and fitted line in FIG. 11). The mathematical expression for the dose distribution abstract variance is given in Table N:

TABLE N

| Definitions: | |
|---|---|
| CV(Dose_X) | = SD(Dose_X)/Mean(Dose_X) |
| CV(FI_X) | = SD(FI_X)/Mean(FI_X) |
| RatioCV(Dose) | = CV(Dose_X)/CV(FI_X) |
| Scaling equation: | |
| SD(Dose_X) | = Mean(Dose_X)*CV(Dose_X) |
|  | = Mean(Dose_X)*CV(FI_X)*RatioCV(Dose) |
|  | = Mean(Dose_X)*(SD(FI_X)/Mean(FI_X))*RatioCV(Dose) |
| SD(Dose_X) | = (Mean(Dose_X)/(Mean(FI_X))*SD(FI_X)*RatioCV(Dose) |
| Values (equations) of Terms in Scaling Equation: | |
| (Mean(Dose_X)/Mean(FI_X) | [Dose_mean, FI_mean], [Dose_P50, FI_P50], [Dose_P10, FI_P90], [Dose_P90, FI_P10] |
| SD(FI_X) | = SD(FIratio)*Mean(FI_0) := (0.02)*Mean(FI_0) |
| RatioCV(Dose) | = 1.945 + 295.4*(1/dose) |
| Source of Terms in Scaling Equation: | |
| (Mean(Dose_X)/Mean(FI_X)) | Monte Carlo Simulation in Process Reactor |
| SD(FI_X) | Rick Burdicks population model for RatioFI on Dose from Collimated Bean datasets |
| RatioCV(Dose) | Rick Burdicks "Reciprocal fit" of data shown on graph |

Table N provides expressions used to calculate the standard deviation of the dose distribution abstract from collimated beam fluorescence distribution population standard deviation.

Application of this formulation for estimating dose distribution variance for the data and simulations described in this report are given in Table N. The behavior of these results are in good agreement with those expected from fundamental analyses of uncertain distribution properties (Brattin 1996, Frey 1998).

Table O provides the mean and standard deviation of dose distribution abstracts calculated using the methods described in Table N (R1=Reactor 1, a thin-film UVC reactor):

TABLE O

| Distribution Abstract | | Dose +/− SD |
|---|---|---|
| G_Dose_R1(0.3AU) | 10 Percentile | 10.4 +/− 7 |
|  | Mean | 24.6 +/− 8.7 |
|  | 90 Percentile | 43.3 +/− 11.2 |
| G_Dose_R1(0.7AU) | 10 Percentile | 18.3 +/− 7.9 |
|  | Mean | 35.8 +/− 9.8 |
|  | 90 Percentile | 59.4 +/− 12.8 |
| G_Dose_R1(2.1AU) | 10 Percentile | 30.3 +/− 9.1 |
|  | Mean | 84.6 +/− 13.9 |
|  | 90 Percentile | 176.9 +/− 23.6 |

Conclusions from Example 2

A deterministic convolution model was developed to simulate the effect of UVC fluorescent bleaching. The model contains a bleaching function analogous to those used for quantitative analysis in photo-microscopy and laser induced fluorescence velocity measurements. The bleaching function is used to transform the untreated microsphere fluorescence distribution. Kinetic constants are found by optimizing the fit to select treated microsphere fluorescence distribution means. Entire distribution features are accurately recreated across a wide dose range using this mathematical approach.

The bleaching analysis is extended to process reactors by conducting stochastic mathematical convolution of the dose distribution with the untreated microsphere fluorescence distribution. Comparison of different asymmetric distribution functions to represent the dose revealed that the functional form affected the visual appearance of the dose distribution but not the quantitative distribution abstracts. The generalized gamma distribution was chosen to generally represent the dose since it exhibited superior robustness and convergence relative to other distribution functions.

A mathematical framework was developed to estimate the uncertainty (and variance) associated with different dose distribution abstracts. The methodology utilizes the coefficient of variance determined from analysis of numerous collimated beam treatments using population statistics. The variance for different distribution abstracts is scaled in relation to the dose and fluorescence values of the abstract. The general behavior of the resulting variance approximation method is in good agreement with those determined by alternative numerical means.

References Cited in Example 2

Jonathan W. Martin, Joannie W. Chin, Tinh Nguyen, "Reciprocity Law Experiments in Polymeric Photodegradation: A Critical Review" *Progress in Organic Coatings*, v. 47, pg. 292-311, (2003)

James R. Bolton, Karl G. Linden, "Standardization of Methods for Fluence (UV Dose) Determination in Bench-Scale UV Experiments" *J. Envir. Engrg.* V. 129, n. 3, pg. 209-215 (2003)

Ernest R. Blatchley III, et. Al, "Dyed Microspheres for Quantification of UV Dose Distributions: Photochemical Reactor Characterization by Lagrangian Actinometry" J. Envir. Engrg-ASCE, v. 132, n. 11, pg. 1390-1403, (2006)

Zuzana Bohrerova, et. Al, "Experimental Measurements of Fluence Distribution in a UV Reactor using Fluorescent Microspheres" *Envir. Sci. Tech.*, v. 39, n. 22, pg. 8925-8930, (2005)

Karl G. Linden, et. Al, "Demonstrating 4-log Adenovirus Inactivation in a Medium-Pressure UV Disinfection Reactor", *J. Am. Water Works Assn.*, v. 101, n. 3, pg. 90-99, (2009)

Robert A. Hoffman, "Standardization and Quantitation in Flow Cytometry", *Meth. Cell Biol.*, v. 63, pg. 299-340, (2001)

Loling Song, E. J. Hennink, Ted Young, and Hans J. Tanke, "Photobleaching Kinetics of Fluorescein in Quantitative Fluorescence Microscopy", *Biophys. J.*, v. 68, pg 2588-2600 (1995)

Loling Song, C. A. G. O. Varma, J. W. Verhoeven, Hans J. Tanke, "Influence of the Triplet Excited State on the Phtobleaching Kinetics of Fluorescein in Microscopy", Biophysical Journal, V. 70, pg. 2959-2968, (1996)

Loling Song, R. P. M. van Gijlswijk, I. Ted Young, and Hans J. Tanke, "Influence of Fluorochrome Labeling Density on the Photobleaching Kinetics of Fluorescein in Microscopy", *Cytometry*, v. 27, pg. 213-223 (1997)

J. P. Crimaldi, "The effect of photobleaching and velocity fluctuations on single-point LIF Measurements" *Exp. Fluids,* v. 23, pg. 325-330 (1997)

L. G. Larsen, J. P. Crimaldi, "The effect of photobleaching on PLIF" *Exp. Fluids*, v. 41, pg. 803-812, (2006)

M. Talhavini, TDZ Atvars, "Photostability of xanthenes molecules trapped in poly(vinyl alcohol) PVA matrices" *J. Photochem. Photobiol. A: Chemistry*, v. 120, pg. 141-149, (1999)

C. Morris, "Natural exponential families with quadratic variance functions", *Annals of Statistics,* 10(1), pg. 65-80, (1982)

W. Brattin, T. Barry, N. Chiu, "Monte Carlo modeling with uncertain probability density functions", *Human and Ecological Risk Assessment*, 2(4), pg. 820-840, (1996)

H. C. Frey, D. S. Rhodes, "Characterization and Simulation of Uncertain Frequency Distributions: Effects of Distribution Choice, Variability, Uncertainty, and Parameter Dependence." *Human and Ecological Risk Assessment*, 4(2), pg. 423-468 (1998)

EPA, United States Environmental Protection Agency, "Ultraviolet Disinfection Guidance Manual for the Final Long Term 2 Enhanced Surface Water Treatment Rule", Office of Water (4601), EPA 815-R-06-007, November (2006)

Example 3

Idealistic Mechanistic Dose Model for Thin-Film Reactor

In Example 3 a deterministic convolution model is described to simulate the dose distribution produced by passage through a continuous-flow thin-film UVC reactor. The model contains functions to account for the radial dependence of the UVC fluence rate and the axial flow velocity in the annular region formed between two circular cylinders. The UVC dose distribution is calculated by convolving the fluence rate and residence time for a velocity weighted distribution of radial positions in accordance with the reciprocity law. The convolution is conducted using the Monte-Carlo method. Distribution abstracts are extracted and compared with those obtained experimentally using the fluorescent microsphere bleaching method. The model is also used to mathematically characterize the effect of several reactor design and/or operational parameters.

An experimental method for UVC dose distribution determination using photo-bleaching of UVC sensitive fluorescent beads (See Example 1) and a deterministic convolution model to quantify the dose distribution delivered to the fluorescent beads during passage through a flow-through reactor (See Example 2) have been used previously to support process and reactor design. There remains a need for a predictive model to determine the effect of operational parameter values on the received dose to allow informed adjustment of one parameter (such as flow rate) to offset changes in other parameters (such as media absorbance or lamp power). The fact that the dose delivered by process reactors is inherently distributed has necessitated the use of predictive models to support process and reactor design; particularly in use contexts which are regulated by government agencies (see, e.g., EPA (2006)). The most commonly utilized models employ computational fluid mechanics with stochastic trajectory predictions to estimate the distribution of doses delivered to a population of hypothetical particles (Liu 2004). These models are considered to be accurate and reliable despite very limited experimental verification, especially in regards to predicting dose distribution profiles. An additional shortcoming of these models is they require highly specialized computer software systems and operators and the computations have little transparency or intuitiveness.

Example 3 described a new deterministic model for predicting the UVC dose distribution accrued with passage through the annular region of a thin-film reactor formed from two concentric cylinders. The model computes the dose by convolving the UVC fluence distribution (function of radius) with the residence time (function of radius) in accordance with the reciprocity law for irradiance. The convolution uses the Monte-Carlo method wherein the radius distribution is specified by a velocity weighted distribution function. The equations for the fluence rate and the axial velocity derive from analytic solutions of fundamental equations which are available for the simple concentric cylinder geometry.

Materials and Methods for Example 3

Experimental Determination of UVC Dose

UVC distribution is determined experimentally by quantifying the bleaching of fluorescent microspheres. The fluorescence microsphereswer treated with a collimated beam (control) and continuous-flow reactor (unknown) and measured with a digital flow cytometer (FACS) to determine the fluorescence distribution as described in Example 1. The UVC dose distribution is extracted from the fluorescence distribution using a deterministic convolution model which employs a kinetic bleaching equation and the generalized gamma distribution in accordance with the reciprocity law, as described in Example 2.

Statistical Assessment of Accuracy

Predicted and measured dose distribution abstracts were compared by ANOVA and other established statistical methods.

Fundamental Physics

Photo degradation phenomena are governed by a common physical law, the Reciprocity law, which can be expressed as:

$$\text{Damage} = \int_\lambda \text{function}(\text{Dose}(\lambda)) d\lambda$$

$$\text{Dose}(\lambda) = \int_t I(\lambda, t) dt$$

Critical review of the reciprocity law has shown it is uniformly obeyed for biological materials and almost always true for synthetic materials used to produce fluorescent microspheres (Martin (2003)). Low pressure mercury lamps produce essentially monochromatic light at a wavelength of 254 nm so the integration over wavelength is not necessary (EPA (2006)). The practical significance of this law is the degree of damage depends on the dose of radiation and different combinations of intensity and time can yield the same dose. Thus, different microspheres may traverse different paths through the UVC reactor and experience different radiation intensities and residence times but accumulate the same dose and, hence, the same amount of damage. In mathematical terms, the forward calculation (intensity, time to damage) is unique while the reverse calculation (damage to intensity, time) is not unique. In the special case of time invariance, the dose is equal to the product of the fluence rate (I) and the exposure time (t).

UVC Fluence

Various methods for calculating the fluence rate have been devised and incorporated into models to predict dose in UVC process reactors. The accuracy of the most commonly used methods were compared with experimental measurements using stationary actinometer globes suspended in either air or water at different locations and distances (5 to 15 cm) from the lamp surface. Results showed that a simple radial model is most accurate very close to the lamp surface (Liu (2004)). The radial model was used to successfully predict the degree of inactivation in a thin-film reactor (~5 mm annulus) with moderately absorbing liquids (Abs=3 to 6 cm$^{-1}$) (Ye (2007)). Reflection contributions may be important for small annulus thin-film reactors and low absorbance fluids (Bolton (2000)). The radial fluence rate model with attenuation from absorption and outer wall reflection is expressed as (Liu (2004)):

$$I(r) = I_1(r) + I_2(r)$$

$$I_1(r) = \left[\frac{P}{2\pi rL}\right] * RF_1 * \left[T10^{\left\{\frac{(r-r_1)}{0.01}\right\}}\right]$$

$$I_1(r) = \left[\frac{P}{2\pi r_0 L}\right] * RF_1 * \left[T10^{\left\{\frac{(r_0-r_1)}{0.01}\right\}}\right] * RF_2 * \left[T10^{\left\{\frac{(r_0-r)}{0.01}\right\}}\right]$$

$$RF_1 = (1 - R_1) * T_q * (1 - R_2)$$

$$I(r) = \text{Total Fluence Rate} \left(\frac{mJ}{cm^{2s}}\right)$$

$$I_1(r) = \text{Forward Fluence Rate} \left(\frac{mJ}{cm^{2s}}\right)$$

$$I_2(r) = \text{Reverse Fluence Rate} \left(\frac{mJ}{cm^{2s}}\right)$$

$RF_1$ = Quartz Reflectance Factor $R_1$ = Air to Quartz Reflectance $R_2$ = Quartz to Water Reflectance $T_q$ = Quartz Transmission $RF_1$ = Stainless steel Reflection Factor Residence Time The simple geometry of the thin-film reactor allows analytic solution of the Navier-Stokes equation of motion for low Reynolds number, commonly referred to as annular Poiseuille flow. A characteristic of this flow regime is the existence of uniform field lines equidistant from the lamp center yielding the practical result that axial flow trajectories are parallel to the lamp surface. The residence time associated with a specific trajectory is proportional to the inverse of the axial velocity. The axial velocity and associated residence time in the annular space of the thin-file reactor are expressed as (Munson (1990)):

$$\tau(r) = L/u$$

$$v_2(r) = (-2Q/\pi) * [(r^2 - r_0^2) + (R_2/R) * \ln(r/r_0)] * [R_4 - (R_2^2/R)]^{-1}$$

$$R = \ln(r_0/r_i)$$

$$R_2 = r_i^2 - r_0^2$$

$$R_4 = r_0^4 - r_i^4$$

$\tau(r)$ = Residence Time($s$)

$v_2(r)$ = Axial Velocity($m/s$)

$r_i$ = Inner Radius of Annulus($m$)

$r_0$ = Outer Radius of Annulus($m$)

Radial Probability Function

To accomplish Monte-Carlo integration of the fluence rate and residence time in accordance with the reciprocity law it is necessary to establish a radial probability function. This probability function ensures that the frequency which radius values are sampled in Monte-Carlo computations is comparable to that occurring in the real world. In the real world, represented for example by a fluorescent microsphere bleaching experiment, the number of particles within a collected volume which traversed the reactor at a given radius is proportional to the axial velocity of the fluid at that radius. This result occurs because the particles are uniformly dispersed and the axial flow is time invariant and rotationally symmetric (Ye (2007)).

$$\Omega(r)=[n(r)]/[n(total)]=[v_2(r)rdr]/[\int_{ri}^{ro} v_2(r)rdr]$$

For the case of flow through concentric cylinders, the radial probability function is expressed as:

$$v_z(r)/Q=(-2/\pi)*[(r^2-r_0^2)+(r_2/r)]*(R_4-R_2^2/R)^{-1}$$

Results and Discussion for Example 3

Reactor Design and Operating Parameters

Figure 32:
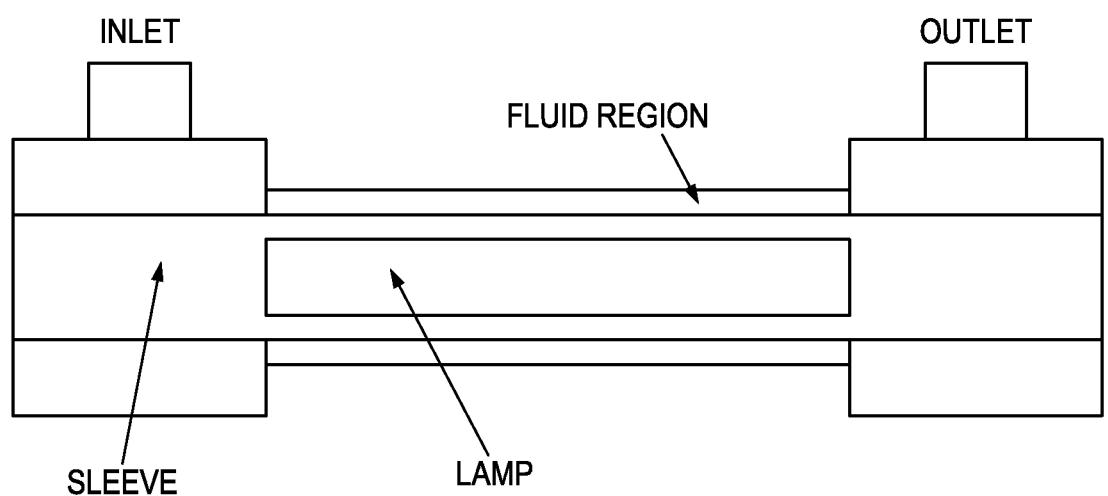
FIG. 32 shows a schematic of a reactor.

The accuracy of predictions derived from the mechanistic model was assessed by conducting a pair-wise analysis of experimental and theoretical data. The experimental data were obtained using the fluorescent bead bleaching method applied to two different thin-film reactors under with different operational parameters. Operational and design parameters unique to the different reactor types are given in Table P. A schematic of a reactor is provided in FIG. 32. Operational parameters from the specific test experiments conducted with the reactors are given in Table Q.

TABLE P

| Parameter | Reactor 1 | Reactor 2 |
| --- | --- | --- |
| Lamp Power (v) | 82 | 33 |
| Lamp Length (m) | 1.473 | 1.475 |
| Quartz Sleeve Diam. (mm) | 30.02 | 23.46 |
| Annular Gap (mm) | 0.89 | 1.09 |
| R1 | 0.04 | 0.04 |
| R2 | 0.002 | 0.002 |
| Tq | 0.9 | 0.9 |
| RF2 | 0.3 | 0.3 |

TABLE Q

| Reactor 1 | | | Reactor 2 | | |
| --- | --- | --- | --- | --- | --- |
| Exp# | A254 (AU) | Flow (LPM) | Exp# | A254 (AU) | Flow (LPM) |
| 0.65AU 2LPM | 0.65 | 2 | 0.65AU 1LPM | 0.65 | 1 |
| 0.65AU 5LPM | 0.65 | 5 | 0.65AU 2LPM | 0.65 | 2 |
| 0.65AU 10LPM | 0.65 | 10 | 0.65AU 4LPM | 0.65 | 4 |
| 0.9AU 5LPM | 0.9 | 5 | 1.2AU 1LPM | 1.2 | 1 |
| 1.2AU 2LPM | 1.2 | 2 | 1.2AU 2LPM | 1.2 | 2 |
| 1.2AU 5L | 1.2 | 5 | 1.2AU 4LPM | 1.2 | 4 |
| 1.2AU 10LPM | 1.2 | 10 | | | |
| 1.65AU 5LPM | 1.65 | 5 | | | |

Measured and Predicted Pair-wise Data

The dose delivered to the fluorescent microspheres in the experiments detailed in Table Q, as determined by FACS and subsequent deterministic deconvolution, is given in Table R. Note that dose is describable by a distribution function since process reactors do not deliver a uniform dose. The distribution function is described using the distribution abstracts mean, P10, P50, and P90.

TABLE R

| | Dose Distribution Abstract Values (mJ/cm$^2$) | | | |
| --- | --- | --- | --- | --- |
| Exp# | Mean | 10-P | 50-P | 90-P |
| R1 0.65AU 1LPM | 231.9 | 143.9 | 217.5 | 339 |
| R1 0.65AU 2LPM | 107.1 | 36.5 | 88.4 | 202.8 |
| R1 0.65AU 4LPM | 33.2 | 10.5 | 25.6 | 66.3 |
| R1 1.2AU 1LPM | 182.0 | 75.9 | 164.0 | 311.9 |
| R1 1.2AU 2LPM | 76.9 | 19.6 | 56.0 | 162.3 |
| R1 1.2AU 4LPM | 21.4 | 6.0 | 16.6 | 43.2 |
| R2 0.65AU 2LPM | 237.0 | 152.7 | 193.2 | 380.0 |
| R2 0.65AU 5LPM | 104.2 | 55.8 | 77.8 | 188.2 |
| R2 0.65AU 10LPM | 35.1 | 11.8 | 24.4 | 72.9 |
| R2 0.9AU 5LPM | 86.6 | 32.0 | 69.5 | 164.2 |
| R2 1.2AU 2LPM | 200.8 | 122.4 | 164.0 | 328.5 |
| R2 1.2AU 5LPM | 79.5 | 21.3 | 60.6 | 163.1 |
| R2 1.2AU 10LPM | 16.8 | 5.8 | 12.4 | 33.8 |
| R2 1.65AU 5LPM | 64.2 | 14.1 | 37.9 | 149.5 |

The predicted dose delivered in the experiments detailed in Table R, as determined using the model described in the model development section, is given in Table S. The dose distribution functions are described by the same distribution abstracts to enable direct comparison for model accuracy determination.

TABLE S

| | Dose Distribution Abstract Values (mJ/cm$^2$) | | | |
| --- | --- | --- | --- | --- |
| Exp# | Mean | 10-P | 50-P | 90-P |
| R1 0.65AU 1LPM | 208.8 | 142.5 | 161.7 | 310.5 |
| R1 0.65AU 2LPM | 104.4 | 71.2 | 80.9 | 155.3 |
| R1 0.65AU 4LPM | 52.2 | 35.6 | 40.4 | 77.6 |
| R1 1.2AU 1LPM | 190.6 | 129.1 | 146.7 | 280.5 |
| R1 1.2AU 2LPM | 95.3 | 64.5 | 73.3 | 140.3 |
| R1 1.2AU 4LPM | 47.7 | 32.3 | 36.7 | 70.1 |
| R2 0.65AU 2LPM | 216.8 | 148.0 | 167.1 | 318.3 |
| R2 0.65AU 5LPM | 86.7 | 59.2 | 66.8 | 127.3 |
| R2 0.65AU 10LPM | 43.4 | 29.6 | 33.4 | 63.7 |
| R2 0.9AU 5LPM | 83.7 | 57.1 | 64.8 | 124.4 |

TABLE S-continued

Dose Distribution Abstract Values (mJ/cm$^2$)

| Exp# | Mean | 10-P | 50-P | 90-P |
|---|---|---|---|---|
| R2 1.2AU 2LPM | 200.9 | 136.8 | 156.5 | 302.2 |
| R2 1.2AU 5LPM | 80.4 | 54.7 | 62.6 | 120.9 |
| R2 1.2AU 10LPM | 40.2 | 27.4 | 31.3 | 60.4 |
| R2 1.65AU 5LPM | 75.7 | 51.2 | 58.1 | 110.9 |

Accuracy of Predicted Dose

Experimental and theoretical predictions are compared diagrammatically in FIG. 12. Data sets are grouped by reactor and fluid absorbance allowing linear fits (across flow rate). If predictions were perfectly accurate all data points would lie on the 45 degree diagonal in each panel. Review of diagrams clearly reveals the presence of variance within the measured values (the predicted values are deterministic in nature; hence, do not have variance). The variance associated with different measured dose distribution abstracts was previously estimated for the fluorescent microsphere assay combined with the deterministic convolution method used to determine dose (see Example 2).

Formal statistical analysis was conducted to address two questions: (1) Do the two thin-film reactors produce statistically different dose distributions? And (2) What is the range of dose where the measured and predicted doses are not statistically different? The comparison of reactors required use of the mechanistic model because the comparison experiments utilized different operational parameters (and different reactors with different design parameters) and consequently required "normalization" for suitable comparison. The later analysis was conducted as part of characterization of the mechanistic model to enable subsequent use to predict operational parameter values required to produce target dose values.

With regard the first question, the process reactors do not produce statistically different dose distributions and are considered equivalent and interchangeable. With regard the second question, the mechanistic model does not produce statistically different results than experiment for dose abstract values within the ranges specified in Table T below. The normal operation Mean and P50 dose abstract values are contained in the specified ranges and the predictions are considered accurate for intended use. The normal operation P10 and P90 dose abstract values may, alternatively, lie outside the specified ranges and require further analysis.

TABLE T

| Response | Analysis 1: Is there evidence of a difference due to reactor? | Analysis2*: What is the range of Microsphere Dose where there is no significant difference between regression of Mechanistic Dose on the Microsphere Dose and a 45 degree line emanating from (0,0)? |
|---|---|---|
| Mean | No. | 70-225 mJ/cm$^2$ |
| P10 | No. | 98-160 mJ/cm$^2$ |
| P50 | No. | 50-105 mJ/cm$^2$ |
| P90 | No. | 0-144 mJ/cm$^2$ |

Figure 13:
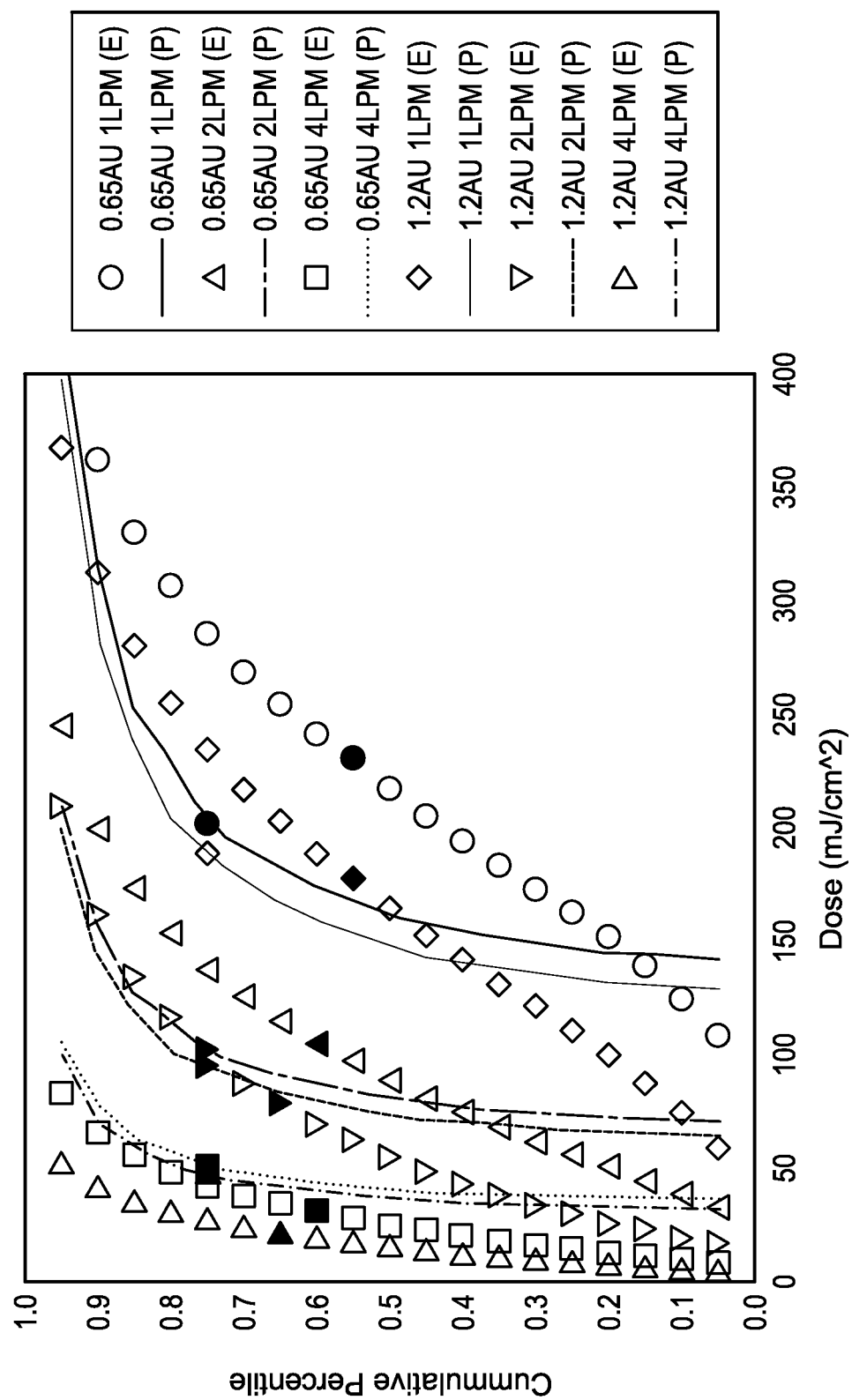
FIG. 13 is a plot showing measured versus predicted dose distributions for Reactor 1.
Figure 14:
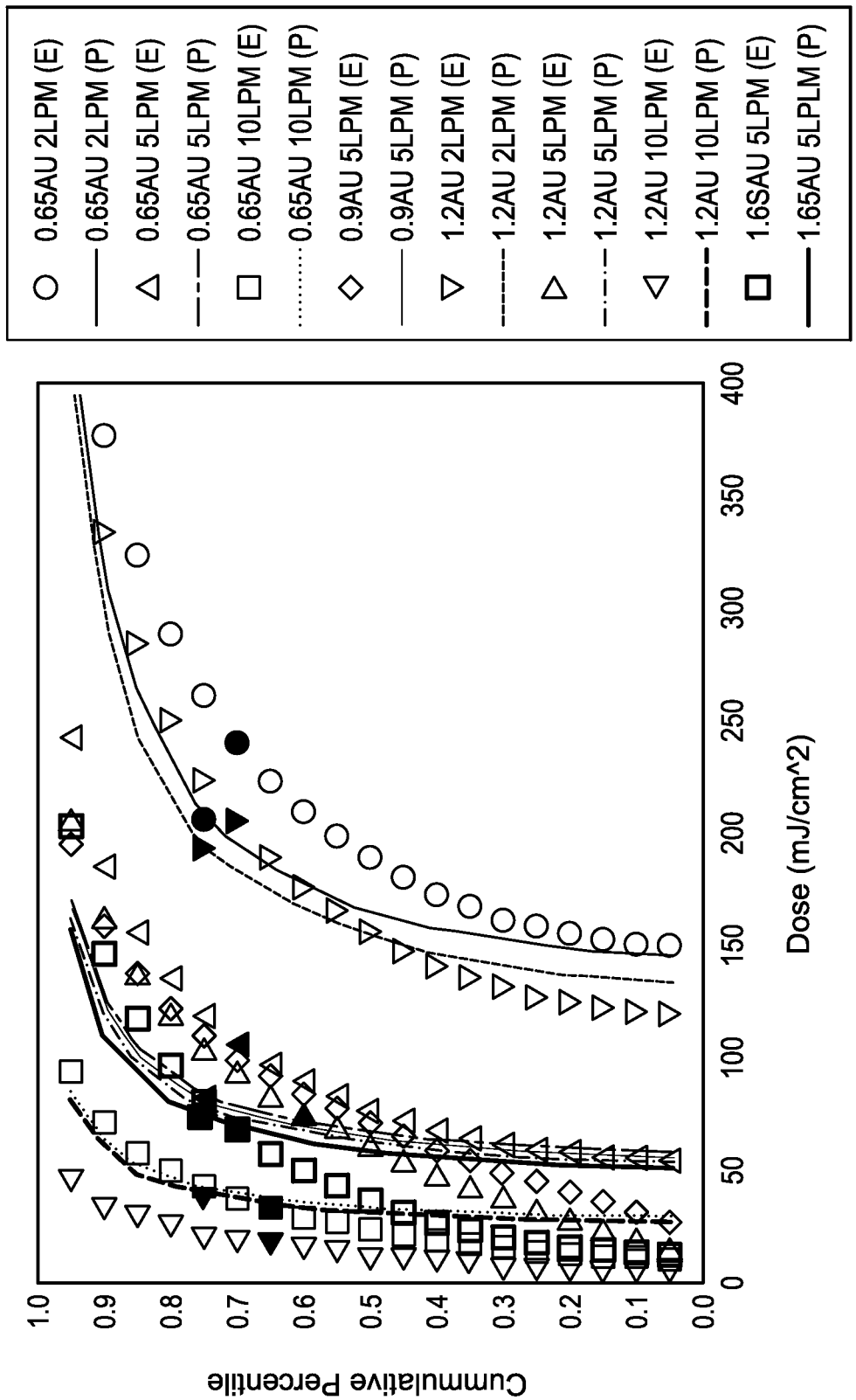
FIG. 14 is a plot showing measured versus predicted dose distributions for Reactor 2.
Figure 15A:
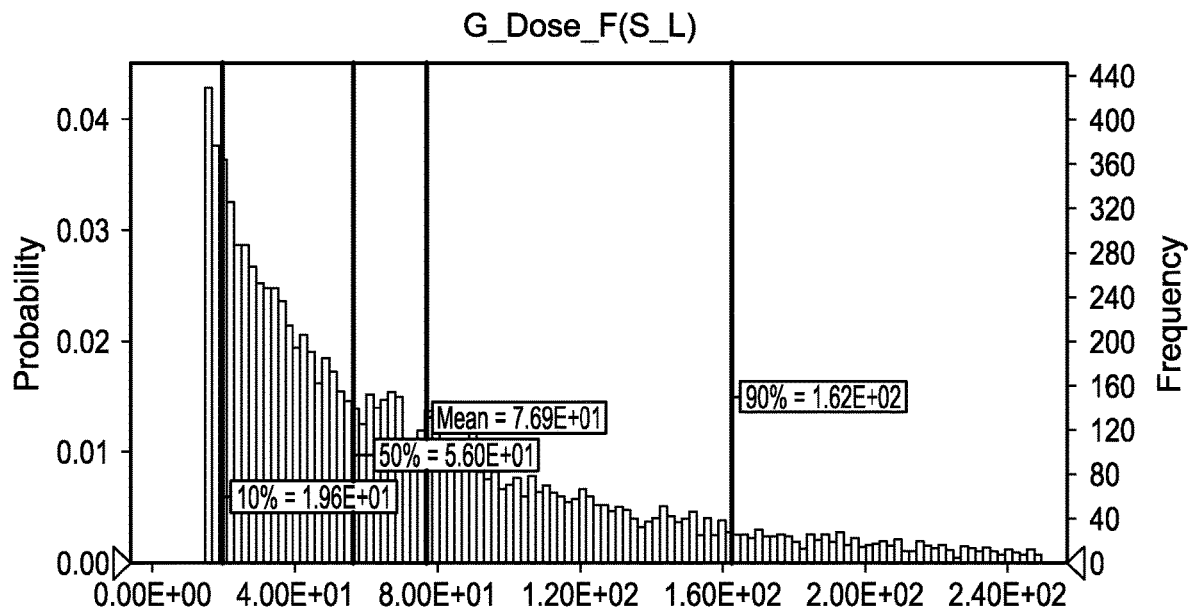
FIG. 15 is a series of plots showing the probability distribution representation of select measured (top) and predicted (bottom) dose distributions for Reactor 1 (left) and Reactor 2 (right).
Figure 15B:
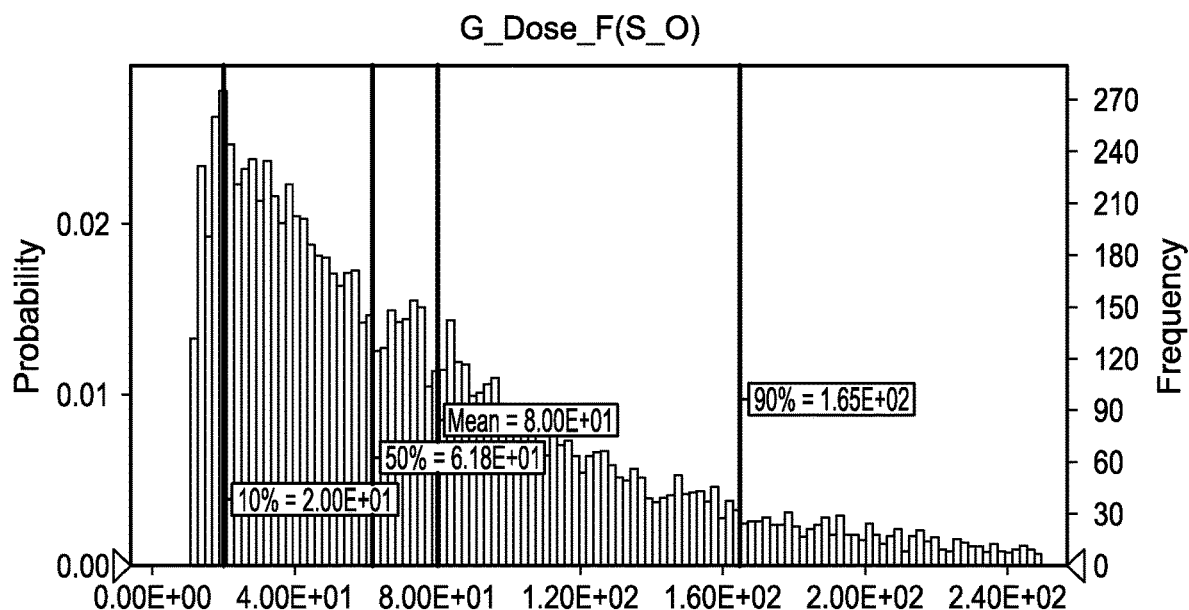
Figure 15C:
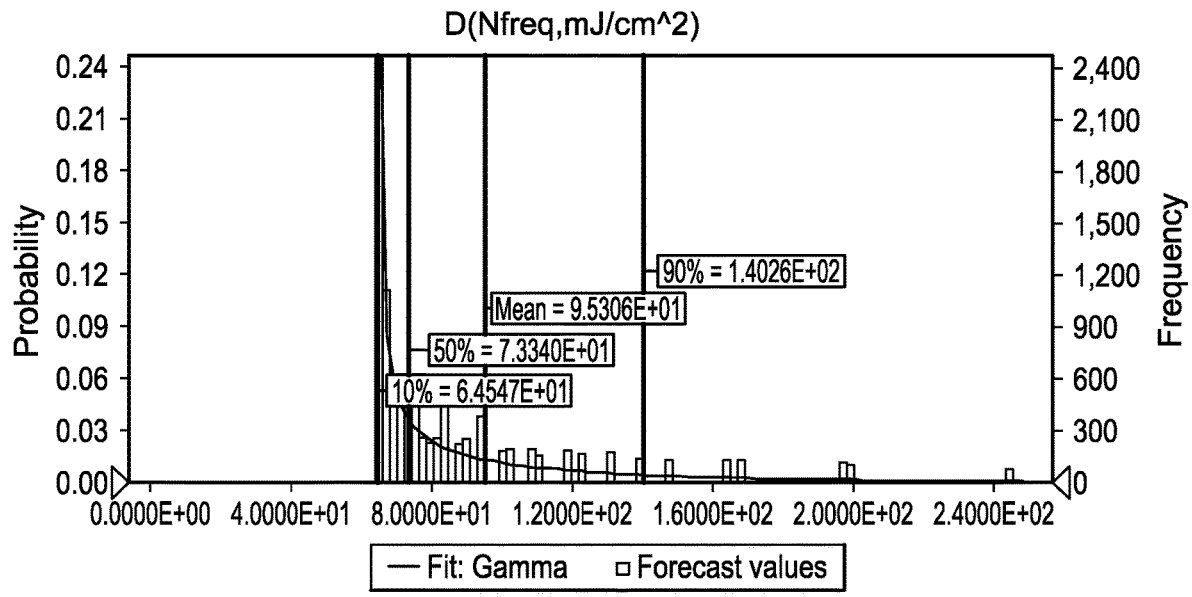
Figure 15D:
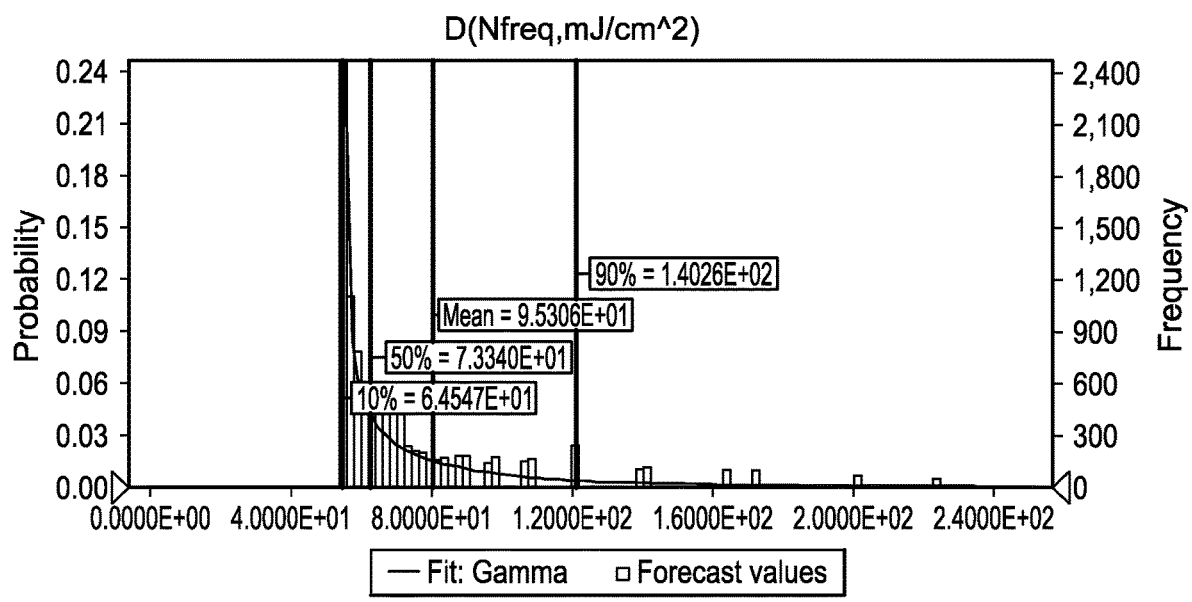
Figure 16A:
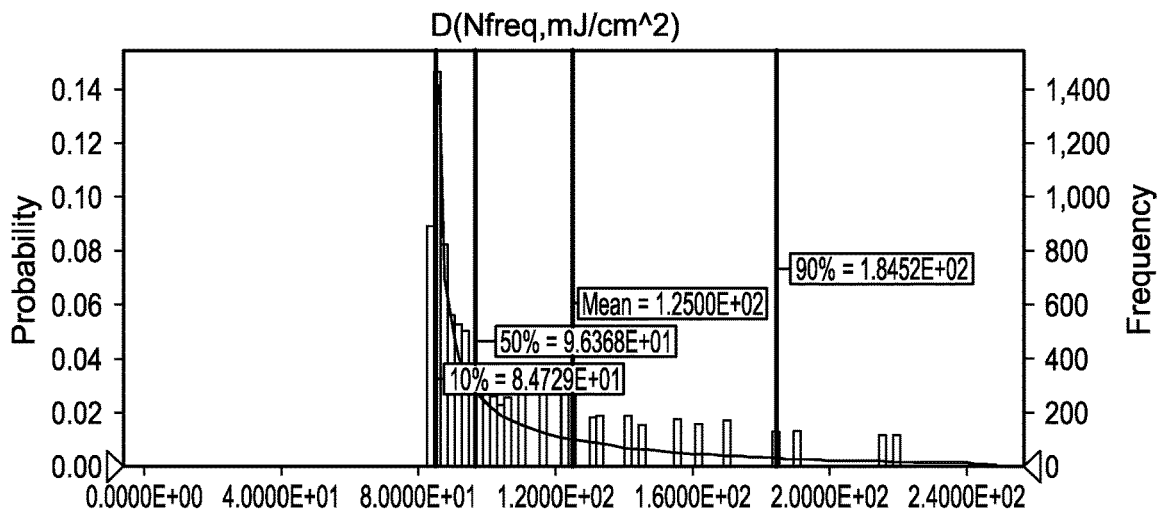
FIG. 16 is a series of plots showing Predicted dose distributions for Media A (FIGS. 16A, 16B), Media B (FIGS. 16C, 16D) and E (FIGS. 16 D, 16E) with flow rates specified for manufacturing (FIGS. 16 A, 16C, 16E) and PC (FIGS. 16B, 16D, 16F).
Figure 16B:
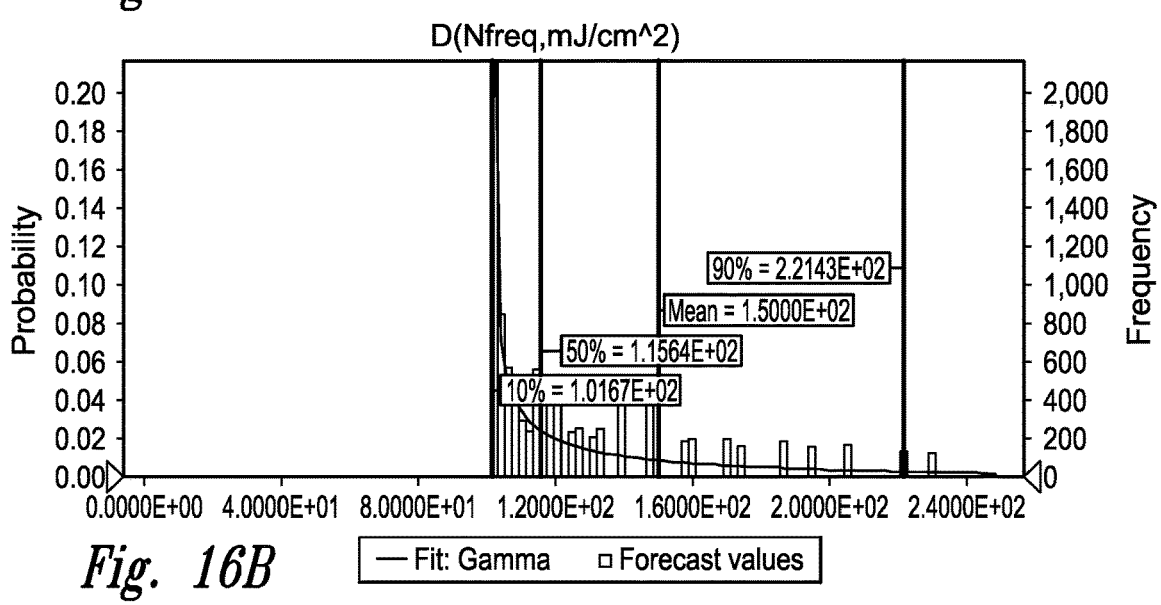
Figure 16C:
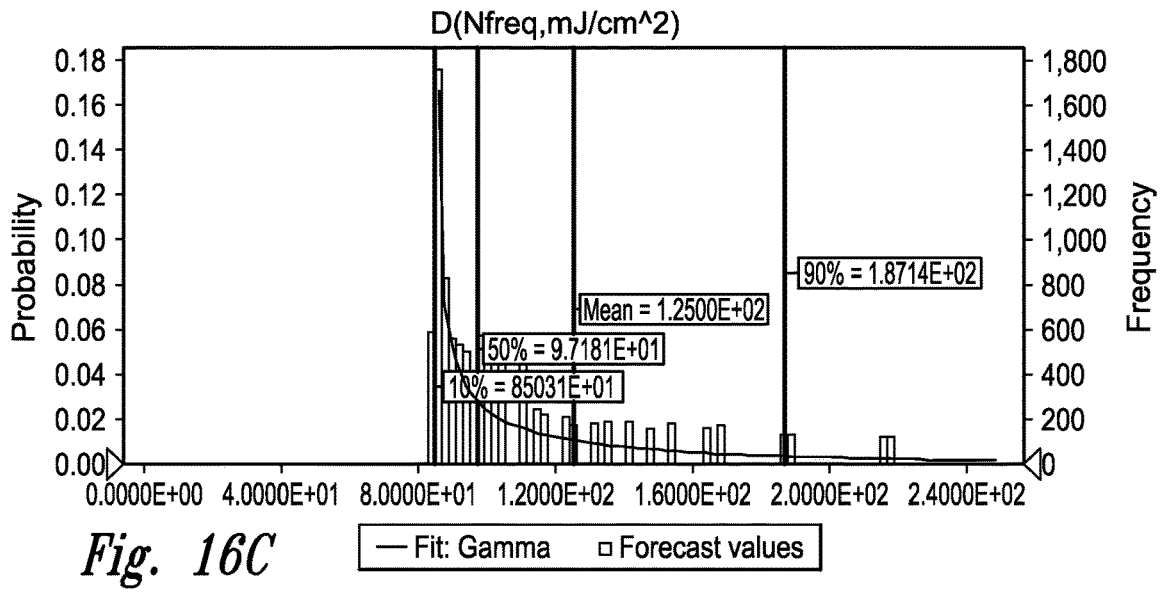
Figure 16D:
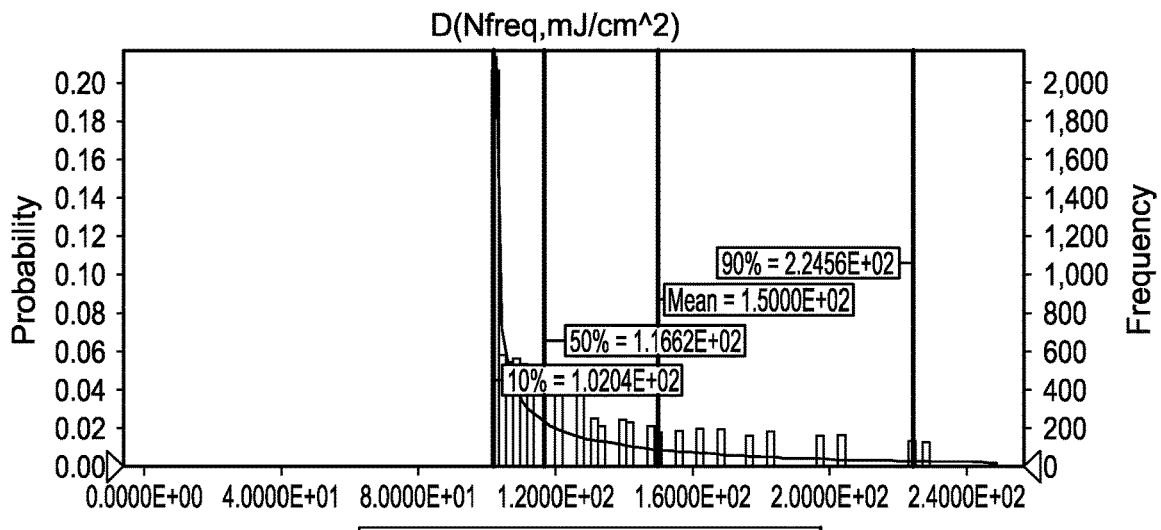
Figure 16E:
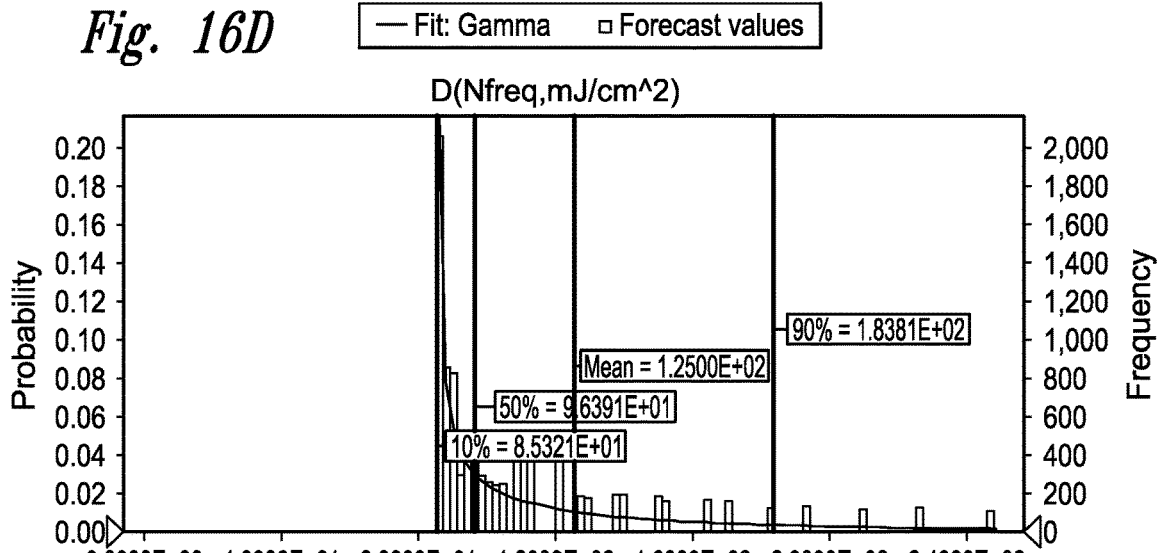
Figure 16F:
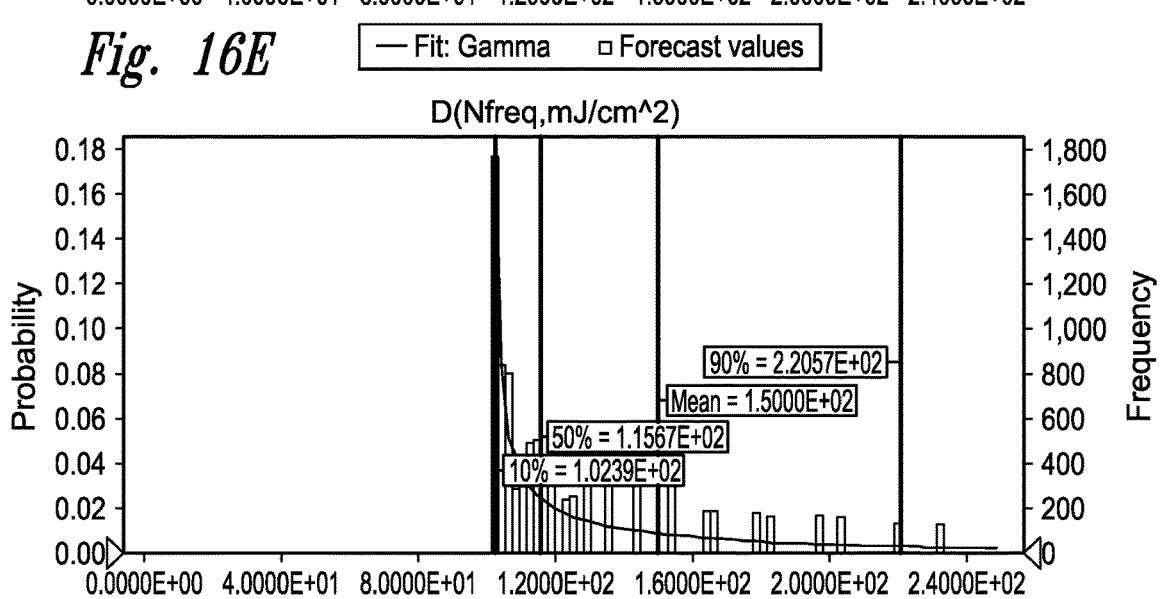

To understand potential differences between prediction and measurement for P10 and P90 dose distribution abstracts, the cumulative probability graphs were compared for the various independent measures. Overlay comparisons for the reactors are shown in FIG. 13 (Reactor 1) and FIG. 14 (Reactor 2), respectively (predicted results are shown as solid lines and experimental results are shown as symbols in both FIGS. 13 and 14).

A comparison of the cumulative probability overlays for Reactor 1 (FIG. 13) reveals that the predicted distributions are more asymmetric than the measured distributions. Specifically, the low-dose side of the predicted distribution rises more sharply than the measured counterpart. Also, the high-dose side of the predicted distribution falls more sharply to the persistent high-dose tail. In general, predicted and measured curves agree more closely at low mean dose than high mean dose. While the dose distribution curves may appear to differ significantly in cases, the dose distribution abstracts need not; this result is evident by comparing values along the 0.5 cumulative percentile line and between the filled symbols representing the mean. In general, predicted distributions do not have the same sensitivity to absorbance as the measured distributions.

A comparison of the cumulative probability overlays for Reactor 2 (FIG. 14) reveals trends similar to those of Reactor 1. An important difference, however, is the agreement between measurement and prediction across the whole of the distribution is visibly better for Reactor 2 than for Reactor 1. As the mechanistic model for the two reactors is the same (excepting parameter values) the difference must arise from differences in the experimental data. Since the mechanistic model represents the ideal reactor (axial uniform flow, etc.), it is reasonable to conclude that Reactor 2 performs more similarly to an ideal annular flow UVC reactor by virtue of its slightly different design.

The distinction in accuracy for the Mean and P50 dose distribution abstracts relative to that for the P10 and P90 abstracts is best illustrated in FIG. 15. While all distributions are consistent with a Generalized Gamma Distribution, the predicted distributions are sharper than the measured distributions. Accurate quantitative prediction of P10 and P90 dose distribution abstracts requires including a bias offset to these values as shown in Table U.

TABLE U

| Bias Corrected Value | Mechanistic Model |
|---|---|
| P10' = P10 − 24 | P10 |
| P50' = P50 | P50 |
| Mean' = Mean | Mean |
| P90' = P90 + 24 | P90 |

Application of Prediction

Several variables which directly affect delivered UVC dose have control bands which may potentially impact the final delivered dose. These operating parameters include the following:

1) Media absorbance—variations in the compounding of individual components can alter the solution at 254 nm;
2) Volumetric flow rate—liquid transfer is under feedback control with a known accuracy;
3) Lamp power—individual mercury lamps produce slightly different amounts of UVC radiation and the lamp output slowly decays with use;
4) Annulus gap width—individual quartz sleeves and stainless steel shells have slightly different diameter dimensions.

To support process characterization, the mechanistic model was used to estimate the dose associated with compounding the effects of these operational parameter variations. Table V contains the operational variation ranges investigated.

TABLE V

| Parameter | Symbol | Mean Value | SI Units | H-Limit | L-Limit |
|---|---|---|---|---|---|
| Parameter Values - Media A | | | | | |
| Media Absorbance | A10 | 1.5299E+00 | unitless | 1.4600E+00 | 1.5997E+00 |
| Volumetric Flow Rate | X | 3.0752E+00 | (Limit) | 3.0137E+00 | 3.1367E+00 |
| Lamp Power | P | 8.2000E+01 | (W) | 8.5280E+00 | 7.4780E+01 |
| Annulus Inner Radius | ri | 1.5010E-02 | (m) | 1.5005E-02 | 1.5015E-02 |
| Annulus Outer Radius | ro | 1.5900-02 | (m) | 1.5975E-02 | 1.5870E-02 |
| Parameter Values - Media B | | | | | |
| Media Absorbance | A10 | 1.2851E+00 | unitless | 1.2264E+00 | 1.3438+00 |
| Volumetric Flow Rate | X | 3.1774E+00 | (Limit) | 3.1139E+00 | 3.2410E+00 |
| Lamp Power | P | 8.2000E+01 | (W) | 8.5280E+00 | 7.4780E+01 |
| Annulus Inner Radius | ri | 1.5010E-02 | (m) | 1.5005E-02 | 1.5015E-02 |
| Annulus Outer Radius | ro | 1.5900-02 | (m) | 1.5975E-02 | 1.5870E-02 |
| Parameter Values - Media E | | | | | |
| Media Absorbance | A10 | 6.7776E-01 | unitless | 6.5271E-01 | 7.0281E-01 |
| Volumetric Flow Rate | X | 3.4547E+00 | (Limit) | 3.3856E+00 | 3.5238+00 |
| Lamp Power | P | 8.2000E+01 | (W) | 8.5280E+00 | 7.4780E+01 |
| Annulus Inner Radius | ri | 1.5010E-02 | (m) | 1.5005E-02 | 1.5015E-02 |
| Annulus Outer Radius | ro | 1.5900-02 | (m) | 1.5975E-02 | 1.5870E-02 |

The resulting dose variance was considered statistically significant if it exceeded the error band previously identified for the fluorescent microsphere assay described in Example 2. To ensure the media degradation risk associated with high dose treatment was properly assessed, the high dose resulting from coincidental variation of all operating parameters (worst-case high dose) was determined. This dose was compared with the statistically significant high dose and used to identify a suitable dose for investigation in Process Characterization.

The computational characterization process used to identify the worst-case high dose in manufacturing and operating parameters to deliver the worst-case dose in process characterization produced the dose distributions shown in FIG. 16A-16F Inspection of FIG. 16 shows that the dose distribution delivered to the different media types (which differ in their A254 values) are highly comparable. Similarly, results show that increasing the mean dose for process characterization (to exceed the worst case-high-dose expected in manufacturing) results in increased values for all dose abstracts. The final Bias Adjusted Dose Abstract values (expressed in mJ/cm$^2$) for manufacturing and process characterization treatment for the three different media types are shown in Table W:

TABLE W

| Media Treatment | Mechanistic Prediction | | | | Bias Corrected Prediction | | | |
|---|---|---|---|---|---|---|---|---|
| | P10 | P50 | Mean | P90 | P10 | P50 | Mean | P90 |
| Man_MediaA | 85 | 96 | 125 | 186 | 61 | 96 | 125 | 209 |
| Man_MediaB | 85 | 97 | 125 | 187 | 61 | 97 | 125 | 211 |
| Man_MediaE | 85 | 96 | 125 | 184 | 61 | 96 | 125 | 208 |
| PC_MediaA | 102 | 116 | 150 | 221 | 78 | 116 | 150 | 245 |
| PC_MediaB | 102 | 117 | 150 | 225 | 78 | 117 | 150 | 249 |
| PC_MediaE | 102 | 116 | 150 | 221 | 78 | 116 | 150 | 245 |

The impact of single parameter variations is always smaller that that arising from all variations—the later being the addition of all of the former. Further, the majority of the potentially important operating variables have specific control mechanisms, including the following:

1) Media absorbance—raw material specifications and compounding procedure
2) Volumetric flow rate—feedback control achieved via a flow meter and flow controller
3) Lamp power—new lamp specifications and electrical power monitoring
4) Annulus gap width—manufacturer specifications, dimensions do not change with use For completeness, the significance of variations in media absorbance was considered computationally. The absorbance required to produce a dose of either 100 or 150 mJ/cm$^2$ (all other operating parameters as specified for a dose of 125 mJ/cm$^2$) is given in Table X. Inspection shows that a variation in the absorbance of the media of this magnitude is not practically possible.

TABLE X

| Dose (mJ/cm$^2$) | 100 | 125 | 150 |
|---|---|---|---|
| Media A | 3.324 | 1.530 | 0.217 |
| Media B | 3.047 | 1.285 | 0.001 |
| Media C | 2.360 | 0.678 | #0.001 |

Actual dose = 138 mJ/cm$^2$

Conclusions From Example 3

The mechanistic model described allows prediction of UVC dose within the confidence interval determined from experimental microsphere determinations for the mean and P50 distribution abstracts. Accurate prediction of P10 and P90 abstracts requires correction for bias offset. Compounding the operating parameter excursions which could contribute to creation of a high dose produced a worst-case dose estimate of approximately 144 mJ/cm$^2$. Use of a dose of 150 mJ/cm$^2$ in process characterization assures the dose is statistically different from the manufacturing target dose and in excess of a normal operation worst-case dose. Simulations show it is not practically possible to exceed the worst-case dose from low media absorbance alone.

References Cited in Example 3

J W Martin et al, "Reciprocity Law Experiments in Polymeric Photodegradation: A Critical Review", *Progress in Organic Coatings*, v. 47, pg. 292-311, (2003)

EPA, United States Environmental Protection Agency, "Ultraviolet Disinfection Guidance Manual for the Final Long-term Enhanced Surface Water Treatment Rule", Office of Water (4601), EPA 815-R-06-007, November (2006)

D Liu, et al, "Evaluation of Alternative Fluence Rate Distribution Models", *J. Water Supply: Res. Tech.-AQUA*, v. 53, pg. 391-408, (2004)

Z Ye, "UV Disinfection Between Concentric Cylinders", Ph.D. dissertation, Georgia Institute of Technology, Pg. 23 (2007)

B R Munson et al, "Steady, Axial, Laminar Flow in an Annulus (sec. 6.9.4)", *Fundamentals of Fluid Mechanics*, J Wiley and Sons, pg 381 (1990)

Example 4

Determination of a Process Reactor UVC Dose

Generating a Standard Curve

A control mixture was prepared by spiking 11.26 microliters of fluorescent bead stock (Polymicrospheres, Indianapolis Ind., fluorescent F114 polystyrene microspheres, particle concentration of $4.44 \times 10^9$) into 50 milliliters of 0.1% SDS solution to achieve a particle concentration of $1 \times 10^6$ particles per ml.

A controlled dose of UVC was delivered by collimated beam reactor to the control mixture containing fluorescent microspheres. The control mixture was exposed to UVC for different accumulated times, with a samples being removed at each of the accumulated times. Accumulated times ranged from 1 to 20 minutes, thus providing samples in which each sample received a correspondingly higher UVC doses from the constant intensity UVC source. The UVC source delivered a fluence rate of 0.3836 mW/cm$^2$. An unexposed sample was used as a control sample. Table Y summarizes the data used to generate the standard curve.

TABLE Y

Beads in 0.1% SDS (start with 30 ml, remove 1 ml at each time point) Visible Light Filter Removed from UVS-28 Lamp

| Minutes | Exposure Time (s) | Avg UV Intensity (mW/cm$^2$) | A254 | $P_1$ | (1-R) | L | d | L/(d + L) | Water Factor | $D_{CB}$ (mJ/cm$^2$) |
|---|---|---|---|---|---|---|---|---|---|---|
| | | | 1e6 beads | | | | | | | |
| 1 | 60 | 0.3836 | 0.0166 | 0.9938 | 0.975 | 50 | 1.276 | 0.9751 | 0.97601 | 21.2 |
| 2 | 120 | 0.3836 | 0.0166 | 0.9938 | 0.975 | 50 | 1.231 | 0.9760 | 0.97684 | 42.5 |
| 3 | 180 | 0.3836 | 0.0166 | 0.9938 | 0.975 | 50 | 1.186 | 0.9768 | 0.97767 | 63.9 |
| 4 | 240 | 0.3836 | 0.0166 | 0.9938 | 0.975 | 50 | 1.141 | 0.9777 | 0.97851 | 85.3 |
| 5 | 300 | 0.3836 | 0.0166 | 0.9938 | 0.975 | 50 | 1.096 | 0.9786 | 0.97934 | 106.9 |
| 6 | 360 | 0.3836 | 0.0166 | 0.9938 | 0.975 | 50 | 1.051 | 0.9794 | 0.98018 | 128.5 |
| 7 | 420 | 0.3836 | 0.0166 | 0.9938 | 0.975 | 50 | 1.006 | 0.9803 | 0.98102 | 150.1 |
| 10 | 600 | 0.3836 | 0.0166 | 0.9938 | 0.975 | 50 | 0.961 | 0.9811 | 0.98186 | 214.8 |
| 15 | 900 | 0.3836 | 0.0166 | 0.9938 | 0.975 | 50 | 0.916 | 0.9820 | 0.98270 | 322.8 |
| 20 | 1200 | 0.3836 | 0.0166 | 0.9938 | 0.975 | 50 | 0.871 | 0.9829 | 0.98354 | 431.2 |

Samples are labeled with date and exposure time 25 minute sample volume is ~14 mL

BEAD SPIKING

| 1000000 | 50000000 | | [=] microspheres in 50 ml |
| | | 0.0112613 | [=]ml bead stock to suspend in 50 ml |

Figure 17:
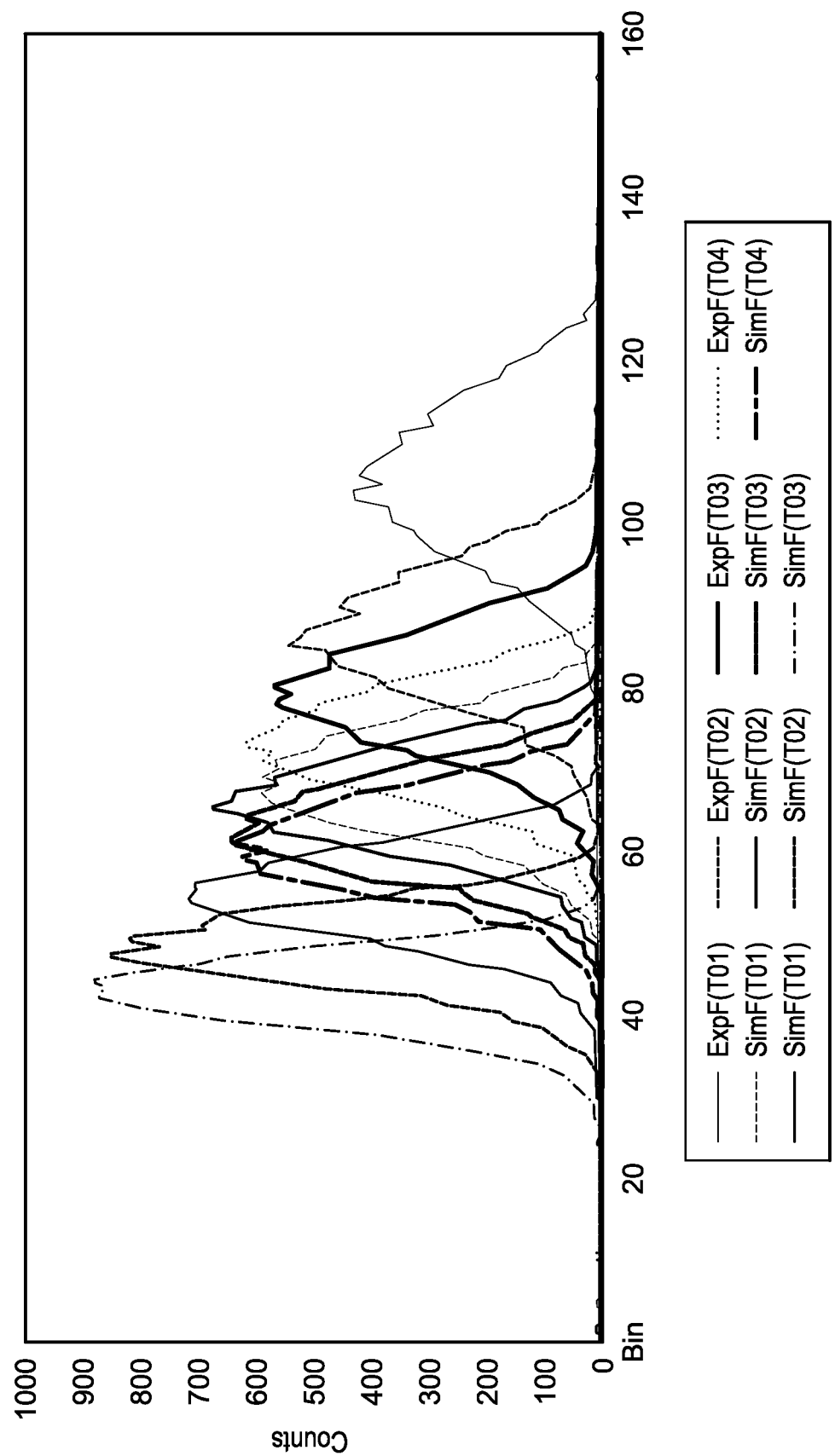
FIG. 17 is a plot showing several microsphere fluorescence distributions resulting from different exposure times as measured by FACS.

The fluorescence distribution of the exposed and control (unexposed) microspheres was measured using a Dako MoFlo™ XDP high speed FACS sorter equipped with a solid state ultraviolet laser for excitation in the UVC range with an emission at 450 nm. Histograms of distributions containing approximately 10,000 counts each are displayed. Sample T0, which corresponds to unexposed microspheres, possesses a fluorescence distribution shown by curve ExpF (T0). Microsphere samples receiving higher doses, culminating in sample T20 which was exposed for 20 minutes, have lower mean fluorescence (corresponding to the BIN number of the mean of the distribution). FIG. 17 shows the fluorescent distribution of the exposed and control microspheres.

Following the measurement of the fluorescent distribution, a mathematical deconvolution was performed in order to determine the photo-bleaching kinetic constants, which are shown in Table Z:

TABLE Z

| Model | | SimF(T0) | SimF(T01) | | |
|---|---|---|---|---|---|
| Assump | MC_F(T0) | 0.00E=00 | | Assumption | Input FACS BIN DATA from DOSE = 0 SAMPLE as custom distribution |
| Variable | Dose | | 2.11E+01 | | Input value for DOSE = X from COLLIMATED BEAM CALCULATIONS sheet |
| Constant | w1 | 2.79E−01 | | Decision | Decision Variable for Optimization |
| Constant | Kb1 | 1.00E+02 | | Decision | Decision Variable for Optimization |
| Constant | Kb2 | 1.4E−03 | | Decision | Decision Variable for Optimization |
| Forecast | Sim_F(T1) | | 0.00E+00 | Forecast | :=MC_F(T0) * (w1 * EXP(Dose*Kb1) + )1 − w1) * EXP (−Dose*Kb2))) |
| Trials | 10000 | | | | Number MC Trials/Simulation = 10,000 (compares with number counts per FACS analysis) |

TABLE Z-continued

| Model | | SimF(T0) | SimF(T01) | | |
|---|---|---|---|---|---|
| Ref Assum | EXP_F(FX) | | 0.00E+00 | Assumption | Input FACS FIN DATA from DOSE = X SAMPLE as custom distribution -Used to product comparator for percentile accuracy |
| Ref Fore | MC_F(X) | 0.00E+00 | 0.00E+00 | Forecast | :=Exp F(TX) - used to produce forecast comparison (experiment − simulation) for percentile accuracy calculation |

Figure 18A:
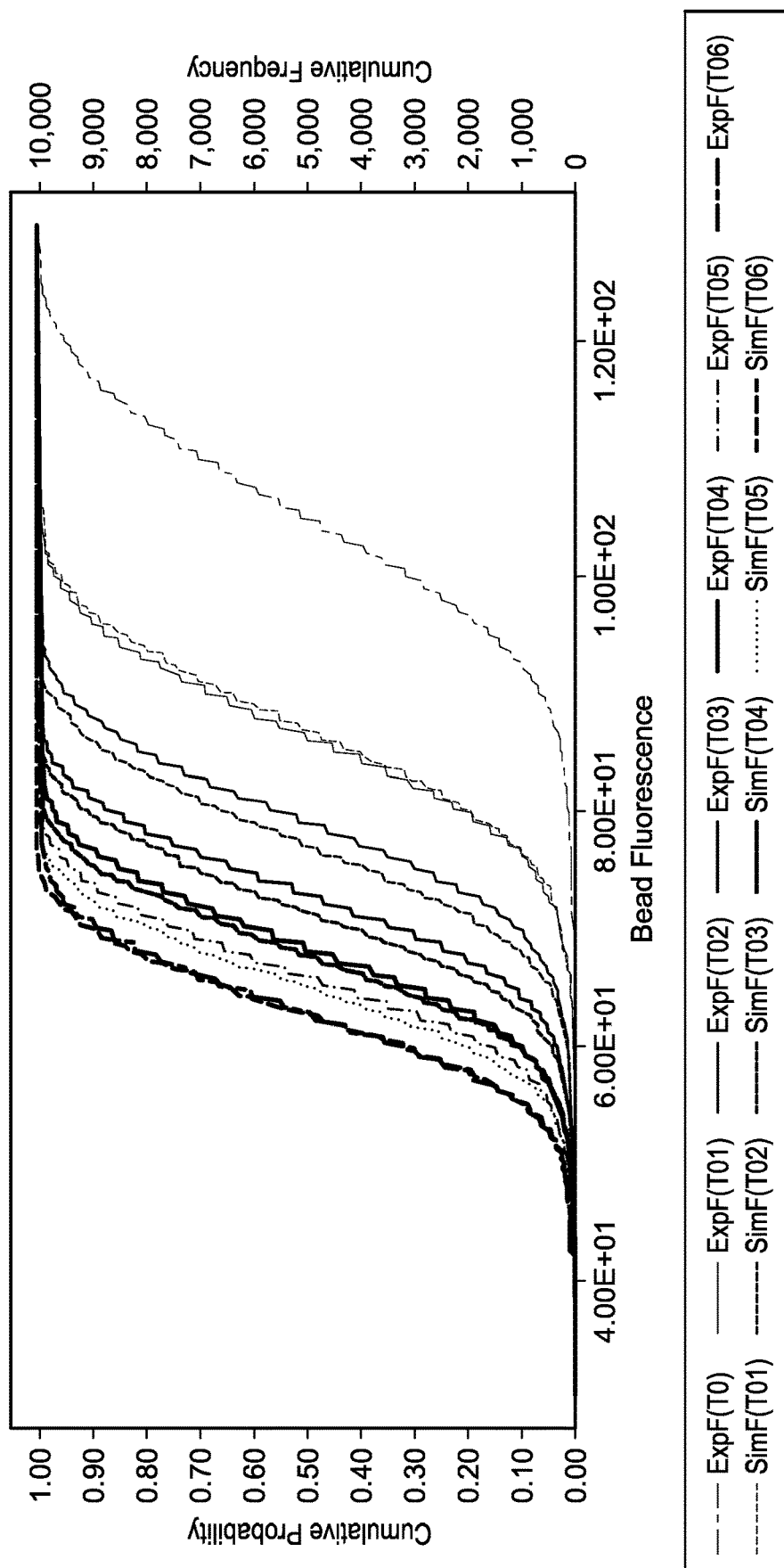
Figure 18B:
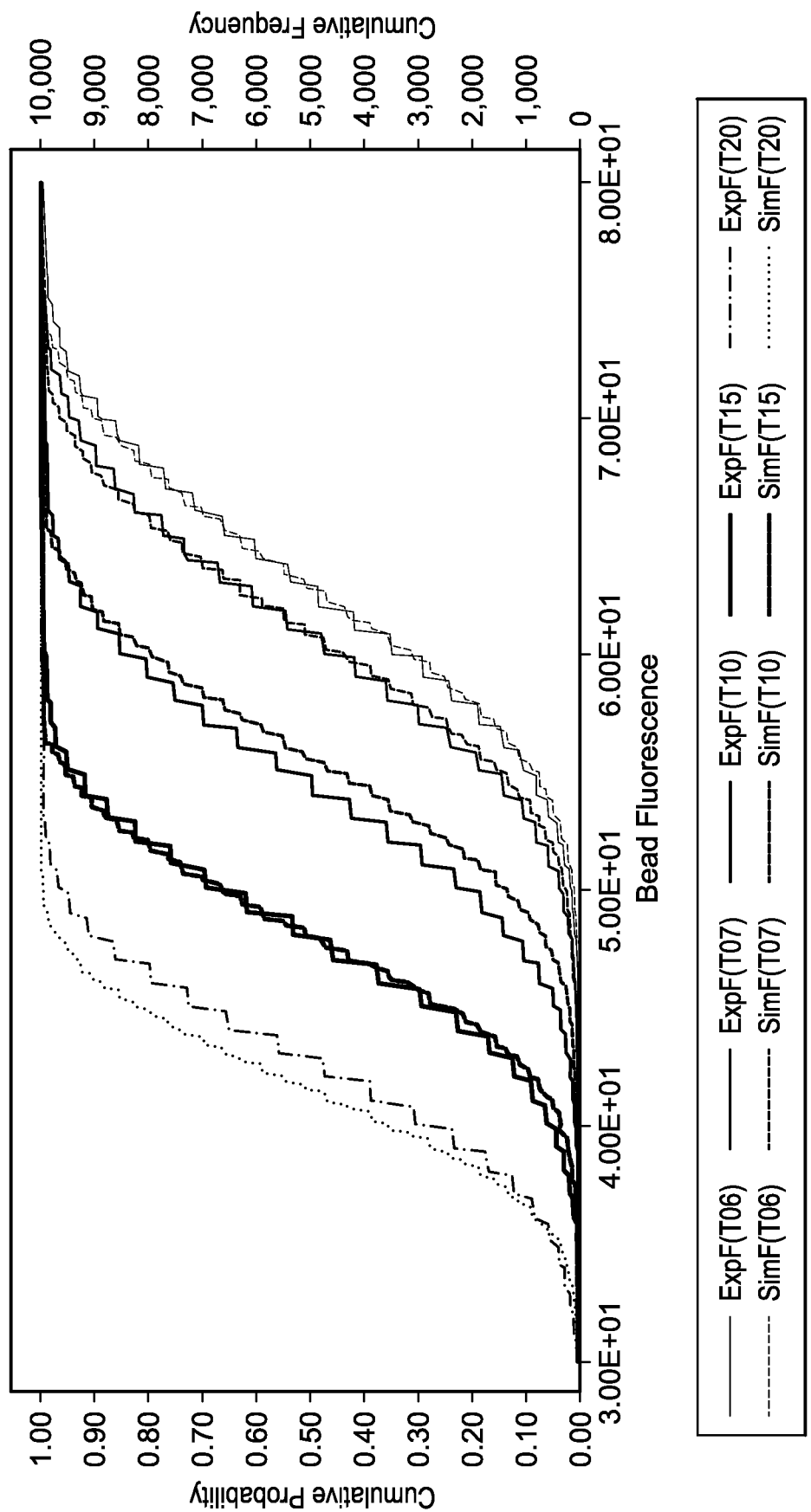
FIG. 18B shows the results for long exposure times producing a high dose UVC experiment versus a simulated distribution.

A comparison of measured fluorescence distributions (dark shade lines) with simulated distributions (light shade lines) produced using optimal bleaching constants. These results are shown in FIGS. 18A and 18B.

Determining Process Reactor Dose Distribution

Next, a mathematical deconvolution was performed in order to determine the dose distribution delivered by the process reactor treatment. The results of that operation are shown in Table AA:

TABLE AA

Dose Distribution Function

| Model | | SinF(T0) | | SimXXX | | |
|---|---|---|---|---|---|---|
| Decision | | | G_Location | 5.25E+00 | Decision | Decision variable for Optimization |
| Decision | | | G_Scale | 1.02E+01 | Decision | Decision variable for Optimization |
| Decision | | | G_Shape | 1.90E+00 | Decision | Decision variable for Optimization |
| Variable | MC_Gdose_XXX | | G_Done | 0.00E+00 | Assump | :=Generalized Gamma Distribution [G_Location, G_Scale, G_Shape] − Stoicastic Dose Parameter |
| Assump | MC_F(T0) | 0.00E+00 | | | Assump | Input FACS BIN DATA from DOSE = 0 SAMPLE as custom distribution |
| Constant | w1 | | | | Input | Result from CB_Kinetics _ Fit |
| Constant | Kb1 | | | | Input | Result from CB_Kinetics _ Fit |
| Constant | Kb2 | | | | Input | Result from CB_Kinetics _ Fit |
| Forecast | Sim_F(XXX) | | 0.00E+00 | | Forecast | :=MC_F(T0)* (w1 * EXP (−MC_ GDoseXXX]* $Kb^1$) + (1 − w1) *EXP(−(MC_GDoseXXX]*$Kb^2$) |
| Forecast | Sim_Dose(XXX) | | 0.00E+00 | | Forecast | :=MC_Gdose _XXX - used to produce forecast from assumption - allows calculation of abstracts for dose percentiles |
| Rel Assum | Exp_F(XXX) | | 0.00E+00 | | Assump | Input FACS BIN DATA from sample XXX as custom distribution - Used to produce comparator for percentile accuracy calculations |
| Rel Fore | MC_F(XXX) | 0.00E+00 | 0.00E+00 | | Forecast | :=Exp_F(TX) - used to produce forecast from assumption - allows comparison (equipment − simulation) for percentile accuracy calculation |

Figure 19A:
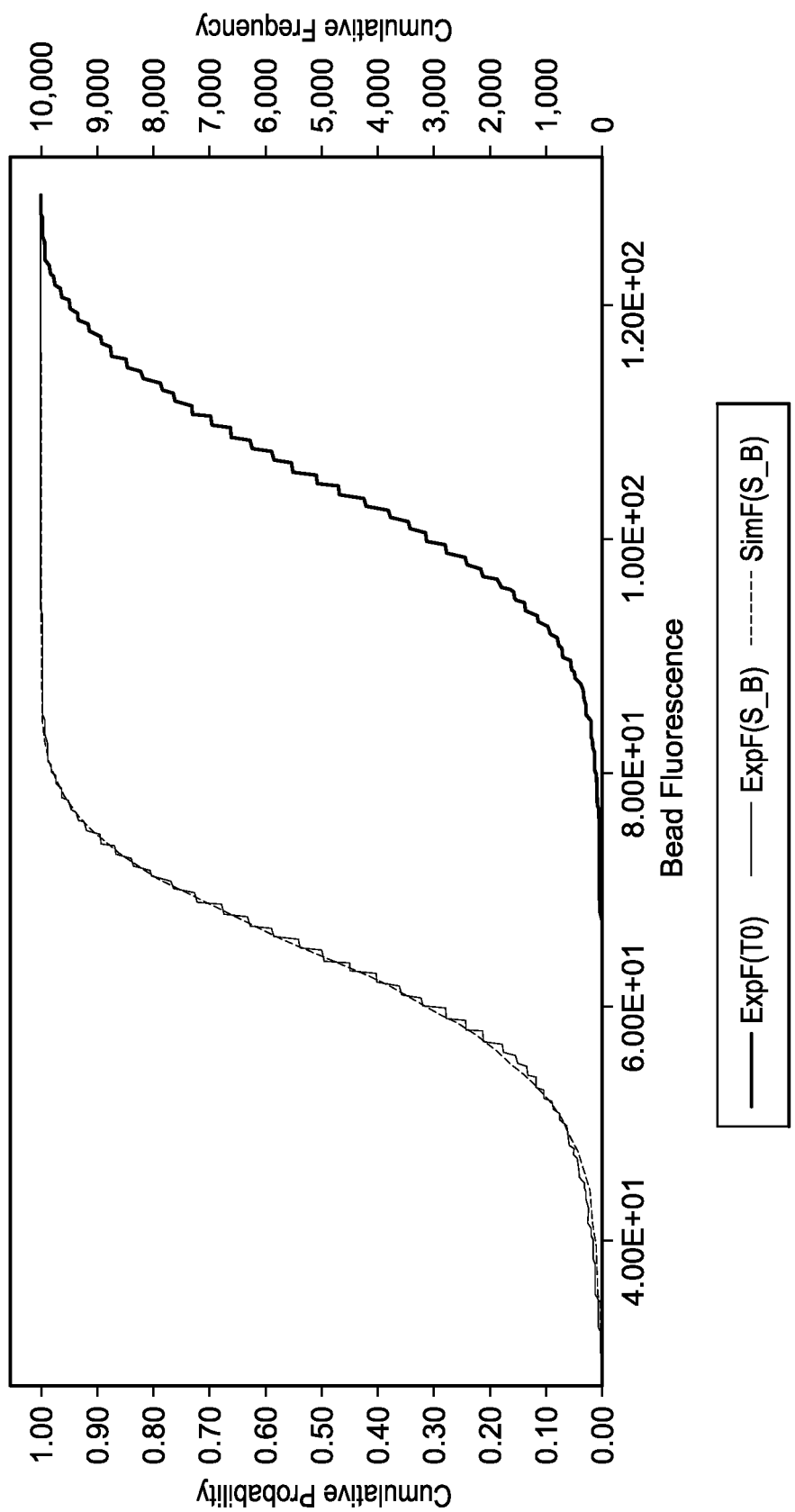
Figure 19B:
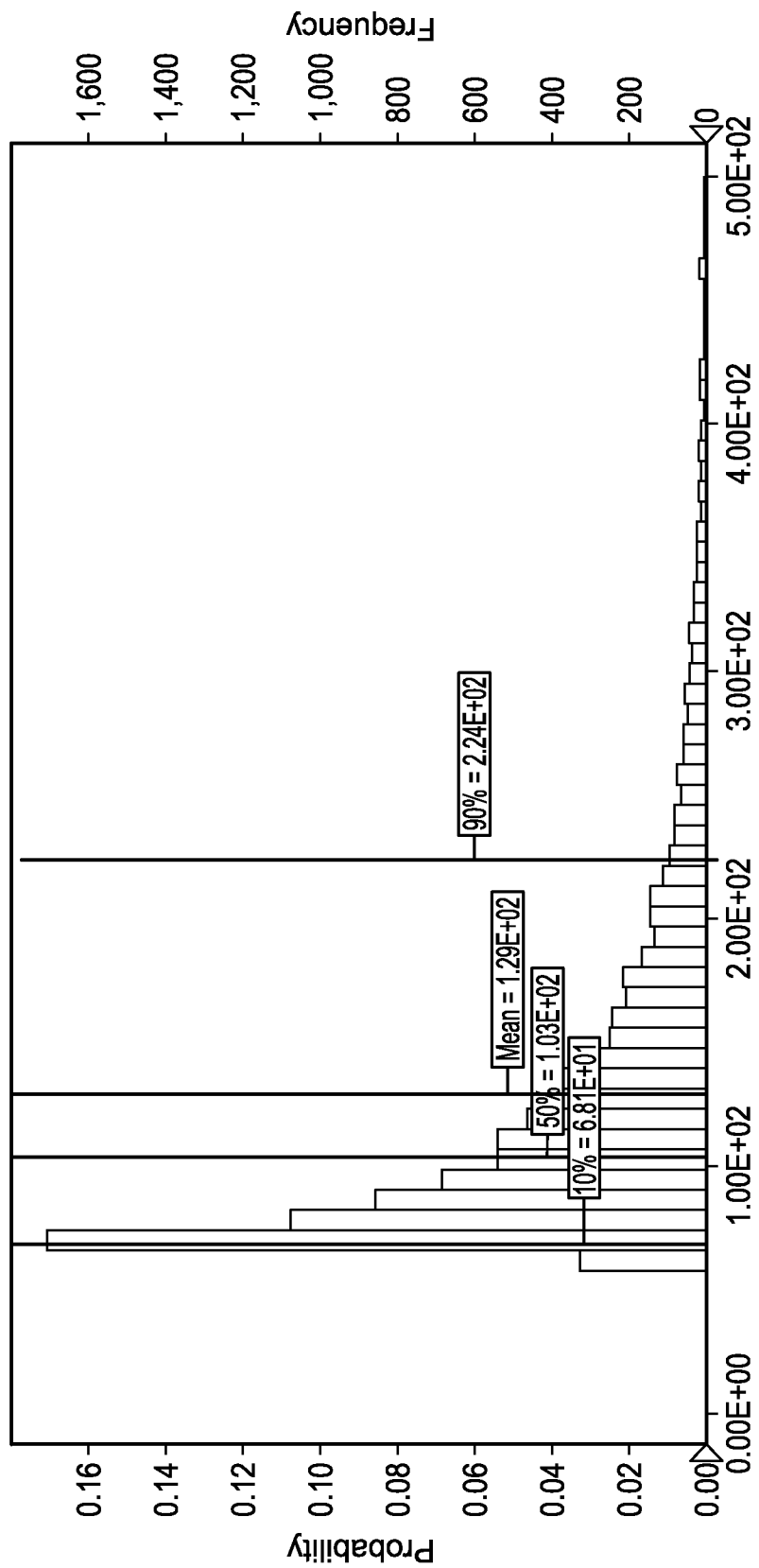
FIG. 19B shows the associated dose distribution represented by the generalized gamma distribution.

A comparison of measured fluorescence distributions was then performed and is shown in FIGS. 19A-19B. In FIG. 19A the measured fluorescence distribution (dark shade grey line) was compared with the simulated distribution (light shade grey line); an untreated microsphere fluorescence distribution is included for reference (black line). In FIG. 19B, the dose distribution prodiced by passage through the process reactor and determined by the simulation procedure described is shown.

Example 5

Determination of Microsphere Bleaching Kinetic Constants in Complex Media Solutions Generating a Standard Curve Control mixtures were prepared by spiking microspheres into (A) 0.1% SDS solution, (B) Cell Culture Media, and (C) Fetal Bovine Serum. The separate control mixtures were exposed to a series of controlled doses of UVC per methods described in Examples 1 and 4. Tables BB, CC, and DD summarize the data used to generate the standard curves for SDS solution, Cell Culture Media, and FBS, respectively. As observed in Tables BB, CC, DD, increasing degree of absorbance results in attenuated degree of dose received.

TABLE BB

Beads in 0.1% SDS (start with 30 ml, remove 1 ml at each time point) Visible Light Filter Removed from UVS-28 Lamp

| Minutes | Exposure Time (s) | Avg UV Intensity (mW/cm$^2$) | A254 | $P_1$ | (1-R) | L | d | L/(d + L) | Water Factor | $D_{CB}$ (mJ/cm$^2$) |
|---|---|---|---|---|---|---|---|---|---|---|
|  |  |  | 1e6 beads |  |  |  |  |  |  |  |
| 1 | 60 | 0.4022 | 0.0166 | 1.000 | 0.975 | 50 | 1.276 | 0.9751 | 0.97601 | 22.4 |
| 2 | 120 | 0.4022 | 0.0166 | 1.000 | 0.975 | 50 | 1.231 | 0.9760 | 0.97684 | 44.9 |
| 3 | 180 | 0.4022 | 0.0166 | 1.000 | 0.975 | 50 | 1.186 | 0.9768 | 0.97767 | 67.4 |
| 4 | 240 | 0.4022 | 0.0166 | 1.000 | 0.975 | 50 | 1.141 | 0.9777 | 0.97851 | 90.0 |
| 5 | 300 | 0.4022 | 0.0166 | 1.000 | 0.975 | 50 | 1.096 | 0.9786 | 0.97934 | 112.7 |
| 6 | 360 | 0.4022 | 0.0166 | 1.000 | 0.975 | 50 | 1.051 | 0.9794 | 0.98018 | 135.5 |
| 7 | 420 | 0.4022 | 0.0166 | 1.000 | 0.975 | 50 | 1.006 | 0.9803 | 0.98102 | 158.4 |
| 10 | 600 | 0.4022 | 0.0166 | 1.000 | 0.975 | 50 | 0.961 | 0.9811 | 0.98186 | 226.7 |
| 15 | 900 | 0.4022 | 0.0166 | 1.000 | 0.975 | 50 | 0.916 | 0.9820 | 0.98270 | 340.6 |
| 20 | 1200 | 0.4022 | 0.0166 | 1.000 | 0.975 | 50 | 0.871 | 0.9829 | 0.98354 | 454.9 |

TABLE CC

Beads in Media (start with 30 ml, remove 1 ml at each time point) Visible Light Filter Removed from UVS-28 Lamp

| Minutes | Exposure Time (s) | Avg UV Intensity (mW/cm$^2$) | A254 | $P_1$ | (1-R) | L | d | L/(d + L) | Water Factor | $D_{CB}$ (mJ/cm$^2$) |
|---|---|---|---|---|---|---|---|---|---|---|
|  |  |  | 1e6 beads |  |  |  |  |  |  |  |
| 1 | 60 | 0.395 | 1.19 | 1.000 | 0.975 | 50 | 1.276 | 0.9751 | 0.27735 | 6.2 |
| 2 | 120 | 0.395 | 1.19 | 1.000 | 0.975 | 50 | 1.231 | 0.9760 | 0.28630 | 12.9 |
| 3 | 180 | 0.395 | 1.19 | 1.000 | 0.975 | 50 | 1.186 | 0.9768 | 0.29578 | 20.0 |
| 4 | 240 | 0.395 | 1.19 | 1.000 | 0.975 | 50 | 1.141 | 0.9777 | 0.30582 | 27.6 |
| 5 | 300 | 0.395 | 1.19 | 1.000 | 0.975 | 50 | 1.096 | 0.9786 | 0.31646 | 35.8 |
| 6 | 360 | 0.395 | 1.19 | 1.000 | 0.975 | 50 | 1.051 | 0.9794 | 0.32775 | 44.5 |
| 7 | 420 | 0.395 | 1.19 | 1.000 | 0.975 | 50 | 1.006 | 0.9803 | 0.33974 | 53.9 |
| 10 | 600 | 0.395 | 1.19 | 1.000 | 0.975 | 50 | 0.961 | 0.9811 | 0.35248 | 79.9 |
| 15 | 900 | 0.395 | 1.19 | 1.000 | 0.975 | 50 | 0.916 | 0.9820 | 0.36604 | 124.6 |
| 20 | 1200 | 0.395 | 1.19 | 1.000 | 0.975 | 50 | 0.871 | 0.9829 | 0.36048 | 172.8 |

TABLE DD

Beads in FBS (start with 30 ml, remove 1 ml at each time point) Visible Light Filter Removed from UVS-28 Lamp

| Minutes | Exposure Time (s) | Avg UV Intensity (mW/cm$^2$) | A254 | P$_1$ | (1-R) | L | d | L/(d + L) | Water Factor | D$_{CB}$ (mJ/cm$^2$) |
|---|---|---|---|---|---|---|---|---|---|---|
| | | | 1e6 beads | | | | | | | |
| 1 | 60 | 0.3962 | 4.2 | 1.000 | 0.975 | 50 | 1.276 | 0.9751 | 0.08104 | 1.8 |
| 2 | 120 | 0.3962 | 4.2 | 1.000 | 0.975 | 50 | 1.231 | 0.9760 | 0.08400 | 3.8 |
| 3 | 180 | 0.3962 | 4.2 | 1.000 | 0.975 | 50 | 1.186 | 0.9768 | 0.08719 | 5.9 |
| 4 | 240 | 0.3962 | 4.2 | 1.000 | 0.975 | 50 | 1.141 | 0.9777 | 0.09062 | 8.2 |
| 5 | 300 | 0.3962 | 4.2 | 1.000 | 0.975 | 50 | 1.096 | 0.9786 | 0.09434 | 10.7 |
| 6 | 360 | 0.3962 | 4.2 | 1.000 | 0.975 | 50 | 1.051 | 0.9794 | 0.09838 | 13.4 |
| 7 | 420 | 0.3962 | 4.2 | 1.000 | 0.975 | 50 | 1.006 | 0.9803 | 0.10278 | 16.3 |
| 10 | 600 | 0.3962 | 4.2 | 1.000 | 0.975 | 50 | 0.961 | 0.9811 | 0.10759 | 24.5 |
| 15 | 900 | 0.3962 | 4.2 | 1.000 | 0.975 | 50 | 0.916 | 0.9820 | 0.11287 | 38.5 |
| 20 | 1200 | 0.3962 | 4.2 | 1.000 | 0.975 | 50 | 0.871 | 0.9829 | 0.11869 | 54.1 |

Figure 20:
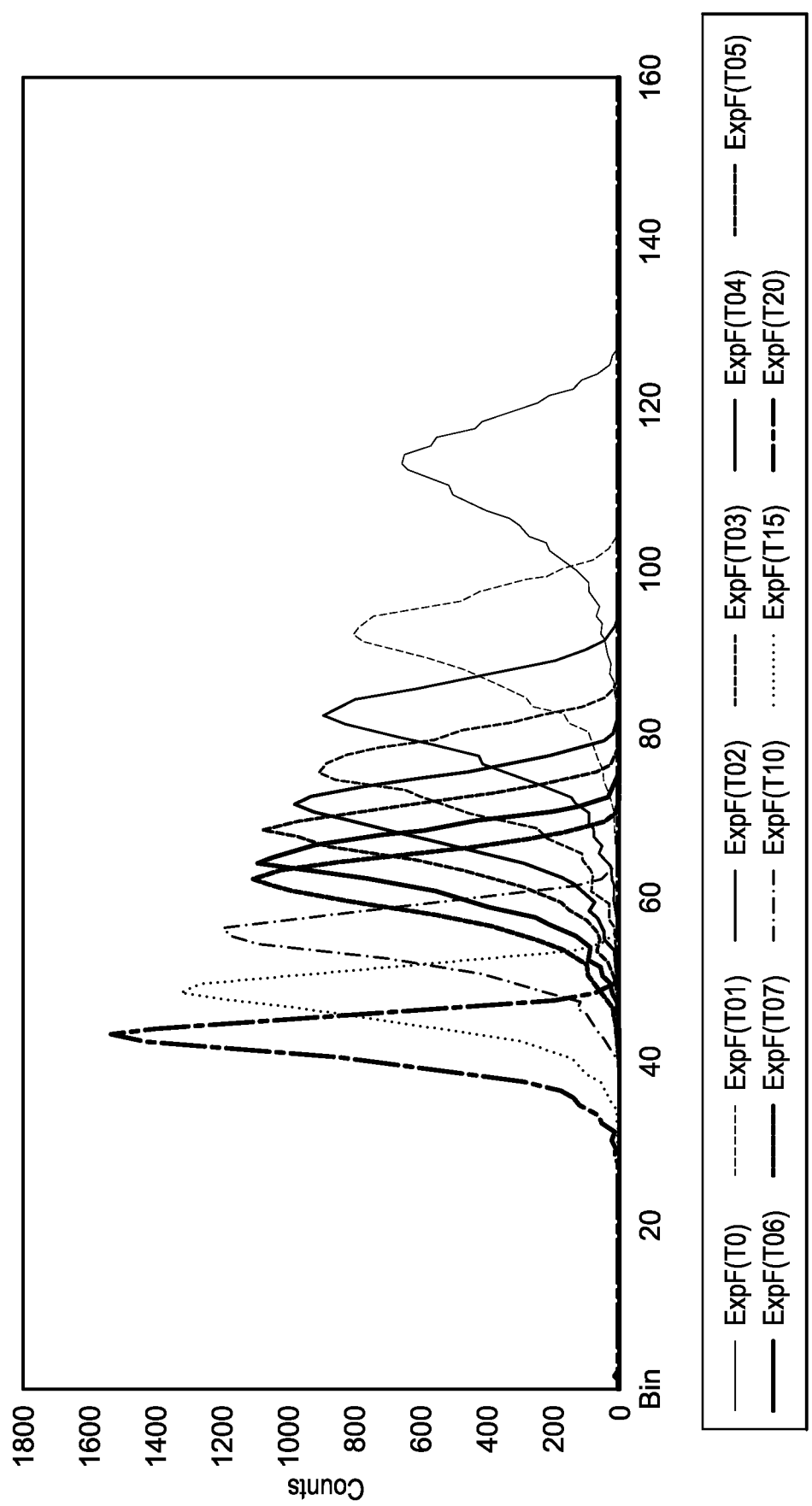
FIG. 20 is a plot showing overlay fluorescence distributions as measured by FACS wherein samples were derived from treatment of microspheres in SDS solution with various residence time exposures with a collimated beam device.
Figure 22:
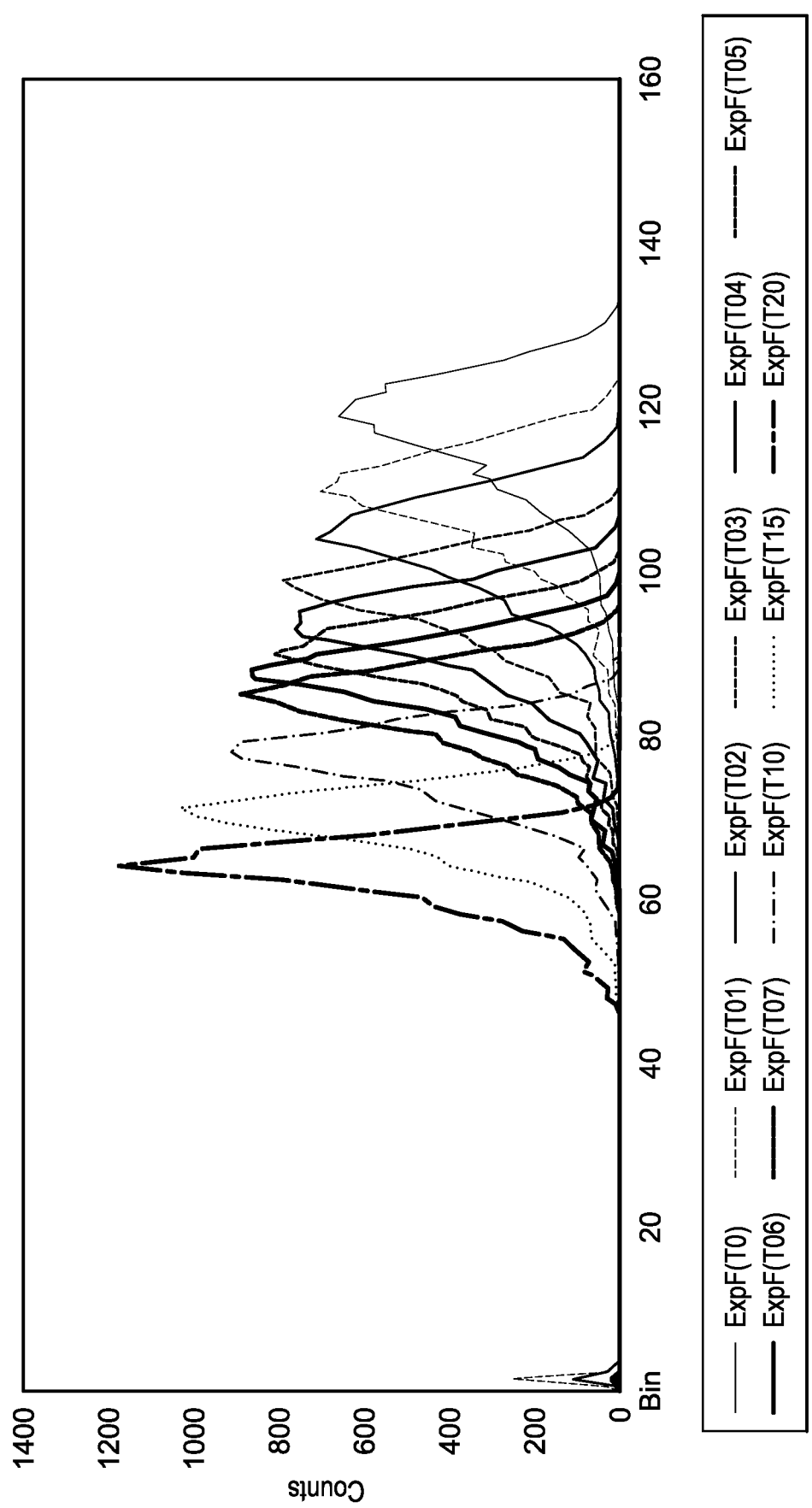
FIG. 22 is a plot showing overlay fluorescence distributions as measured by FACS wherein samples were derived from treatment of microspheres in culture media with various residence time exposures with a collimated beam device.
Figure 24:
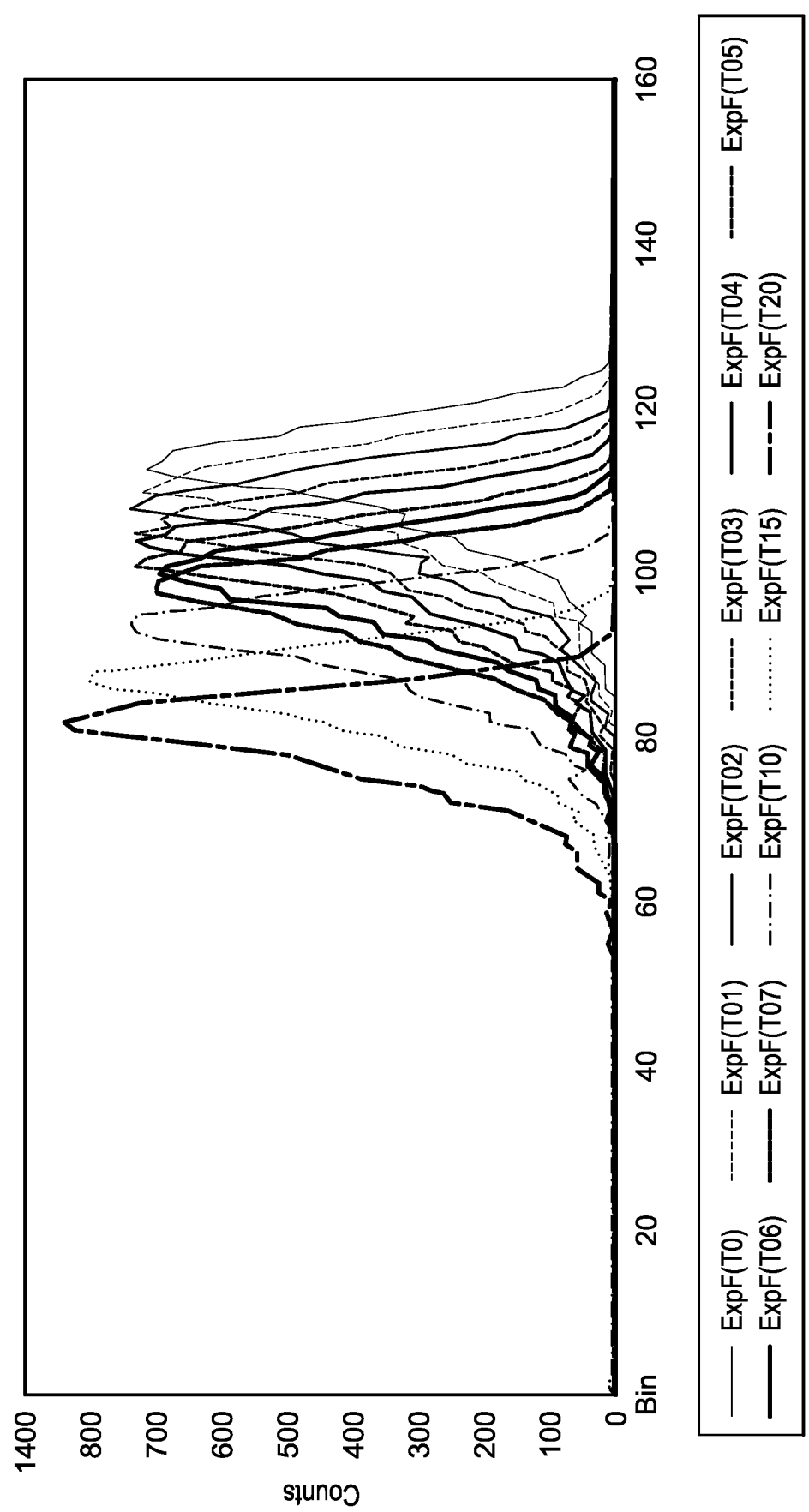
FIG. 24 is a plot showing overlay fluorescence distributions as measured by FACS wherein samples were derived from treatment of microspheres in fetal bovine serum (FBS) with various residence time exposures with a collimated beam device.

The fluorescence distributions of the exposed and control (unexposed) microspheres contained in the SDS solution, Cell Culture Media, and FBS were obtained by FACS analysis as described in Examples 1 and 4 and are shown in FIGS. 20, 22, and 24 respectively. As observed in FIGS. 20, 22, and 24, increasing optical absorbance results in attenuated degree of dose received which results in reduced extent of microsphere bleaching.

Figure 21:
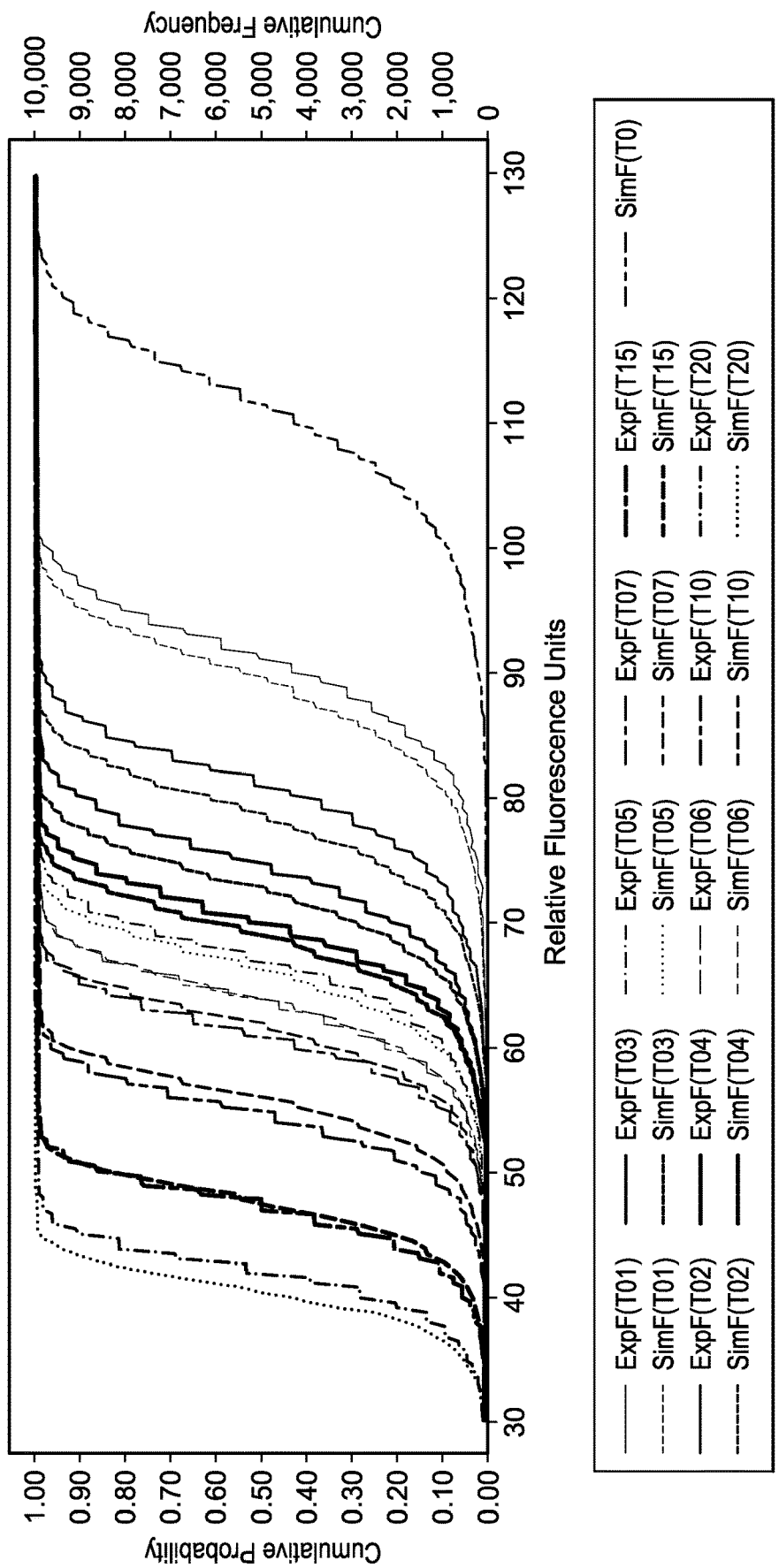
FIG. 21 is a plot showing a comparison of measured fluorescence distributions (dark shade lines) with simulated distributions (light shade lines) produced using optimal bleaching constants for exposure of microspheres in SDS solution.
Figure 23:
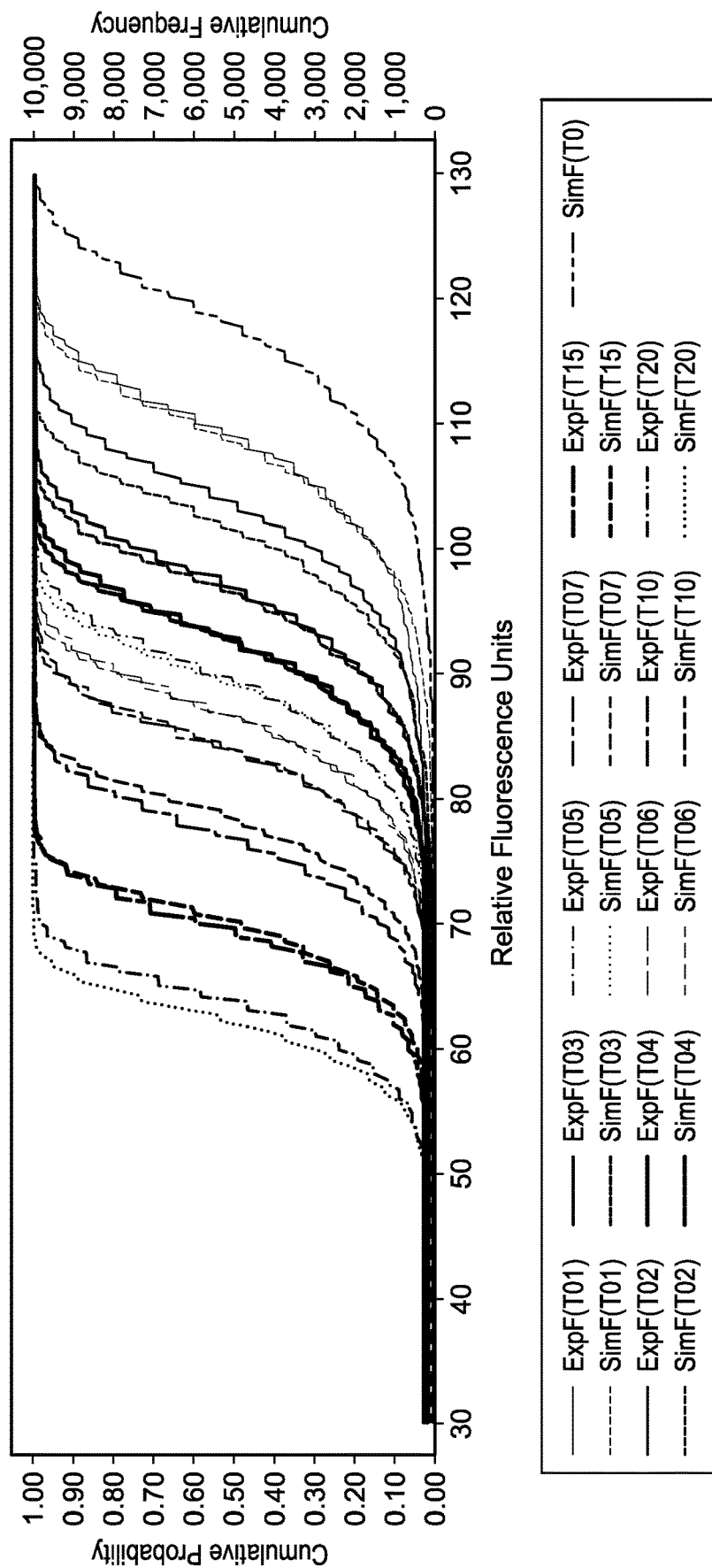
FIG. 23 is a plot showing a comparison of measured fluorescence distributions (dark shade lines) with simulated distributions (light shade lines) produced using optimal bleaching constants for exposure of microspheres in culture medium.
Figure 25:
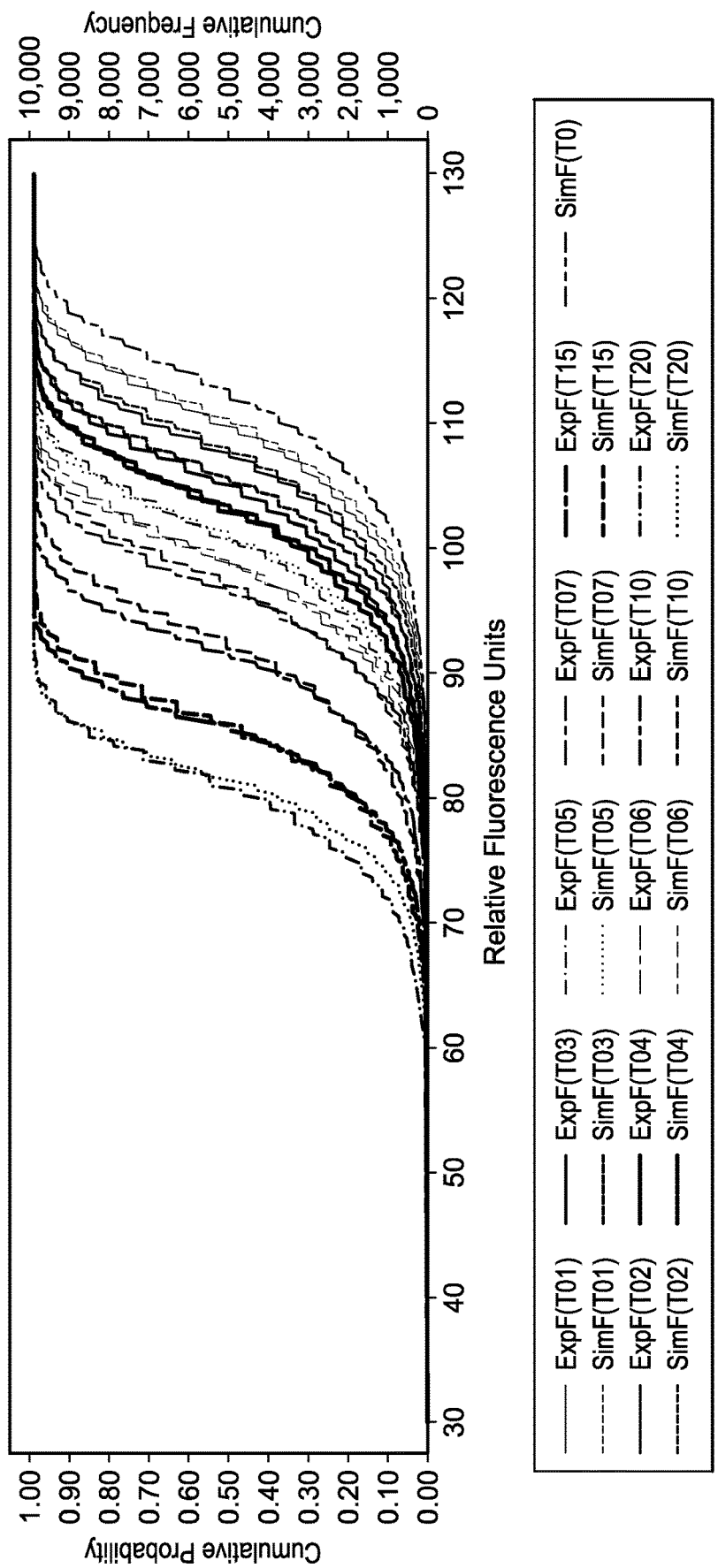
FIG. 25 is a plot showing a comparison of measured fluorescence distributions (dark shade lines) with simulated distributions (light shade lines) produced using optimal bleaching constants for exposure of microspheres in fetal bovine serum.

Following the measurement of the fluorescent distribution, a mathematical deconvolution was performed in order to determine the photo-bleaching kinetic constants. The methods employed in the deconvolution are described in Example 2. Comparison of the measured fluorescence distributions with simulated distributions using optimum bleaching kinetic constants for microspheres contained in the SDS solution, Cell Culture Media, and FBS are shown in FIGS. 21, 23, and 25, respectively. The measured and simulated distributions for complex high optically absorbing solutions, represented by culture media and fetal bovine serum, are comparably accurate as those for low optically absorbing solutions, represented by SDS solutions.

The quantitative values for microsphere bleaching-kinetic parameters were determined using the deconvolution procedures described in Example 2 and are shown in Table EE. Importantly, the quantitative values for the bleaching-kinetic parameters are essentially the same for bleaching in the complex high optically-absorbing solutions, represented by culture media and fetal bovine serum, as they are in low optical-absorbing simple solutions, represented by SDS solution.

TABLE EE

| Fluid | Measure | F(T0) | Kb1 | Kb2 | w1 |
|---|---|---|---|---|---|
| SDS | Mean | 1.1E+02 | 3.4E-02 | 1.4E-03 | 3.1E-01 |
| | Std Dev | 9.6E+00 | 3.9E-03 | 4.5E-05 | 6.4E-03 |
| Media | Mean | 1.2E+02 | 6.5E-02 | 2.4E-03 | 2.0E-01 |
| | Std Dev | 8.9E+00 | 1.0E-02 | 4.7E-05 | 9.1E-03 |
| FBS | Mean | 1.1E+02 | 3.4E-02 | 2.6E-04 | 3.3E-01 |
| | Std Dev | 9.6E+00 | 2.1E-03 | 1.4E-04 | 1.3E-02 |

Example 6

Determination of Microsphere Bleaching Kinetic Constants in Complex Protein Solutions Generating a Standard Curve Control mixtures were prepared by spiking microspheres into (A) 0.1% SDS solution, (B) protein-A purified monoclonal antibody (Mab) in filtered viral inactivated pool (FVIP), and (C) protein-A purified Mab in FVIP supplemented with the UVC protectant tyrosine. The separate control mixtures were exposed to a series of controlled doses of UVC per methods described in Examples 1 and 4. Tables FF, GG, and HH summarize the data used to generate the standard curves for SDS solution, protein-A purified Mab in FVIP, and protein-A purified Mab in FVIP supplemented with tyrosine, respectively. In this experiment, the residence time of exposure was adjusted based on the optical absorbance of the fluid so as to deliver a consistent set of doses between the different fluids. This adjusted time is referred to as "Theoretical Exposure Time for Material" in tables GG and HH.

TABLE FF

Beads in 0.1% SDS (start with 30 ml, remove 1 ml at each time point) Visible Light Filter Removed from UVS-28 Lamp

| Minutes | Exposure Time (s) | Avg UV Intensity (mW/cm$^2$) | A254 | P$_1$ | (1-R) | L | d | L/(d + L) | Water Factor | D$_{CB}$ (mJ/cm$^2$) |
|---|---|---|---|---|---|---|---|---|---|---|
| | | | 1e6 beads | | | | | | | |
| 1 | 60 | 0.44 | 0.0144 | 1.000 | 0.975 | 51.75 | 1.276 | 0.9759 | 0.97914 | 24.6 |
| 2 | 120 | 0.44 | 0.0144 | 1.000 | 0.975 | 51.75 | 1.231 | 0.9768 | 0.97987 | 49.3 |
| 3 | 180 | 0.44 | 0.0144 | 1.000 | 0.975 | 51.75 | 1.186 | 0.9776 | 0.98059 | 74.0 |
| 4 | 240 | 0.44 | 0.0144 | 1.000 | 0.975 | 51.75 | 1.141 | 0.9784 | 0.98132 | 98.9 |
| 5 | 300 | 0.44 | 0.0144 | 1.000 | 0.975 | 51.75 | 1.096 | 0.9793 | 0.98205 | 123.8 |
| 6 | 360 | 0.44 | 0.0144 | 1.000 | 0.975 | 51.75 | 1.051 | 0.9801 | 0.98278 | 148.8 |
| 7 | 420 | 0.44 | 0.0144 | 1.000 | 0.975 | 51.75 | 1.006 | 0.9809 | 0.98351 | 173.8 |
| 10 | 600 | 0.44 | 0.0144 | 1.000 | 0.975 | 51.75 | 0.961 | 0.9818 | 0.98424 | 248.7 |
| 15 | 900 | 0.44 | 0.0144 | 1.000 | 0.975 | 51.75 | 0.916 | 0.9826 | 0.98497 | 373.7 |
| 20 | 1200 | 0.44 | 0.0144 | 1.000 | 0.975 | 51.75 | 0.871 | 0.9834 | 0.98570 | 499.0 |

TABLE GG

Beads in Mab FVIP without Tyrosine (start with 30 ml, remove 1 ml at each time point) Visible Light Filter Removed from UVS-28 Lamp

| Minutes | Theoretical Exposure Time for SDS (s) | Theoretical Exposure time for Material | Avg UV Intensity (mW/cm$^2$) | A254 | P$_1$ | (1-R) | L | d | L/(d + L) | Water Factor | D$_{CB}$ (mJ/cm$^2$) |
|---|---|---|---|---|---|---|---|---|---|---|---|
| | | | | 1e6 beads | | | | | | | |
| 1 | 60 | 1962 | 0.41 | 10.422 | 1.000 | 0.975 | 51.75 | 1.276 | 0.9759 | 0.03266 | 25.0 |
| 2 | 120 | 3763 | 0.41 | 10.422 | 1.000 | 0.975 | 51.75 | 1.231 | 0.9768 | 0.03385 | 50.0 |
| 3 | 180 | 5462 | 0.41 | 10.422 | 1.000 | 0.975 | 51.75 | 1.186 | 0.9776 | 0.03514 | 75.0 |
| 4 | 240 | 7001 | 0.41 | 10.422 | 1.000 | 0.975 | 51.75 | 1.141 | 0.9784 | 0.03652 | 100.0 |
| 5 | 300 | 8396 | 0.41 | 10.422 | 1.000 | 0.975 | 51.75 | 1.096 | 0.9793 | 0.03802 | 125.0 |
| 6 | 360 | 9656 | 0.41 | 10.422 | 1.000 | 0.975 | 51.75 | 1.051 | 0.9801 | 0.03965 | 150.0 |
| 7 | 420 | 10774 | 0.41 | 10.422 | 1.000 | 0.975 | 51.75 | 1.006 | 0.9809 | 0.04142 | 175.0 |
| 10 | 600 | 14690 | 0.41 | 10.422 | 1.000 | 0.975 | 51.75 | 0.961 | 0.9818 | 0.04336 | 250.0 |
| 15 | 900 | 20986 | 0.41 | 10.422 | 1.000 | 0.975 | 51.75 | 0.916 | 0.9826 | 0.04549 | 375.0 |
| 20 | 1200 | 26584 | 0.41 | 10.422 | 1.000 | 0.975 | 51.75 | 0.871 | 0.9834 | 0.04784 | 500.0 |

TABLE HH

Beads in Mab FVIP without Tyrosine (start with 30 ml, remove 1 ml at each time point) Visible Light Filter Removed from UVS-28 Lamp

| Minutes | Theoretical Exposure Time for SDS (s) | Theoretical Exposure time for Material | Avg UV Intensity (mW/cm$^2$) | A254 | P$_1$ | (1-R) | L | d | L/(d + L) | Water Factor | D$_{CB}$ (mJ/cm$^2$) |
|---|---|---|---|---|---|---|---|---|---|---|---|
| | | | | 1e6 beads | | | | | | | |
| 1 | 60 | 1889 | 0.43 | 10.52 | 1.0 | 0.975 | 51.75 | 1.276 | 0.9759 | 0.03235 | 25.0 |
| 2 | 120 | 3641 | 0.43 | 10.52 | 1.0 | 0.975 | 51.75 | 1.231 | 0.9768 | 0.03354 | 50.0 |
| 3 | 180 | 5257 | 0.43 | 10.52 | 1.0 | 0.975 | 51.75 | 1.186 | 0.9776 | 0.03481 | 75.0 |
| 4 | 240 | 6738 | 0.43 | 10.52 | 1.0 | 0.975 | 51.75 | 1.141 | 0.9784 | 0.03618 | 100.0 |
| 5 | 300 | 8083 | 0.43 | 10.52 | 1.0 | 0.975 | 51.75 | 1.096 | 0.9793 | 0.03767 | 125.0 |
| 6 | 360 | 9294 | 0.43 | 10.52 | 1.0 | 0.975 | 51.75 | 1.051 | 0.9801 | 0.03926 | 150.0 |
| 7 | 420 | 10369 | 0.43 | 10.52 | 1.0 | 0.975 | 51.75 | 1.006 | 0.9809 | 0.04104 | 175.0 |
| 10 | 600 | 14139 | 0.43 | 10.52 | 1.0 | 0.975 | 51.75 | 0.961 | 0.9818 | 0.04296 | 250.0 |
| 15 | 900 | 20198 | 0.43 | 10.52 | 1.0 | 0.975 | 51.75 | 0.916 | 0.9826 | 0.04507 | 375.0 |
| 20 | 1200 | 25586 | 0.43 | 10.52 | 1.0 | 0.975 | 51.75 | 0.871 | 0.9834 | 0.04740 | 500.0 |

Figure 26:
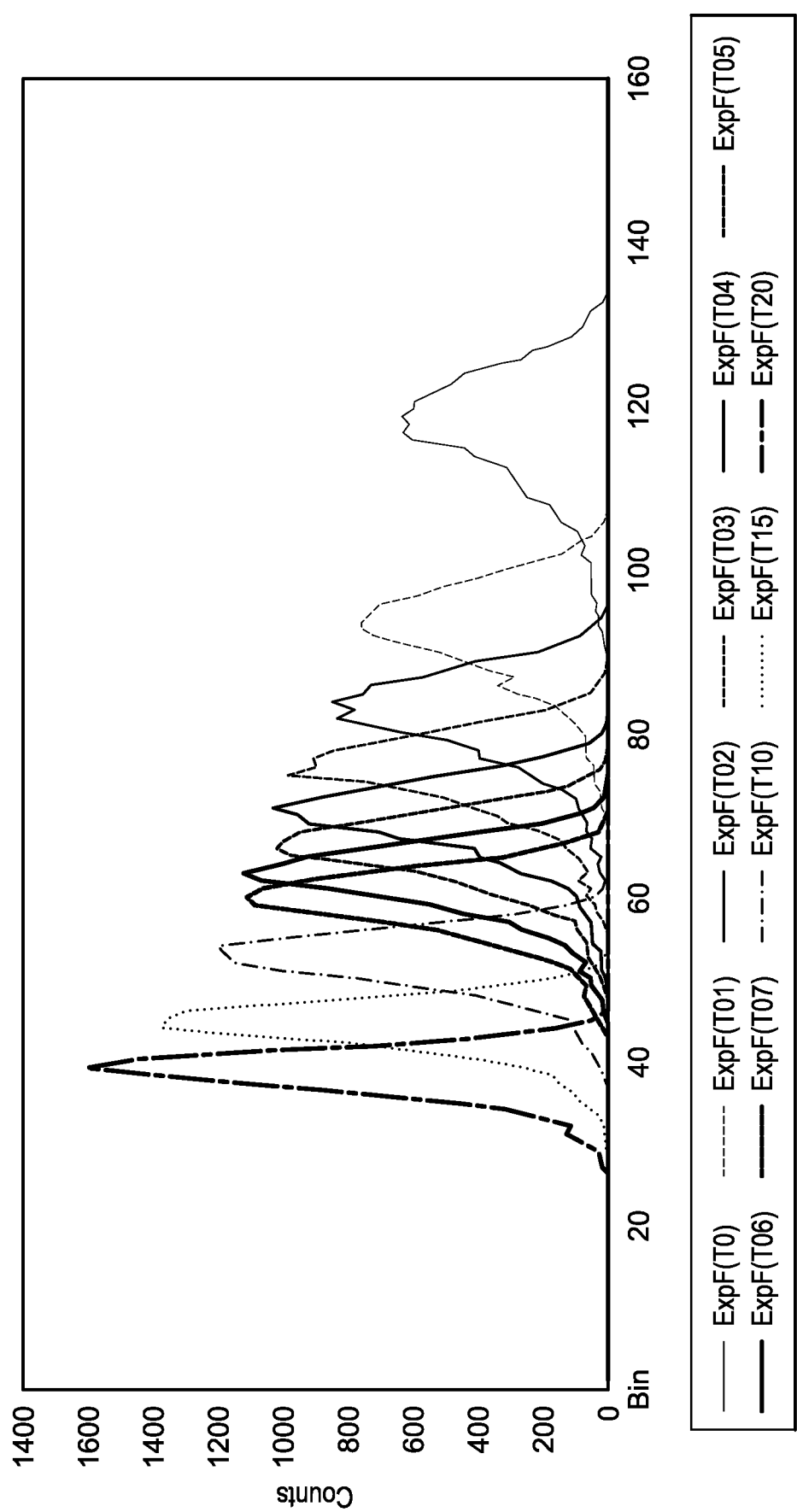
FIG. 26 is a plot showing overlay fluorescence distributions as measured by FACS wherein samples were derived from treatment of microspheres in SDS solution with various residence time exposures with a collimated beam device.
Figure 28:
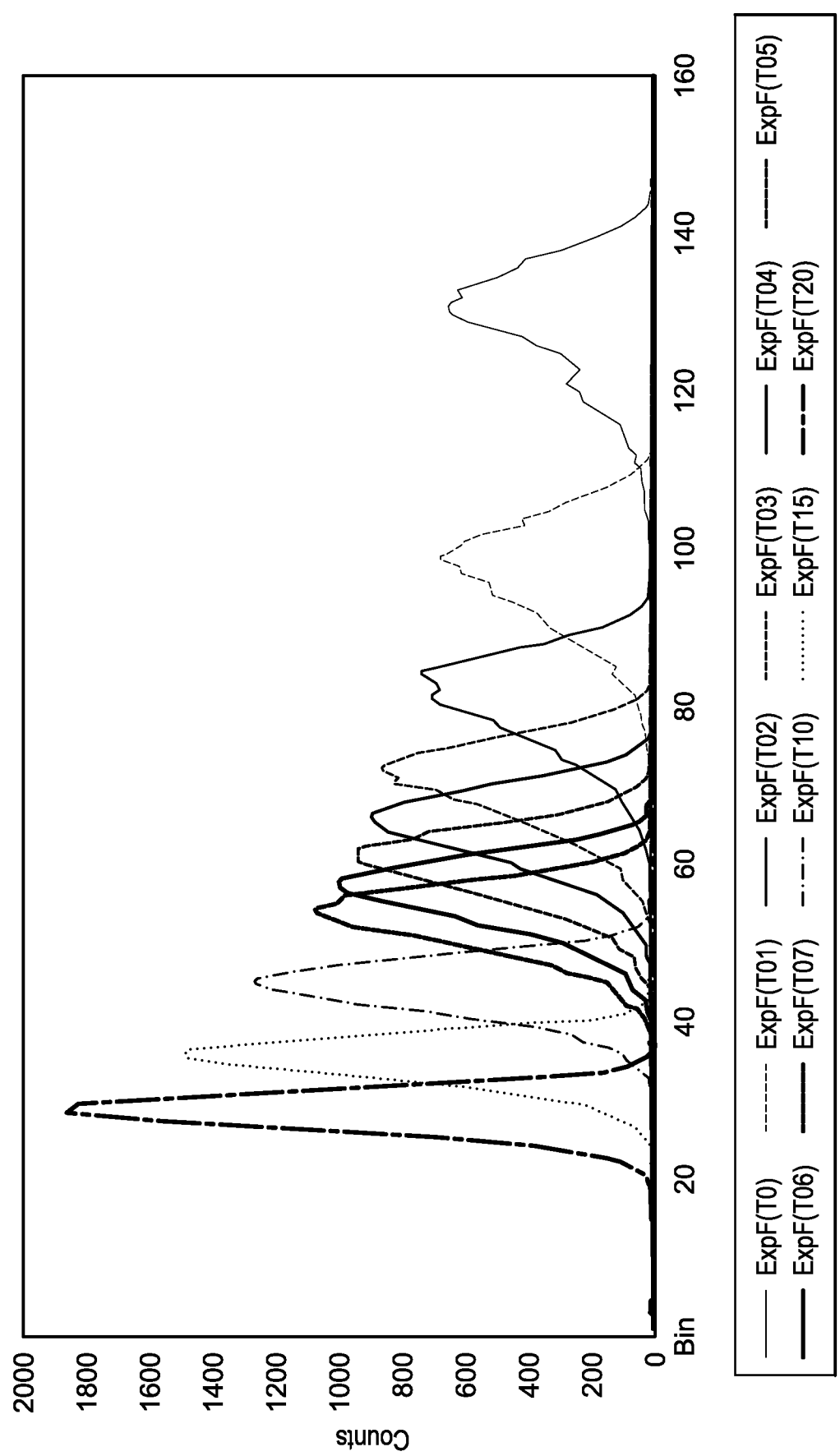
FIG. 28 is a plot showing overlay fluorescence distributions as measured by FACS wherein samples were derived from treatment of microspheres in Mab FVIP solution with various residence time exposures with a collimated beam device.
Figure 29A:
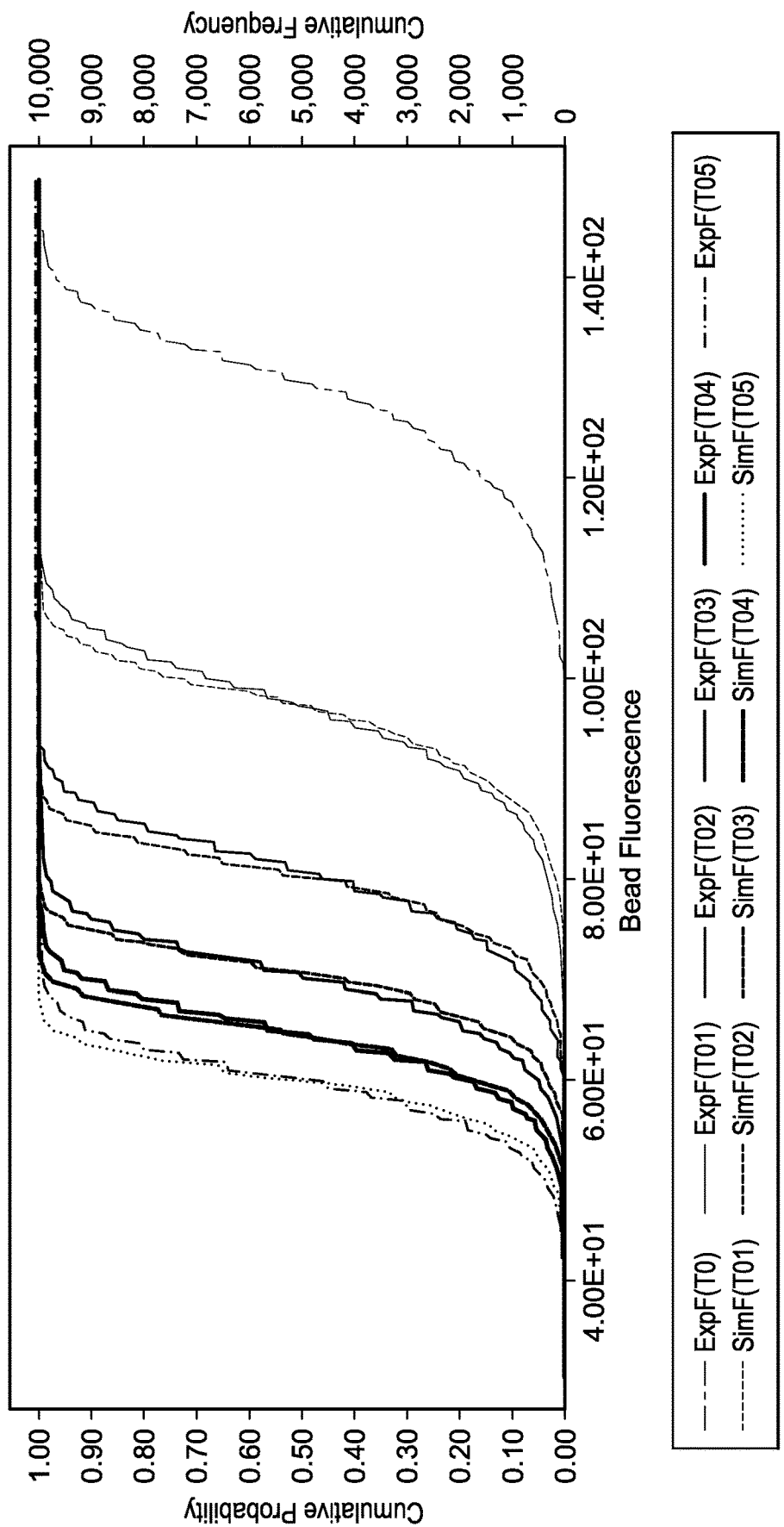
Figure 29B:
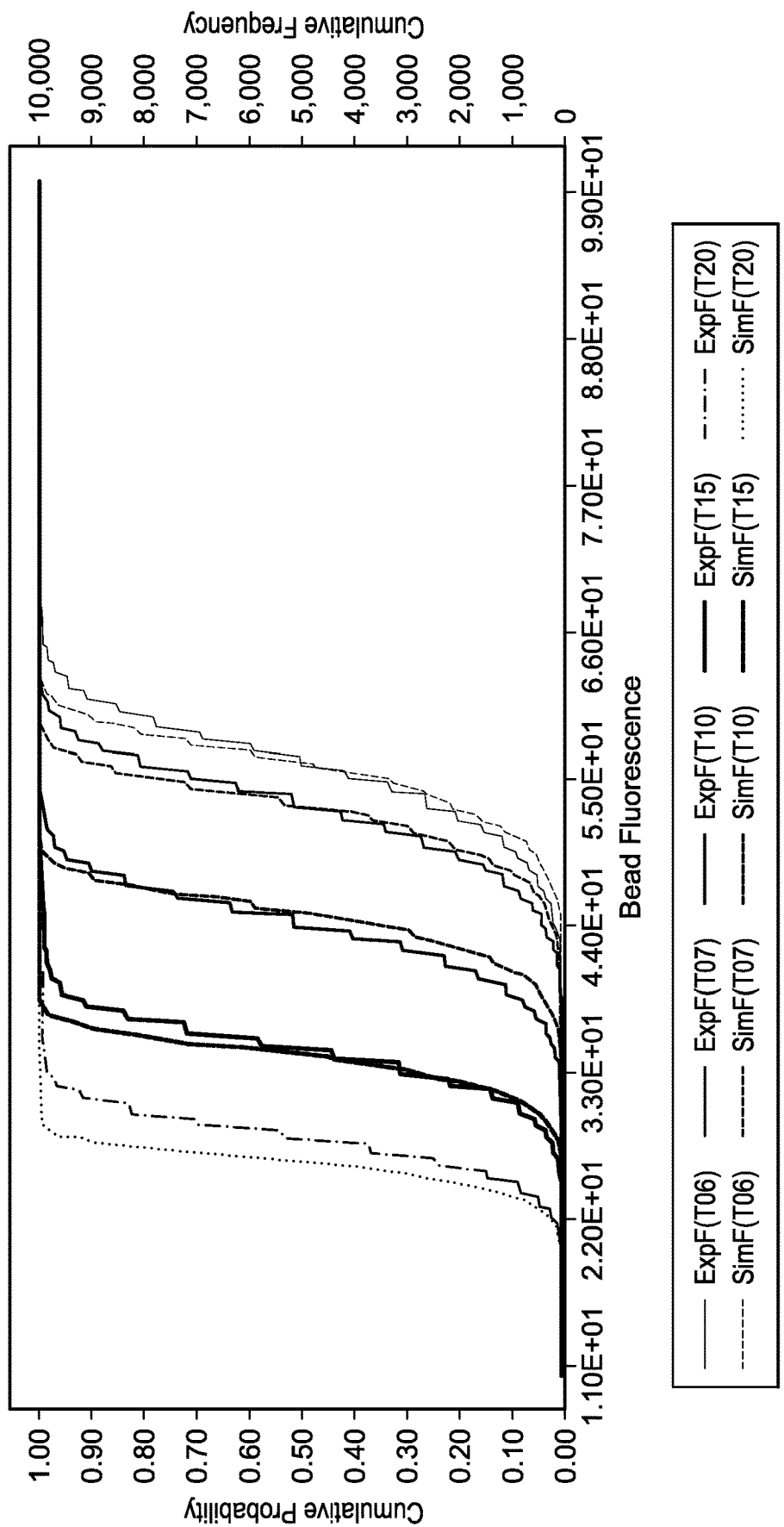
FIG. 29B shows the results of a high dose UVC experiment versus simulated distribution.
Figure 30:
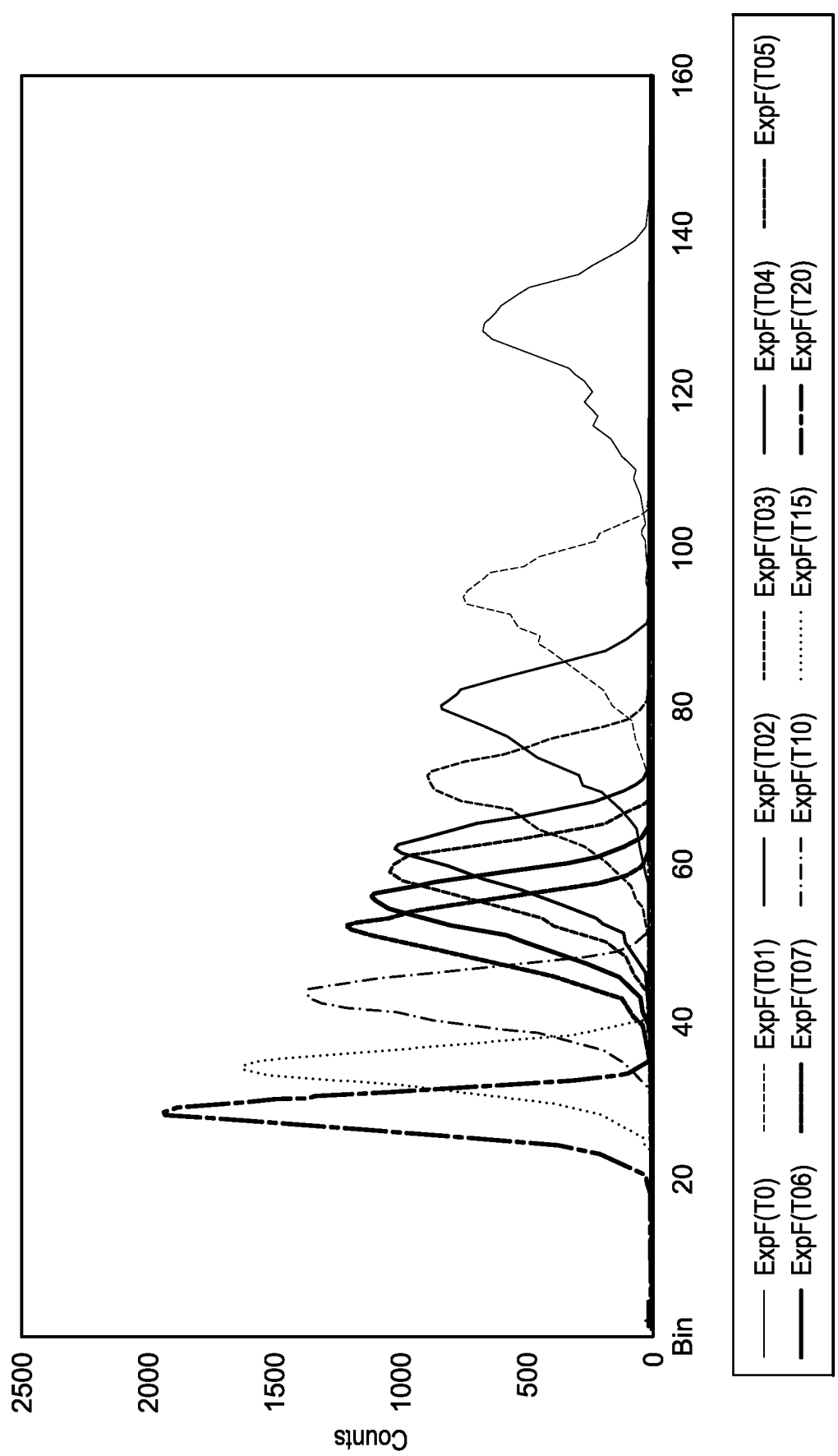
FIG. 30 is a plot showing overlay fluorescence distributions as measured by FACS wherein samples were derived from treatment of microspheres in Mab FVIP solution containing tyrosine with various residence time exposures with a collimated beam device.
Figure 31A:
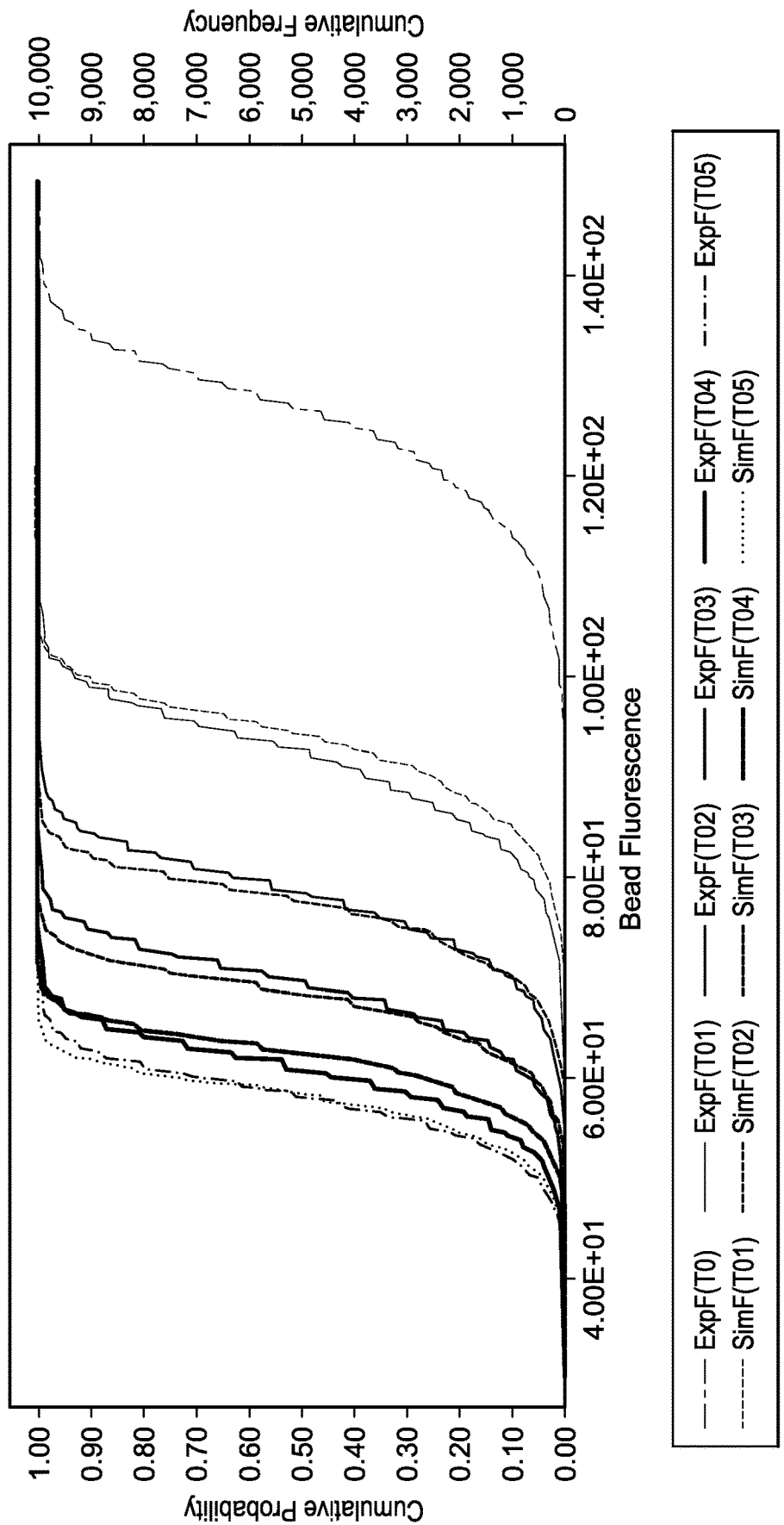
Figure 31B:
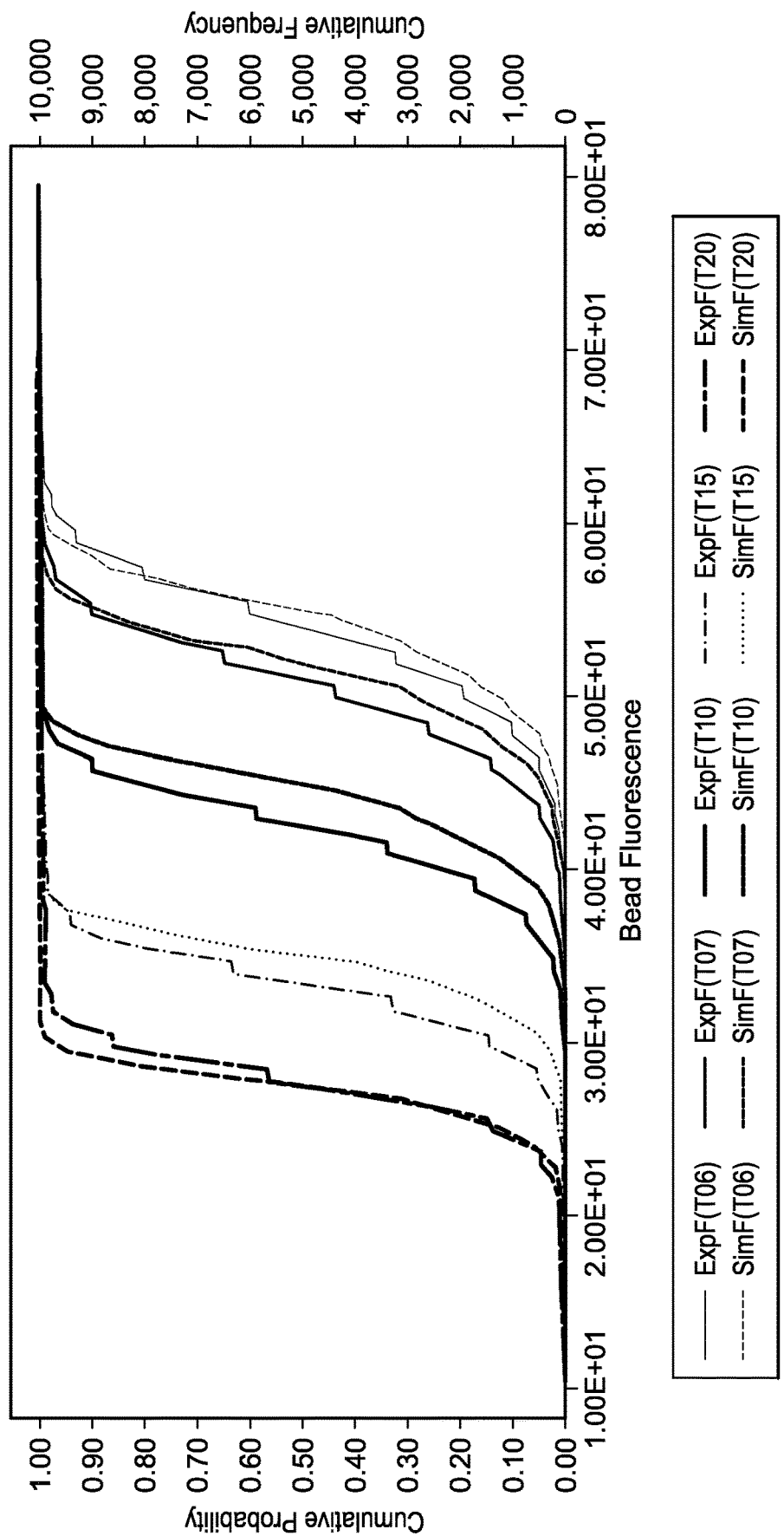
FIG. 31B shows the results of a high dose UVC experiment versus simulated distribution.

The fluorescence distributions of the exposed and control (unexposed) microspheres contained in the SDS solution, the protein-A purified Mab FVIP, and the protein-A purified Mab FVIP supplemented with tyrosine were obtained by FACS analysis as described in Examples 1 and 4 and are shown in FIGS. 26, 28, and 30 respectively.

Figure 27A:
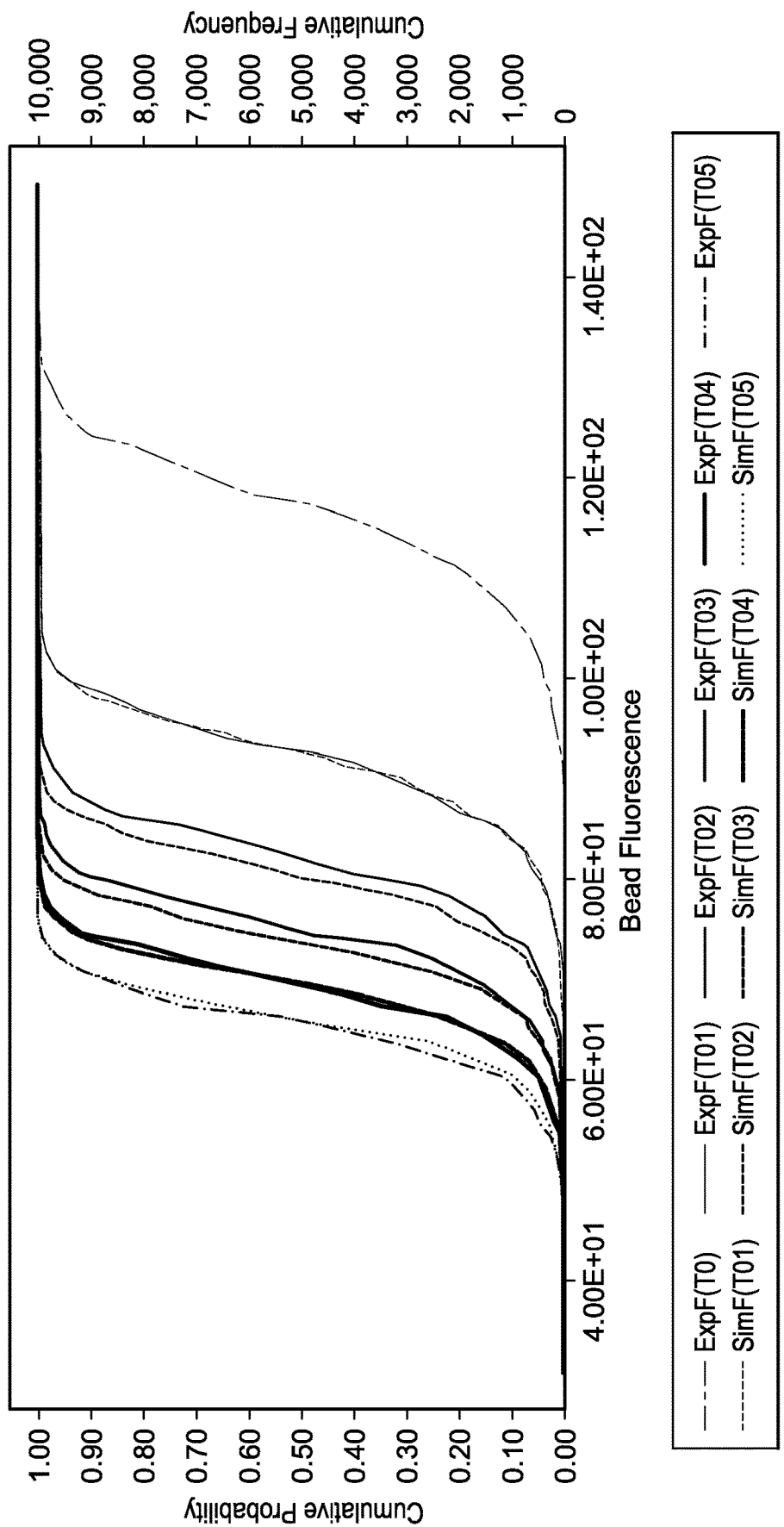
Figure 27B:
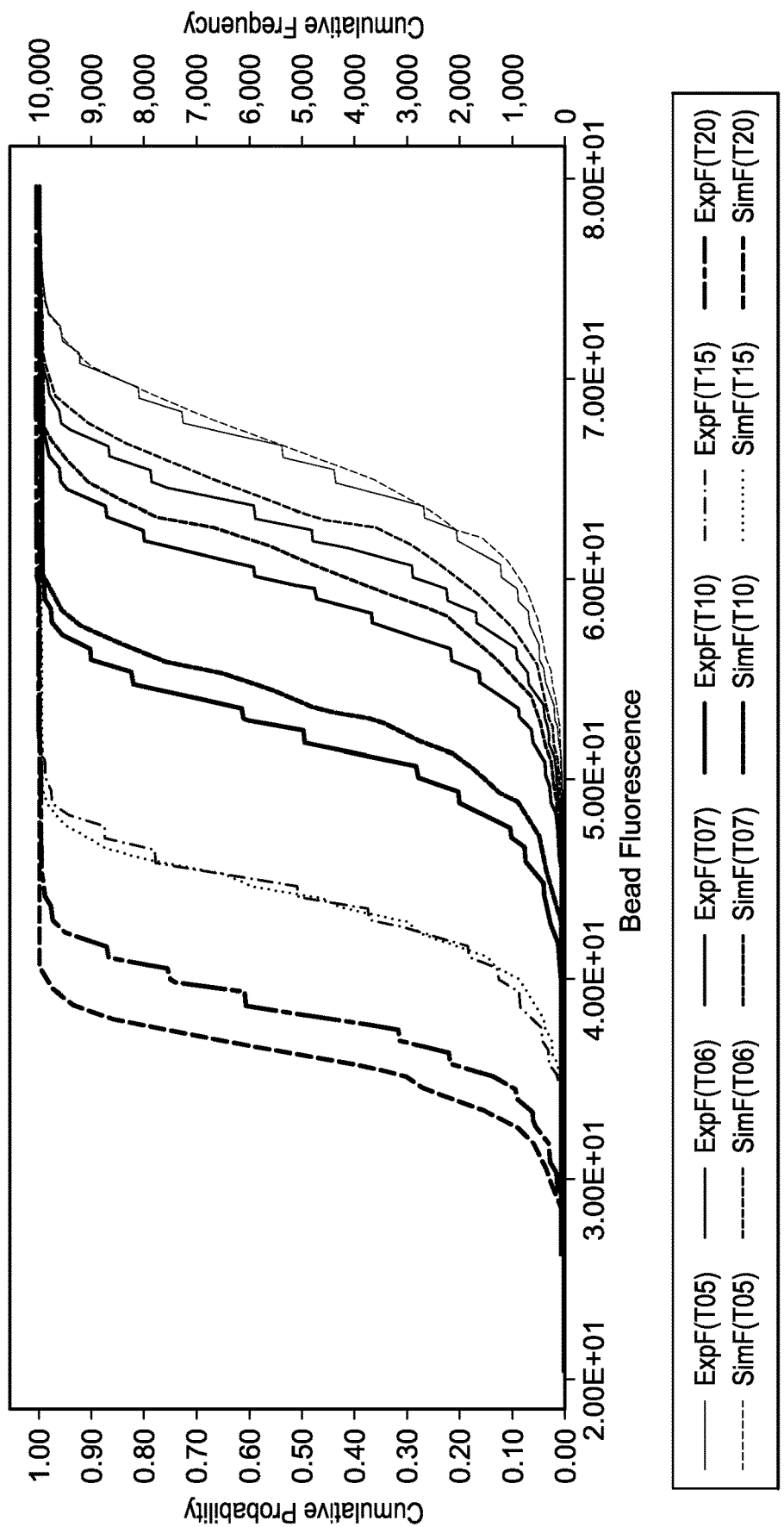
FIG. 27B shows the results of a high dose UVC experiment versus simulated distribution.

Following the measurement of the fluorescent distribution, a mathematical deconvolution was performed in order to determine the photo-bleaching kinetic constants. The methods employed in the deconvolution are described in Example 2. Comparison of the measured fluorescence distributions with simulated distributions using optimum bleaching kinetic constants for microspheres contained in the SDS solution, the protein-A purified Mab FVIP, and the protein-A purified Mab FVIP supplemented with tyrosine are shown in FIGS. 27A and B, 29A and B, and 31A and B, respectively. The measured and simulated distributions for complex high optically absorbing solutions, represented by protein-A purified Mab FVIP and protein-A purified Mab FVIP supplemented with tyrosine, are comparably accurate as those for low optically absorbing solutions, represented by SDS solutions.

The quantitative values for microsphere bleaching-kinetic parameters were determined using the deconvolution procedures described in Example 2 and are shown in Table II. Importantly, the quantitative values for the bleaching-kinetic parameters are essentially the same for bleaching in the complex high optically-absorbing solutions, represented by protein-A purified Mab FVIP and protein-A purified Mab FVIP supplemented with tyrosine, as they are in low optical-absorbing simple solutions, represented by SDS solution.

TABLE II

| Fluid | Measure | F(T0) | Kb1 | Kb2 | w1 |
|---|---|---|---|---|---|
| SDS | Mean | 1.2E+02 | 3.5E−02 | 1.6E−03 | 3.2E−01 |
| | Std Dev | 8.2E+00 | 1.5E−03 | 1.1E−05 | 1.2E−03 |
| MabFVIP | Mean | 1.3E+02 | 3.2E−02 | 2.1E−03 | 4.1E−01 |
| | Std Dev | 9.0E+00 | 1.0E−03 | 2.7E−05 | 2.5E−03 |
| Mab FVIP w/Tyrosine | Mean | 1.3E+02 | 3.2E−02 | 1.9E−03 | 4.3E−01 |
| | Std Dev | 9.9E+00 | 6.3E−05 | 5.1E−06 | 4.5E−04 |

Treatment of Mab protein with UVc radiation can produce limited damage as measured by size exclusion chromatography. Inclusion of tyrosine as a protectant can reduce the extent of damage. As seen in Table JJ, the inclusion of tyrosine in Mab FVIP reduced the amount of HMW impurity produced at each treatment dose. Despite providing protection against UVC induced protein damage, tyrosine does not interfere with the bleaching of the microspheres as evidenced by essentially same bleaching-kinetic parameter values between FVIP and FVIP with tyrosine.

TABLE JJ

| | Mab FVIP | | | | | | Mab FVIP w/Tyrosine | | | | | |
|---|---|---|---|---|---|---|---|---|---|---|---|---|
| Theoretical Exposure time for Material | Avg UV Intensity (mW/cm$^2$) | A254 | Water Factor | $D_{CB}$ (mJ/cm$^2$) | HMW | Main | Theoretical Exposure time for Material | Avg UV Intensity (mW/cm$^2$) | A254 | Water Factor | $D_{CB}$ (mJ/cm$^2$) | HMW | Main |
| 0 | | 1e6 beads | | 0 | 3.9 | 95.9 | 0 | | 1e6 beads | | 0 | 3.8 | 96.0 |
| 1962 | 0.41 | 10.422 | 0.03266 | 25.0 | 4.5 | 95.2 | 1889 | 0.43 | 10.52 | 0.03236 | 25.0 | 4.3 | 95.4 |
| 3783 | 0.41 | 10.422 | 0.03385 | 50.0 | 5.2 | 94.5 | 3641 | 0.43 | 10.52 | 0.03354 | 50.0 | 4.7 | 95.0 |
| 5462 | 0.41 | 10.422 | 0.03514 | 75.0 | 6 | 93.7 | 5257 | 0.43 | 10.52 | 0.03481 | 75.0 | 5.3 | 94.4 |
| 7001 | 0.41 | 10.422 | 0.03662 | 100.0 | 6.6 | 93.1 | 6738 | 0.43 | 10.52 | 0.03618 | 100.0 | 6.0 | 93.6 |
| 8398 | 0.41 | 10.422 | 0.03802 | 125.0 | 7.3 | 92.4 | 8083 | 0.43 | 10.52 | 0.03767 | 125.0 | 6.2 | 93.4 |
| 9656 | 0.41 | 10.422 | 0.03995 | 150.0 | 7.9 | 91.7 | 9294 | 0.43 | 10.52 | 0.03928 | 150.0 | 6.7 | 92.9 |
| 10774 | 0.41 | 10.422 | 0.04142 | 175.0 | 8.5 | 91.1 | 10369 | 0.43 | 10.52 | 0.04104 | 175.0 | 7.1 | 92.4 |
| 14690 | 0.41 | 10.422 | 0.04336 | 250.0 | 11.65 | 86.5 | 14139 | 0.43 | 10.52 | 0.04296 | 250.0 | 8.8 | 90.6 |
| 20986 | 0.41 | 10.422 | 0.04549 | 375.0 | 14.8 | 81.9 | 20198 | 0.43 | 10.52 | 0.04507 | 375.0 | 13.2 | 86.0 |
| 26584 | 0.41 | 10.422 | 0.04784 | 500.0 | 19 | 77.2 | 25586 | 0.43 | 10.52 | 0.04740 | 500.0 | 15.6 | 83.3 |

Example 7

Inactivation of Virus and Mycoplasma in Media by UVc Treatment

Generating a Standard Curve

Control mixtures were prepared by spiking adventitious agents into two different media preparations; information pertaining to the agents and media preparations used is summarized in Table KK. A 30 mL aliquot each of basal Media B or E was spiked with either (A) 5% (v/v) MMV stock, (B) 5% (v/v) CVV stock, or (C) 100 CFU/ml M. arginini stock. The spiked solution was transferred to a 100 mm petri dish with a magnetic stir bar. A 1 mL aliquot was removed at T=0 minute (unexposed test article). The petri dish was placed under UVC light and the timer was started; 1 mL aliquots of the exposed sample were removed at the desired time points as shown in Table LL and Table MM. Collected samples were assayed by suitable means for the presence of viable agent.

TABLE KK

| Label | Description |
|---|---|
| | Agents |
| MMV | Mouse Minute Virus-single stranded non-enveloped DNA virus |
| CVV | Cache Valley Virus-single stranded enveloped RNA virus |

TABLE KK-continued

| Label | Description |
|---|---|
| M. arginini | Mycoplasma arginine-common mycoplasma strain |
| | Note: virus titer = (Log10 TCID50/ml), Mycoplasma titer = (CFU/ml) |
| | Media |
| Basal Medium B | Composed from water, basal DMEM F-12, fetal bovine serum and NaHCO3 |
| Basal Medium E | Composed from water, basal DMEM F-12 and NaHCO3 |
| | Note: "basal" denotes media deplete of heterocyclic amino acid acids and vitamins determined susceptible to UVc treatment |

As shown in Table LL and Table MM, exposure of virus and mycoplasma to UVc radiation resulting in complete inactivation above a threshold dose which could differ slightly between runs due to normal experimental variability. As observed in prior examples, however, the extent of fluorescent bleaching of microspheres in the optically absorbing solutions is progressively related to the received dose; thereby affording more accurate determination of the UVc dose received.

TABLE LL

| Time (min) | Exposure Time (s) | Avg UV Intensity (mW/cm$^2$) | A254 | Water Factor | $D_{CB}$ (mJ/cm$^2$) | MMV | | CVV | | M. arginini | |
|---|---|---|---|---|---|---|---|---|---|---|---|
| | | | | | | Run 1 | Run 2 | Run 1 | Run 2 | Run 1 | Run 2 |
| 0 | 0 | 0.12 | 1.3465 | 0.24793 | 0 | Run 1 | Run 2 | Run 1 | Run 2 | Run 1 | Run 2 |
| 3 | 180 | 0.12 | 1.3465 | 0.25625 | 5.5 | + | + | + | + | + | + |
| 6 | 360 | 0.12 | 1.3465 | 0.26507 | 10.9 | + | + | + | 0 | 0 | 0 |
| 9 | 540 | 0.12 | 1.3465 | 0.27446 | 17 | 0 | + | 0 | 0 | 0 | 0 |
| 12 | 720 | 0.12 | 1.3465 | 0.28444 | 23.4 | 0 | 0 | 0 | 0 | 0 | 0 |
| 15 | 900 | 0.12 | 1.3465 | 0.29509 | 30.4 | 0 | 0 | 0 | 0 | 0 | 0 |
| 18 | 1080 | 0.12 | 1.3465 | 0.30644 | 38 | 0 | 0 | 0 | 0 | 0 | 0 |
| 21 | 1260 | 0.12 | 1.3465 | 0.31857 | 46.1 | 0 | 0 | 0 | 0 | 0 | 0 |
| 30 | 1800 | 0.12 | 1.3465 | 0.33154 | 68.6 | 0 | 0 | 0 | 0 | 0 | 0 |

Pf, (1-R), L, d and L/(d + L) have the same values as in Example 5
(+) indicates remaining viable tested agent, (0) indicates complete inactivated of tested agent

TABLE MM

| Time (min) | Exposure Time (s) | Avg UV Intensity (mW/cm$^2$) | A254 | Water Factor | $D_{CB}$ (mJ/cm$^2$) | MMV Run 1 | MMV Run 2 | CVV Run 1 | CVV Run 2 | M. arginini Run 1 | M. arginini Run 2 |
|---|---|---|---|---|---|---|---|---|---|---|---|
| 0 | 0 | 0.12 | 0.6305 | 0.45515 | 0 | + |  | + | + | + | + |
| 3 | 180 | 0.12 | 0.6305 | 0.46586 | 9.6 | + |  | + | + | + | + |
| 6 | 360 | 0.12 | 0.6305 | 0.47697 | 19.6 | + |  | 0 | 0 | 0 | 0 |
| 9 | 540 | 0.12 | 0.6305 | 0.4885 | 30.2 | + |  | 0 | 0 | 0 | 0 |
| 12 | 720 | 0.12 | 0.6305 | 0.50046 | 41.3 | + |  | 0 | 0 | 0 | 0 |
| 15 | 900 | 0.12 | 0.6305 | 0.51288 | 52.9 | 0 |  | 0 | 0 | 0 | 0 |
| 18 | 1080 | 0.12 | 0.6305 | 0.52577 | 65.1 | 0 |  | 0 | 0 | 0 | 0 |
| 21 | 1260 | 0.12 | 0.6305 | 0.53915 | 78 | 0 |  | 0 | 0 | 0 | 0 |
| 30 | 1800 | 0.12 | 0.6305 | 0.55306 | 114.4 | 0 |  | 0 | 0 | 0 | 0 |

Pf, (1-R), L, d and L/(d + L) have the same values as in Example 5
(+) indicates remaining viable tested agent, (0) indicates complete inactivated of tested agent

What is claimed is:

1. A method of determining the dose of UVC light delivered to a sample comprising a low optical transmission complex fluid comprising:
   (a) measuring the fluence rate delivered by a NIST traceable UVC source;
   (b) generating a standard curve by:
      (i) contacting a bleachable fluorescence emitter with a low optical transmission complex fluid comprising cell culture media to form a control mixture, wherein the bleachable fluorescence emitter is not contacted with a high optical transmission solution or water that does not contain carbohydrates and/or amino acids as solutes;
      (ii) exposing the control mixture to UVC light for an initial residence time;
      (iii) obtaining an aliquot from the control mixture;
      (iv) measuring the fluorescence emitted by the aliquot of (iii);
      (v) repeating (ii)-(iv) one or more times, wherein the control mixture is exposed to UVC light for a residence time that is longer than the initial residence time;
      (vi) correlating the fluorescence emitted with the residence time;
   (c) contacting a bleachable fluorescence emitter with a test fluid comprising a low optical transmission complex fluid comprising cell culture media to form a test mixture;
   (d) exposing the test mixture to UVC light for a selected residence time;
   (e) measuring the fluorescence emitted by the test mixture; and
   (f) determining the dose delivered to the test mixture using the standard curve of (b).

2. The method of claim 1, wherein the UVC light has a wavelength in the range of about 200 nm to about 280 nm.

3. The method of claim 2, wherein the UVC light has a wavelength of 254 nm.

4. The method of claim 1, wherein the bleachable fluorescence emitter comprises a UV-sensitive fluorescent microsphere.

5. The method of claim 1, wherein the dose is provided as one of a dose distribution, a mean dose, a P10 dose, a P50 dose and a P90 dose.

6. The method of claim 1, wherein the fluence rate delivered by the UVC source is measured using a NIST traceable UVC detector.

7. The method of claim 1, wherein correlating the fluorescence emitted with the residence time in step (vi) comprises measuring the fluorescence distributions of aliquots from the control mixture taken at different residence times and determining photo-bleaching kinetic parameters in a photo-bleaching equation based on the fluorescence distributions.

8. The method of claim 7, wherein the UVC light dose delivered to the test mixture is determined from the fluorescence distribution of the test mixture using the photo-bleaching equation and determined photo-bleaching kinetic parameters.

9. The method of claim 1, wherein the fluorescence emitted from the aliquots of the control mixture and the test mixture is measured with a digital flow cytometer.

10. A method of determining the dose of UVC light delivered to a sample comprising a low optical transmission complex fluid comprising:
   (a) measuring the fluence rate delivered by a NIST traceable UVC source;
   (b) generating a standard curve by:
      (i) contacting a bleachable fluorescence emitter with a low optical transmission complex fluid to form a control mixture comprising cell culture media, wherein the bleachable fluorescence emitter is not contacted with a high optical transmission solution or water that does not contain carbohydrates and/or amino acids as solutes;
      (ii) exposing the control mixture to UVC light from the UVC source for an initial residence time;
      (iii) obtaining an aliquot from the control mixture;
      (iv) measuring the fluorescence emitted by the aliquot of (iii);
      (v) repeating (ii)-(iv) one or more times, wherein the control mixture is exposed to UVC light for a residence time that is longer than the initial residence time;
      (vi) calculating the UVC dose for each aliquot based on the measured fluence rate from the UVC source and residence time;
      (vii) correlating the fluorescence emitted with the UVC dose by measuring the fluorescence distributions of aliquots from the control mixture taken at different residence times and determining photo-bleaching kinetic parameters in a photo-bleaching equation based on the fluorescence distributions;
   (c) contacting a bleachable fluorescence emitter with a test fluid comprising a low optical transmission complex fluid comprising cell culture media to form a test mixture;
   (d) exposing the test mixture to UVC light for a selected residence time;

(e) measuring the fluorescence emitted by the test mixture; and (f) determining the dose delivered to the test mixture using the standard curve of (b).

11. The method of claim 10, wherein the UVC light dose delivered to the test mixture is determined from the fluorescence distribution of the test mixture using the photo-bleaching equation and the photo-bleaching kinetic parameters determined in step (vii).

12. The method of claim 11, wherein the low optical transmission complex fluid comprises a protein A-purified monoclonal antibody pool.

13. A method of determining the dose of UVC light delivered to a sample comprising a low optical transmission complex fluid comprising:
  (a) measuring the fluence rate delivered by a NIST traceable UVC source;
  (b) generating a standard curve by:
    (i) contacting a bleachable fluorescence emitter with a low optical transmission complex fluid to form a control mixture, wherein the wherein the bleachable fluorescence emitter is not contacted with a high optical transmission solution or water that does not contain carbohydrates and/or amino acids as solutes;
    (ii) exposing the control mixture to UVC light from the UVC source for an initial residence time;
    (iii) obtaining an aliquot from the control mixture;
    (iv) measuring the fluorescence emitted by the aliquot of (iii);
    (v) repeating (ii)-(iv) one or more times, wherein the control mixture is exposed to UVC light for a residence time that is longer than the initial residence time;
    (vi) calculating the UVC dose for each aliquot based on the measured fluence rate from the UVC source and residence time;
    (vii) correlating the fluorescence emitted with the UVC dose by measuring the fluorescence distributions of aliquots from the control mixture taken at different residence times and determining photo-bleaching kinetic parameters in a photo-bleaching equation based on the fluorescence distributions;
  (c) contacting a bleachable fluorescence emitter with a test fluid comprising a low optical transmission complex fluid to form a test mixture;
  (d) exposing the test mixture to UVC light for a selected residence time;
  (e) measuring the fluorescence emitted by the test mixture; and
  (f) determining the dose delivered to the test mixture using the standard curve of (b), wherein the UVC light dose delivered to the test mixture is determined from the fluorescence distribution of the test mixture using the photo-bleaching equation and the photo-bleaching kinetic parameters determined in step (vii).

14. The method of claim 13, wherein the low optical transmission complex fluid is selected from a fluid comprising cell culture media, a fluid comprising serum, a fluid comprising a mixture comprising a vitamin, a sugar and a pigment, and a fluid comprising a solution containing amino acids, peptides or proteins.

\* \* \* \* \*